United States Patent
Caravan et al.

(10) Patent No.: US 9,944,668 B2
(45) Date of Patent: Apr. 17, 2018

(54) MANGANESE-BASED MAGNETIC RESONANCE CONTRAST AGENTS

(71) Applicants: Peter Caravan, Cambridge, MA (US);
Eric M. Gale, Charlestown, MA (US);
Galen S. Loving, Charlestown, MA (US); Shereya Mukherjee,
Charlestown, MA (US); Jiang Zhu,
Charlestown, MA (US)

(72) Inventors: Peter Caravan, Cambridge, MA (US);
Eric M. Gale, Charlestown, MA (US);
Galen S. Loving, Charlestown, MA (US); Shereya Mukherjee,
Charlestown, MA (US); Jiang Zhu,
Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/759,114

(22) PCT Filed: Jan. 7, 2014

(86) PCT No.: PCT/US2014/010486
§ 371 (c)(1),
(2) Date: Jul. 2, 2015

(87) PCT Pub. No.: WO2014/107722
PCT Pub. Date: Jul. 10, 2014

(65) Prior Publication Data
US 2015/0336997 A1 Nov. 26, 2015

Related U.S. Application Data

(60) Provisional application No. 61/749,614, filed on Jan. 7, 2013.

(51) Int. Cl.
| | | |
|---|---|---|
| A61K 49/14 | (2006.01) | |
| A61K 49/16 | (2006.01) | |
| C07F 13/00 | (2006.01) | |
| A61K 49/06 | (2006.01) | |
| A61K 51/04 | (2006.01) | |
| A61K 49/10 | (2006.01) | |
| A61B 5/055 | (2006.01) | |
| A61B 5/00 | (2006.01) | |

(52) U.S. Cl.
CPC .......... *C07F 13/005* (2013.01); *A61B 5/0035* (2013.01); *A61B 5/055* (2013.01); *A61K 49/06* (2013.01); *A61K 49/103* (2013.01); *A61K 49/106* (2013.01); *A61K 49/14* (2013.01); *A61K 49/16* (2013.01); *A61K 51/04* (2013.01); *A61K 51/0455* (2013.01)

(58) Field of Classification Search
CPC ........ A61K 49/00; A61K 49/06; A61K 49/14; A61K 49/16
See application file for complete search history.

(56) References Cited

U.S. PATENT DOCUMENTS

| | | | |
|---|---|---|---|
| 4,622,420 A | 11/1986 | Meares et al. | |
| 4,647,447 A | 3/1987 | Gries et al. | |
| 4,889,931 A * | 12/1989 | Rocklage | A61K 49/06 540/465 |

FOREIGN PATENT DOCUMENTS

| | | |
|---|---|---|
| CN | 1687181 | 10/2005 |
| CN | 101678128 | 3/2010 |
| EP | 0 308 983 | 3/1989 |
| EP | 0 369 497 | 9/1989 |
| WO | WO 2014/107722 | 7/2014 |

OTHER PUBLICATIONS

Troughton et al., "Synthesis and evaluation of a high relaxivity manganese(II)-based MRI contrast agent," Inorg. Chem., 2004, 43:6313-23.
Extended European Search Report in European Application No. 14735166.2, dated Jul. 25, 2016, 8 pages.
Office Action in Chinese Application No. 201480012793.7, dated Mar. 31, 2017, 11 pages (with English translation).
International search report dated Jun. 19, 2014 in international application No. PCT/US2014/010486, 2 pgs.

* cited by examiner

*Primary Examiner* — Michael G Hartley
*Assistant Examiner* — Jagadishwar R Samala
(74) *Attorney, Agent, or Firm* — Fish & Richardson P.C.

(57) ABSTRACT

Manganese coordination complexes with utility as magnetic resonance probes and as biological reductant sensors are disclosed. In one embodiment, ligands can stabilize both the $Mn^{2+}$ and $Mn^{3+}$ oxidation states. In the presence of a reductant such as glutathione, low relaxivity $Mn^{III}$-HBET is rapidly converted to high relaxivity $Mn^{II}$-HBET with a 3-fold increase in relaxivity, and concomitant increase in magnetic resonance signal. In another embodiment, ligands were designed to chelate Mn(ll) in a thermodynamically stable and kinetically inert fashion while allowing for direct interaction of Mn(ll) with water. In yet another embodiment, high molecular weight multimers containing six Mn(ll) chelators were prepared. The high molecular weight results in slower tumbling of the molecules in solution and can strongly enhance the Mn(ll) relaxivity.

9 Claims, 39 Drawing Sheets

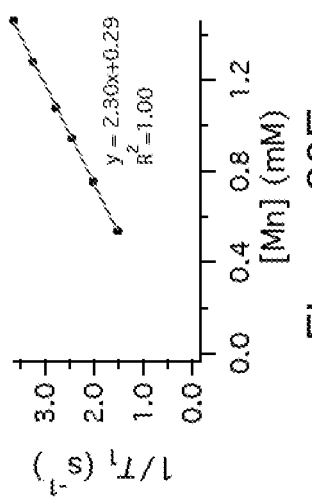

MANGANESE-BASED MAGNETIC RESONANCE CONTRAST AGENTS

CROSS-REFERENCES TO RELATED APPLICATIONS

This application claims priority from U.S. Patent Application No. 61/749,614 filed Jan. 7, 2013.

STATEMENT REGARDING FEDERALLY SPONSORED RESEARCH

This invention was made with government support under grant numbers CA161221 and RR14075 awarded by the National Cancer Institute and National Center for Research Resources. The government has certain rights in the invention.

BACKGROUND OF THE INVENTION

1. Field of the Invention

The invention relates to contrast agents for magnetic resonance imaging. The invention also relates to methods for preparing the contrast agents.

2. Description of the Related Art

When a substance such as human tissue is subjected to a uniform magnetic field (polarizing field $B_0$), the individual magnetic moments of the excited nuclei in the tissue attempt to align with this polarizing field, but process about it in random order at their characteristic Larmor frequency. If the substance, or tissue, is subjected to a magnetic field (excitation field $B_1$) that is in the x-y plane and that is near the Larmor frequency, the net aligned moment, Mz, may be rotated, or "tipped", into the x-y plane to produce a net transverse magnetic moment Mt. A signal is emitted by the excited nuclei or "spins", after the excitation signal $B_1$ is terminated, and this signal may be received and processed to form an image.

In magnetic resonance imaging (MRI) systems, the excited spins induce an oscillating sine wave signal in a receiving coil. The frequency of this signal is near the Larmor frequency, and its initial amplitude, is determined by the magnitude of the transverse magnetic moment Mt. The amplitude, A, of the emitted NMR signal decays in an exponential fashion with time, t. The decay constant $1/T^*_2$ depends on the homogeneity of the magnetic field and on $T_2$, which is referred to as the "spin-spin relaxation" constant, or the "transverse relaxation" constant. The $T_2$ constant is inversely proportional to the exponential rate at which the aligned precession of the spins would dephase after removal of the excitation signal $B_1$ in a perfectly homogeneous field. The practical value of the $T_2$ constant is that tissues have different $T_2$ values and this can be exploited as a means of enhancing the contrast between such tissues.

Another important factor that contributes to the amplitude A of the NMR signal is referred to as the spin-lattice relaxation process that is characterized by the time constant $T_1$. It describes the recovery of the net magnetic moment M to its equilibrium value along the axis of magnetic polarization (z). $T_2$ relaxation is associated with a decrease in spin coherence, and $T_1$ relaxation occurs due to a paramagnetic shift at the probe site and subsequent exchange of bound protons with the surrounding bulk water. The $T_1$ time constant, which is referred to as the "spin-lattice relaxation" constant or the "longitudinal relaxation" constant, is longer than $T_2$, much longer in most substances of medical interest. As with the $T_2$ constant, the difference in $T_1$ between tissues can be exploited to provide image contrast.

The reciprocals of these relaxation time constants are termed relaxation rates and denoted $R_1$ and $R_2$ where $R_1=1/T_1$ and $R_2=1/T_2$.

Contrast agents are exogenous molecules or materials that can alter the relaxation properties of tissue and induce image contrast. Contrast agents are typically paramagnetic, superparamagnetic, or ferromagnetic materials. Contrast agents are also sometimes referred to as imaging probes.

The extent to which a given contrast agent can alter the relaxation rate is termed relaxivity. Relaxivity is defined as the difference in the relaxation rate of a sample measured with and without the contrast agent. This relaxation rate difference is then normalized to the concentration of the contrast agent. Relaxivity is expressed as a lowercase "r" with a subscript "1" or "2" which refers to either the longitudinal or transverse relaxivity respectively. For instance longitudinal relaxivity, $r_1$, is defined as $r_1=)(R_1-R_1^\circ/C$ where $R_1$ is the relaxation rate in $s^{-1}$ measured in the presence of the contrast agent, $R_1^\circ$ is the relaxation rate in $s^{-1}$ measured in the absence of contrast agent, and C is the concentration in mM of the contrast agent. Relaxivity has units of $mM^{-1}s^{-1}$. For contrast agents that contain more than one metal ion, relaxivity can be expressed in terms of the metal ion concentration ('per ion' or 'ionic relaxivity') or in terms of the molecular concentration ('per molecule' or 'molecular relaxivity'). Relaxivity is an inherent property of contrast agents.

In an effort to elicit clinically-desired contrasts, MRI contrast agents have been developed that are designed to affect the relaxation periods. Not surprisingly, there are contrast agents that are used clinically to adjust $T_1$ contrast and those that are used clinically to adjust $T_2$ contrast.

$T_1$-weighted ($T_1$w) imaging provides image contrast where tissues or regions of the image are bright (increased signal intensity) when the $T_1$ of water in that region is short. One way to increase image contrast is to administer a paramagnetic complex or material based on gadolinium (Gd), manganese (Mn), or iron. This paramagnetic contrast agent shortens the $T_1$ of water molecules that it encounters and results in positive image contrast. The degree to which a given concentration of contrast agent can change $T_1$ is the relaxivity as noted above. Compounds that have higher relaxivity provide greater $T_1$w signal enhancement than compounds with low relaxivity; alternatively a high relaxivity compound can provide equivalent signal enhancement to a low relaxivity compound but at a lower concentration than the low relaxivity compound. Thus, high relaxivity compounds are desirable because they enable greater enhancement of lesions and improve diagnostic confidence; alternately, they can be used at lower doses and thus improve the safety margin of the contrast agent.

The majority of magnetic resonance contrast agents in clinical use employ the gadolinium ion in the +3 oxidation state. The manganese ion in the +2 oxidation state can also serve as a $T_1$ relaxation agent. Mangafodipir (sold under the brand name Teslascan as mangafodipir trisodium) is a contrast agent delivered intravenously to enhance contrast in magnetic resonance imaging (MRI) of the liver. It includes paramagnetic manganese (II) ions and the chelating agent fodipir (dipyridoxyl diphosphate). The manganese shortens the longitudinal relaxation time ($T_1$), making the normal tissue appear brighter in a magnetic resonance image. Mn-based agents having relaxivities as high as Gd-based contrast agents have also been described (see, e.g., Inorg Chem 43:6313-23, 2004).

One disadvantage of gadolinium magnetic resonance contrast agents is that the gadolinium ion is only stable in the +3 oxidation state under physiological conditions. Additionally, there is well-established connection between the usage gadolinium based contrast agents in renally impaired patients and a rare but serious fibrotic disorder termed nephrogenic systemic fibrosis (NSF), Further advancement of manganese based magnetic resonance contrast agents would be of tremendous utility in contrast enhanced applications. Manganese can assess numerous oxidation states under physiological conditions, with the +2 oxidation state best suited for $T_1$ and $T_2$ contrast. This can be useful in the non-invasive study of tissue redox dynamics. Manganese based contrast agents could also represent a viable alternative to gadolinium in patient groups at increased risk for NSF.

SUMMARY OF THE INVENTION

Both intracellular and extracellular redox environments are tightly regulated in healthy tissues and are closely correlated with the physiological state of the cell. However, this regulation is often disrupted during periods of cellular stress, damage or cell death. While the dynamics of local redox status play an important role in mediating various biological processes such as cell-cycle progression, immune response and wound-healing, persistent dysregulation of the extracellular redox environment has been linked to a number of pathologies including chronic inflammation, neoplastic growth, and cancer cell aggressiveness. Indeed, the role of redox in tumor biology continues to be an area of active research and is the focus of many redox-activated prodrugs that are currently in development. New imaging methods will certainly facilitate these endeavors while further advancing our basic understanding of redox dynamics in relation to disease.

There have been several redox-activated molecular imaging probes reported, each of which employs a unique mechanism of activation to address specific aspects of redox environment. Some of these probes target tissues that are hypoxic (low oxygen tension), which may result from a disruption in blood supply to the affected area or inadequate vascularization as sometimes occurs in tumors. Positron emission tomography probes $^{18}$F-fluoroisonidazole ($^{18}$F-MISO) and $^{64}$Cu-diacetyl-bis(N$^4$-methylthiosemicarbazone) ($^{64}$CU-ATSM) have been used clinically to image tumor hypoxia. Electron paramagnetic resonance (EPR) imaging and spectroscopy probes based on redox-sensitive nitroxides have proven effective at detecting the relative abundance of thiols as well as other reducing species. Magnetic resonance (MR) probes have also been reported. Examples include Gd(III) complexes in which the ligands are capable of forming reversible disulfide linkages with cysteine side-chains of extracellular proteins thereby providing an indirect view of local redox conditions, a Mn(III)-porphyrin which undergoes reduction to a Mn(II) species with higher relaxivity in hypoxic conditions, and recently, a pair of Eu(III) complexes that can be activated in the presence of β-NADH through reduction of the pendant arms of the ligands.

MR is an attractive modality to image redox dynamics as it allows the interrogation of intact, opaque organisms in three dimensions at cellular resolution (~10 μm) on high field systems and submillimeter resolution on clinical scanners. The deep tissue penetration and high resolution of MRI make it possible to directly translate findings from cells to mice to humans.

One approach to a redox-sensitive MR probe is to employ a redox-active metal ion. Gd(III), used in the majority of MR probes has only one stable oxidation state in aqueous media. Manganese, however can exist stably in a number of oxidation states depending on the ligand field. High spin Mn(II) complexes can also yield relaxivities that are comparable to the best Gd(III) complexes, and there has been recent work on Mn(II) complexes as MR probes. Herein we propose a new class of redox-activated MR probes based on the Mn(II)/Mn(III) redox couple.

The manganese ion can exist stably or metastably in different oxidation states. We have recognized an advantage of the ability of manganese to exist in different oxidation states. We show that it is possible to make ligands that bind to manganese and stabilize both the +2 and +3 oxidation states. The relaxivity of the Mn(II) complex is much higher than the Mn(III) analog. We also show that it is possible to modify the Mn-binding ligand in ways that result in one oxidation state being preferred. A benefit of such redox active complexes is their ability to act as sensors. For instance, we show that a Mn(III) complex can be reduced to the Mn(II) complex by physiological concentrations of glutathione and this in turn results in an increase in magnetic resonance signal. Thus, these complexes can act as sensors of glutathione or other biological reductants.

We also show that certain manganese complexes can change their relaxivity as pH changes. Both phenolate-O and sulfonamide-N ligands are acid dissociable and modulate the interaction of manganese with bulk water, which influences relaxivity. In our examples, relaxivity increases as pH decreases, and thus these compounds can act as sensors of pH and acidosis. The $pK_a$ values of both phenolate and sulfonamide donors are highly modular and amenable to synthetic fine tuning. Low extracellular pH is a hallmark of tissue ischemia (e.g., stroke, ischemic heart disease, renal ischemia) and many tumors.

We also developed a new ligand called CyP3A. This ligand was designed to chelate Mn(II) in a thermodynamically stable and kinetically inert fashion while allowing for direct interaction of Mn(II) with water. Kinetics data indicate that the manganese complex of CyP3A is more inert to Zn(II) transmetallation than the Mn(II) complex of CDTA (cyclohexanediaminetetraacetic acid), which represents the literature precedence exhibiting the optimal balance of the aforementioned features. The pyridyl-N donor of CyP3A is modular and affords an easy means to append another ligand donor capable of reversible occupying the coordination site occupied by water. This scaffold is ideal for potential pH-sensing applications.

Additionally, we prepared a high molecular weight (>2000 MW) multimer containing six Mn(II) chelators. The high molecular weight results in slower tumbling of the molecules in solution and can strongly enhance the Mn(II) relaxivity.

A further benefit of Mn-based contrast agents is the existence of positron emitting manganese isotopes (Mn-51 and Mn-52) which enable the use of these complexes as positron emission tomography (PET) agents. In addition, by exchange of natural Mn-55 for a PET isotope, it is possible to easily prepare dual MR-PET probes. Such probes could be employed in new hybrid MR-PET scanners where the probe could be detected using both modalities. A benefit of such an approach would be the ability to have more accurate, quantitative measures of physiological parameters such as pH, reduction potential, or ion flux.

These and other features, aspects, and advantages of the present invention will become better understood upon consideration of the following detailed description, drawings, and appended claims.

BRIEF DESCRIPTION OF THE DRAWINGS

FIG. 20E shows the relaxivity of $Na_2[Mn^{II}cycHBET]$ (2) and $Na[Mn^{II}cycHBET-NO_2]$ (25) in TRIS buffer at pH 7.4, 37° C. The slope of the line gives the relaxivity.

DETAILED DESCRIPTION OF THE INVENTION

There are several requirements for a useful redox-activated MR probe: (1) a redox half-cell potential that is accessible to biologically relevant reducing agents like glutathione (GSH); (2) a ligand that stabilizes both oxidation states such that reduction or oxidation does not result in decomposition; (3) strong signal enhancement upon activation; (4) increased signal change in the presence of pathology, i.e., a turn-on probe; and (5) kinetics that are rapid with respect to the imaging timescale.

Figure 1:
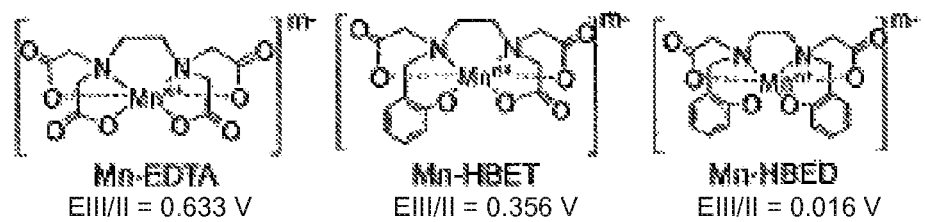
FIG. 1 shows that ligand structure strongly influences the redox potential of the $Mn^{III}/Mn^{II}$ couple. Conversion of carboxylato to phenolato donors shifts the half-cell potential by 649 mV in favor of the higher oxidation state.

A key design feature of a redox-active probe is to identify a ligand which stabilizes both oxidation states. EDTA (ethylenediaminetetraacetic acid) forms a very stable 7-coordinate Mn(II) complex with one coordinated water co-ligand, and the 2+ oxidation state is strongly favored, see FIG. 1. By contrast, changing two carboxylato donors to phenolato donors as in HBED (N,N'-di(2-hydroxybenzyl)ethylenediamine-N,N'-diacetic acid) or EHPG (N,N'-ethylene bis[2-(o-hydroxyphenyl)] glycine) strongly favors Mn(III) complexes with coordination number 6, see FIG. 1.

Figure 2:
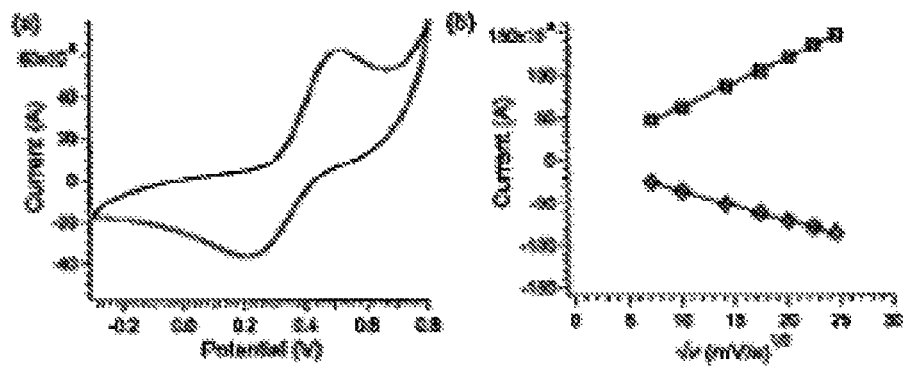
FIG. 2 shows: in (a), a cyclic voltammogram at 100 mV/s for $Mn^{II}$-HBET (25 mM) in 25 mM TRIS buffer (pH=7.4), 500 mM $KNO_3$, as the supporting electrolyte. Potentials are vs. $K_4Fe(CN)_6/K_3Fe(CN)_6$; and in (b), a Cottrell plot of the $Mn^{2+}/Mn^{3+}$ couple—$i_a$, (decreasing line) and $i_c$ (increasing line) vs. $\sqrt{v}$, where v=scan rate.

We hypothesized that HBET (hydroxybenzylethylenediamine triacetic acid) (FIG. 1) with a ligand structure that is intermediate between EDTA and HBED-containing only one phenolato donor—could potentially exhibit metastability toward either oxidation state. The preferred oxidation state of such a species would therefore be highly sensitive to changes in redox environment. To test this hypothesis, we prepared manganese complexes of HBED, HBET, and EDTA to examine how the number of phenolate groups contributes to the half-cell potentials of the Mn(III)/Mn(II) redox couple. Cyclic voltammetry of $Mn^{II}$-HBET in TRIS buffer (see FIG. 2) shows a reversible oxidation peak at 0.356 V (vs. $K_4Fe(CN)_6/K_3Fe(CN)_6$), indicating the potential for using this molecule as a redox probe. Anodic ($i_a$) and cathodic current ($i_c$) are linear with the square root of scan rate (v) over the range of 50-600 mV/s (see FIG. 2b), indicating this is a diffusion controlled process. On the other hand, $Mn^{II}$-EDTA and $Mn^{III}$-HBED display irreversible oxidation and quasi-reversible reduction peaks with half-cell potentials ($Mn^{II}/Mn^{III}$) of 0.633 V and 0.016 V respectively.

HBET (hydroxybenzylethylenediamine triacetic acid) was synthesized from reductive amination of mono BOC-protected ethylene diammine with salicylaldehyde, followed by alkylation with t-butyl bromoacetic acid, and then acid deprotection to give the free ligand in overall 45% yield. The reaction of one equivalent of ligand with $MnCl_2$ led to $Mn^{II}$-HBET in 84% isolated yield. The $Mn^{III}$-HBET complex was synthesized in 38% yield by aerial oxidation of $MnCl_2$ in the presence of one equivalent of the ligand under basic conditions, followed by RP-HPLC purification. The HBET ligand stabilizes both oxidation states to the extent that $Mn^{II}$-HBET and $Mn^{III}$-HBET can be easily separated and isolated in their pure forms using a standard RP-HPLC system. Both complexes are also stable in phosphate and carbonate buffers.

Figure 3:
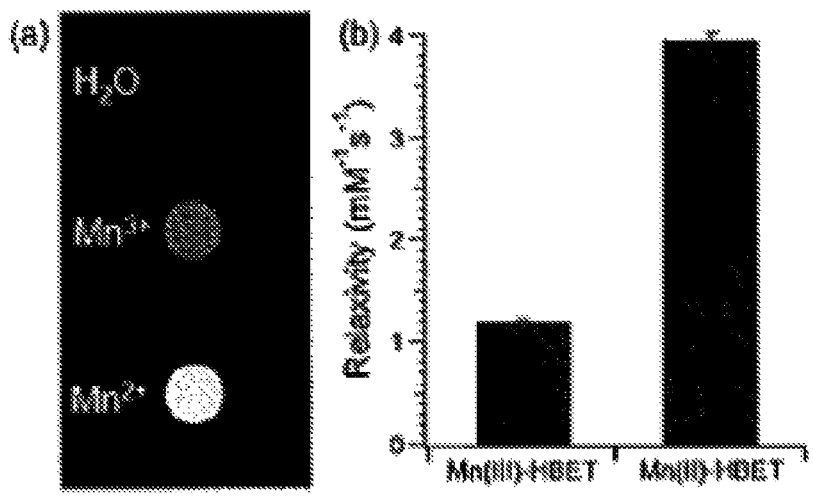
FIG. 3 shows: Left: $T_1$-weighted MR image recorded at 4.7 T of tubes containing pure water, 0.5 mM $Mn^{III}$-HBET and 0.5 mM $Mn^{II}$-HBET in pH 7.4 TRIS buffer. Right: relaxivities measured at room temperature at 4.7 T.

The $T_1$ relaxivities of the $Mn^{II}$-HBET and $Mn^{III}$-HBET complexes were measured independently at 1.4 T in Tris buffered saline (TBS: pH 7.4, 37° C.) and the values were 2.76 $mM^{-1}$ $s^{-1}$ and 1.05 $mM^{-1}$ $s^{-1}$, respectively. This difference in relaxivity is large considering that the $Mn^{III}$ state still has four unpaired electrons. In FIG. 3, we show a $T_1$-weighted MR image at 4.7 T of test tubes containing either pure water or equimolar $Mn^{III}$-HBET or $Mn^{II}$-HBET. The presence of the paramagnetic complex results in higher signal intensity compared to pure water. The higher relaxivity of $Mn^{II}$-HBET is apparent in its brighter image. $T_1$ measurements at 4.7 T revealed a 3.3-fold higher relaxivity for the reduced $Mn^{III}$-HBET form, see FIG. 3.

Figure 4:
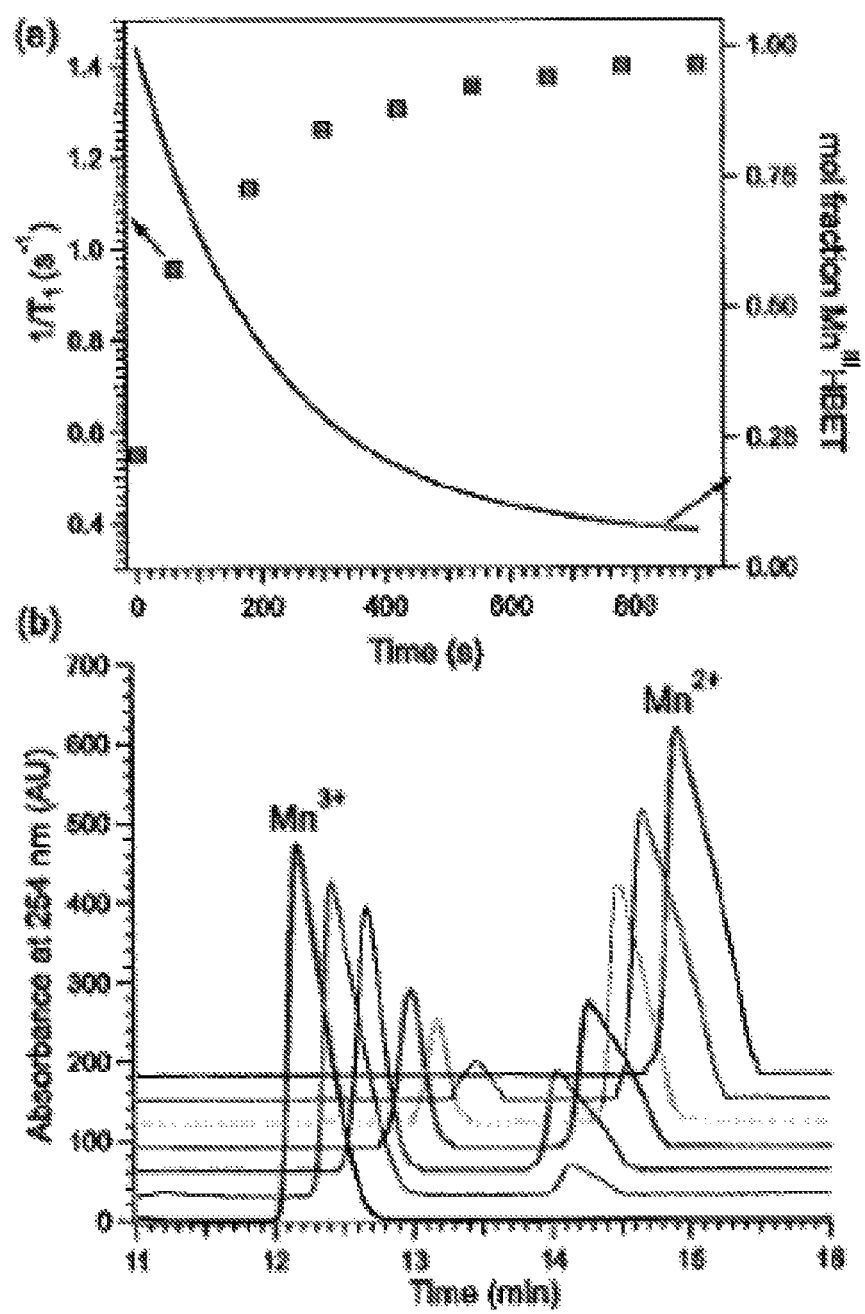
FIG. 4 shows (a) Reduction of 0.5 mM $Mn^{III}$-HBET to $Mn^{II}$-HBET by 10 mM GSH in TRIS buffer (pH 7.4, 37° C.) results in increased proton relaxation rate ($1/T_1$, left axis) and concomitant decrease in mole fraction of $Mn^{III}$-HBET (right axis) as determined by characteristic UV absorbance at 375 nm. (b) Reduction of 0.5 mM $Mn^{II}$-HBET by 1 mM GSH at 26° C. monitored by LC-MS. No long-lived intermediate species are observed in the reduction process.
Figure 5:
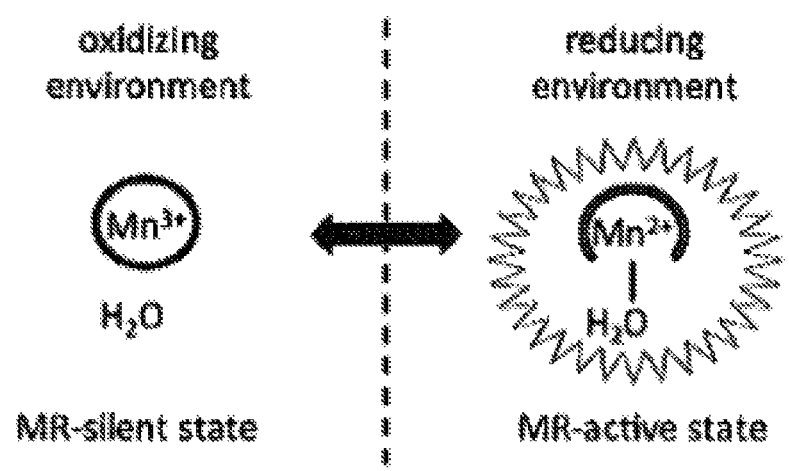
FIG. 5 shows the $Mn^{2+}/Mn^{3+}$ contrast agents in an oxidizing environment and a reducing environment.

The $Mn^{III}$-HBET complex is easily reduced to the $Mn^{II}$ state in the presence of glutathione. This conversion appears to proceed directly to the product without the accumulation of any long-lived reaction intermediates or the formation of byproducts. This is demonstrated by the timecourse experiment shown in FIG. 4b where the emergence of the $Mn^{II}$-HBET complex occurs simultaneously with the consumption of $Mn^{III}$-HBET. The progress of this reaction can also be followed in real-time by relaxometry (see FIG. 4a) using conditions relevant for clinical imaging (1.4 T, 37° C.). Since the relaxivity of the Mn(II) complex is greater than that of the Mn(III) complex, the longitudinal relaxation rate of water protons ($1/T_1$) will increase in proportion to the concentration of $Mn^{II}$-HBET in the reaction. Direct conversion of the Mn(III) complex to the Mn(II) complex is further evidenced by the observation that the rate of formation of the $Mn^{III}$-HBET species is effectively equivalent to the consumption rate of the oxidized form as measured by UV absorbance (see FIG. 4a).

A series of kinetic experiments were conducted at 37° C. (pH 7.4) to determine the empirical rate law for the reduction of $Mn^{III}$-HBET by glutathione. The $Mn^{III}$-HBET complex possesses a strong absorbance band at 375 nm ($\epsilon=1.38 \times 10^3$ $M^{-1}$ $cm^{-1}$) in water that is not present in the UV spectrum of the $Mn^{II}$-HBET complex. This feature allowed us to easily monitor the reduction of $Mn^{III}$-HBET over time. We measured initial reaction rates at three different glutathione concentrations (5 mM, 10 mM and 20 mM). For each glutathione concentration, the reaction was performed at four different initial concentrations of $M^{III}$-HBET (0.3 mM, 0.4 mM, 0.5 mM and 0.6 mM). Based on these experiments, we determined that the reaction was first-order in both [GSH] and [$Mn^{III}$-HBET] with an overall second-order rate constant of $(3.8 \pm 0.3) \times 10^{-1}$ $M^{-1}s^{-1}$.

The kinetic properties of any activatable probe are extremely important when considering its application in biomedical imaging. In the case of a redox-activated probe, conversion to the activated state must occur efficiently within a physiologically relevant redox range and should also be rapid with respect to the rate of probe washout. Concentrations of reduced glutathione within the cell are typically 1-10 mM. In that range, the half-life of the $Mn^{III}$-HBET complex is roughly 3 to 30 minutes. By comparison, the half-life in blood plasma—where glutathione levels are approximately three orders of magnitude lower—would be greater than one week. Therefore, we expect that probe activation will primarily be limited to regions where the normal mechanisms responsible for regulating extracellular redox have been severely impaired or overwhelmed.

In conclusion, the $Mn^{III}/Mn^{II}$-HBET redox couple satisfies a number of the key criteria required of a useful probe for redox imaging. The redox half-cell potential is accessible to biologically relevant reducing agents like glutathione; it displays good signal enhancement upon conversion to the MR-active state; and the activation kinetics are rapid with respect to the imaging timescale. Glutathione kinetic studies confirm that the reduction is fast in the presence of physiological glutathione concentrations. This system is extremely well behaved and the interconversion between the two oxidation states occurs via a simple and reversible one-electron process. Cyclic voltammetry confirms that this is a reversible process. Furthermore, we note that the HBET ligand could be readily modified with appropriate aryl substituents to tune the redox potential, or to incorporate a moiety that imparts specific biological targeting, opening up new avenues in molecular MR imaging.

In one example embodiment of the invention, the contrast agent is used in a diagnostic imaging technique such as magnetic resonance imaging (MRI), and/or concurrent MRI and positron emission tomography (PET). A "subject" is a mammal, preferably a human.

The form in which the contrast agent is administered to the subject is not critical. For example, the contrast agent of the invention can be administered directly to tissue being diagnostically imaged, to a body fluid that contacts the tissue, or to a body location from which the contrast agent can diffuse or be transported to the tissue being diagnostically imaged.

The contrast agent can be administered alone or as part of a pharmaceutically acceptable composition. The relative amounts of the contrast agent of the invention, a pharmaceutically acceptable carrier, and any additional active ingredients in a pharmaceutical composition of the invention will vary, depending upon the identity, size, and condition of the subject treated and further depending upon the route by which the contrast agent is to be administered. The contrast agent may include a targeting moiety that can target a region of interest in the subject. The targeting moiety may be selected from proteins, enzymes, peptides, antibodies, and drugs. A contrast agent of the invention, optionally comprising other pharmaceutically active compounds, can be administered to a subject parenterally, for example, intravenously, intramuscularly, subcutaneously, intracerebrally or intrathecally.

One non-limiting example embodiment of the invention is a contrast agent for magnetic resonance imaging. The contrast agent comprises a compound of Formula (I):

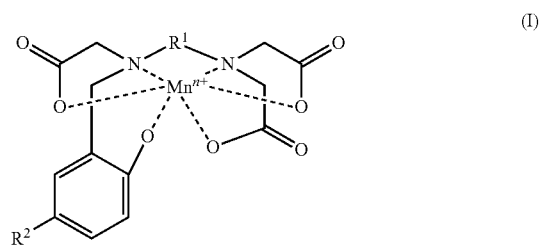

(I)

or a pharmaceutically acceptable salt of the compound, or a positional isomer of the compound wherein $R^2$ is attached to a different carbon on the benzene ring, wherein $R^1$ is selected from the group consisting of substituted or unsubstituted alkylene, substituted or unsubstituted cycloalkylene, substituted or unsubstituted heterocycloalkylene, substituted or unsubstituted arylene, substituted or unsubstituted heteroarylene, dialkylene arene, and dialkylene heteroarene, wherein $R^2$ is selected from the group consisting of hydrogen, alkyl, alkenyl, alkynyl, cycloalkyl, heterocycloalkyl, aryl, heteroaryl, halo, cyano, nitro, hydroxy, and alkoxy, wherein n is 2 or 3, and wherein the compound optionally includes a water coordinated to Mn when n is 2.

In one example embodiment of the contrast agent, the compound has the Formula (II):

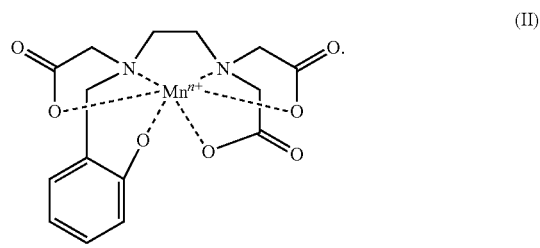

(II)

In another example embodiment of the contrast agent, the compound has the Formula (III):

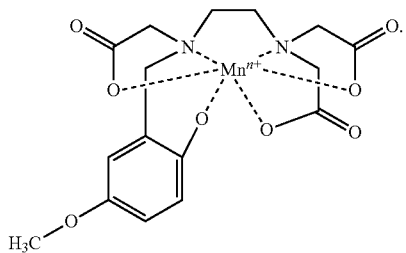

(III)

In another example embodiment of the contrast agent, the compound has the Formula (IV):

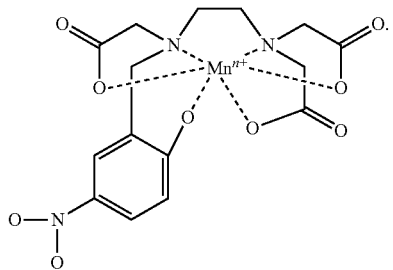

(IV)

In another example embodiment of the contrast agent, the compound has the Formula (V):

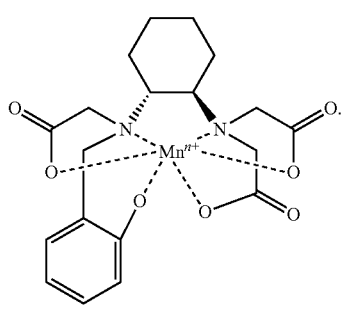

(V)

In another example embodiment of the contrast agent, the compound has the Formula (Va):

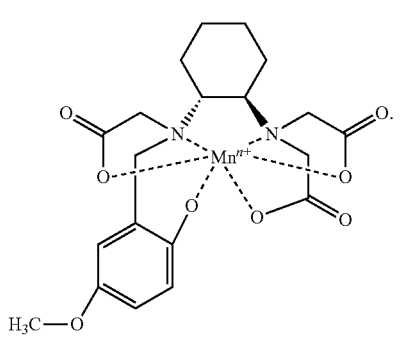

(Va)

In another example embodiment of the contrast agent, the compound has the Formula (Vb):

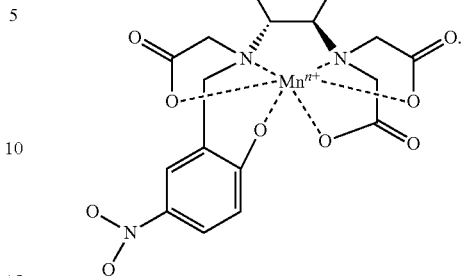

(Vb)

In another example embodiment of the contrast agent, $R^1$ is ethylene. In another example embodiment of the contrast agent, $R^2$ is methoxy. In another example embodiment of the contrast agent, $R^2$ is nitro. In another example embodiment of the contrast agent, $R^1$ is cyclohexylene. In another example embodiment of the contrast agent, at least one of $R^1$ and $R^2$ comprises a targeting moiety that can target a region of interest in a subject. The targeting moiety can be selected from proteins, enzymes, peptides, antibodies, and drugs. In another example embodiment of the contrast agent, Mn is a positron emitting manganese isotope. In an example embodiment of the contrast agent, the contrast agent has a higher relaxivity when n=2. The compound may be convertible in vivo by a biological reducing agent (e.g., glutathione) from the Formula (I) wherein n=3 to the Formula (I) wherein n=2. Alternatively, the contrast agent may be included in a pharmaceutically acceptable carrier which also includes a reducing agent for reducing the compound from the Formula (I) wherein n=3 to the Formula (I) wherein n=2.

Another non-limiting example embodiment of the invention is a contrast agent for magnetic resonance imaging. The contrast agent comprises a compound of Formula (VI):

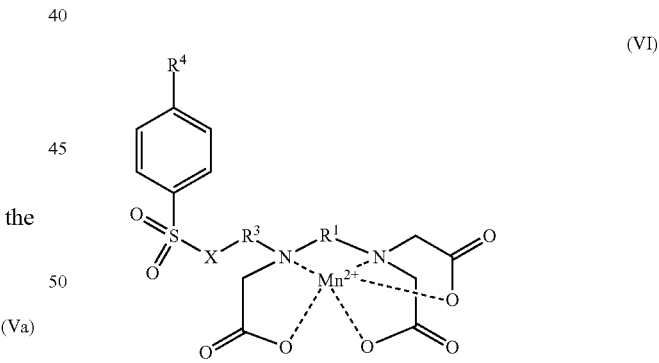

(VI)

or a pharmaceutically acceptable salt of the compound, or a positional isomer of the compound wherein $R^4$ is attached to a different carbon on the benzene ring, wherein $R^1$ is selected from the group consisting of substituted or unsubstituted alkylene, substituted or unsubstituted cycloalkylene, substituted or unsubstituted heterocycloalkylene, substituted or unsubstituted arylene, substituted or unsubstituted heteroarylene, dialkylene arene, and dialkylene heteroarene, wherein $R^3$ is selected from the group consisting of substituted or unsubstituted alkylene, substituted or unsubstituted cycloalkylene, substituted or unsubstituted heterocycloalkylene, substituted or unsubstituted arylene, substituted or unsubstituted heteroarylene, dialkylene arene, and dialkylene heteroarene, wherein $R^4$ is selected from the group consisting of hydrogen, alkyl, alkenyl, alkynyl, cycloalkyl, heterocycloalkyl, aryl, heteroaryl, halo, cyano, nitro, hydroxy, and alkoxy, wherein X is N or NH, wherein the compound optionally includes a water coordinated to Mn when X is NH, and wherein X is coordinated to Mn when X is N.

In an example embodiment of the contrast agent, the compound has the Formula (VII):

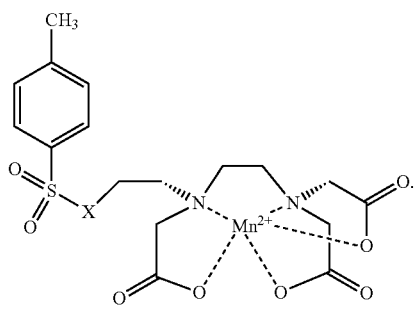

(VII)

In another example embodiment of the contrast agent, the compound has the Formula (VIII):

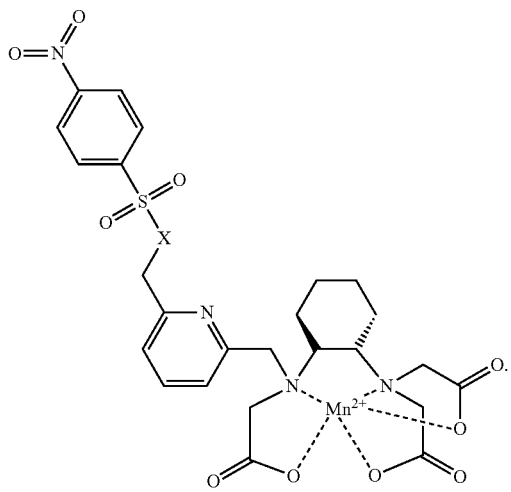

(VIII)

When the contrast agent is exposed to an environment of changing pH, the relaxivity increases when pH decreases. In another example embodiment of the contrast agent, at least one of $R^1$ and $R^4$ comprises a targeting moiety that can target a region of interest in a subject. The targeting moiety can be selected from proteins, enzymes, peptides, antibodies, and drugs. Mn can be a positron emitting manganese isotope.

In another example embodiment of the contrast agent, the compound has the Formula (IX):

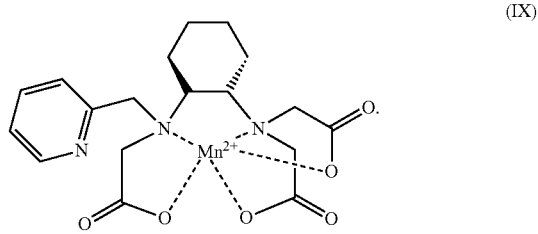

(IX)

Mn can be a positron emitting manganese isotope.

In another example embodiment of the contrast agent, the compound has the Formula (X):

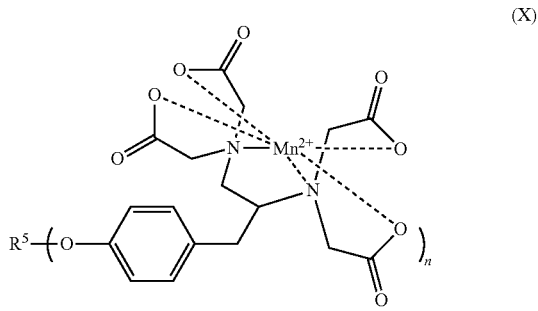

(X)

or a pharmaceutically acceptable salt of the compound, wherein $R^5$ is a core structure, and wherein n is an integer from 1 to 12. The core structure can be any atom or group of atoms capable of forming one or more ether groups with structure within the ( ) of Formula (X). $R^5$ can be a cyclic backbone. $R^5$ can be a phosphazene. In one embodiment, $R^5$ is a $N_3P_3$. In one embodiment, n is 6. Mn can be a positron emitting manganese isotope.

In another example embodiment of the contrast agent, the compound has the Formula (XI):

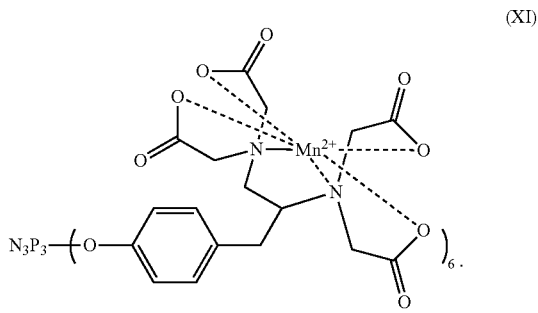

(XI)

In another example embodiment of the contrast agent, the compound has the Formula (XII):

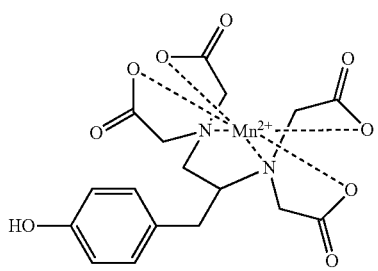

(XII)

or a pharmaceutically acceptable salt of the compound. Mn can be a positron emitting manganese isotope.

Any of the compounds of Formulas (I) to (XII) may have a per-manganese ion $r_1$ relaxivity of greater than 0.3 mM$^{-1}$s$^{-1}$, or greater than 0.5 mM$^{-1}$s$^{-1}$, or greater than 1.0 mM$^{-1}$s$^{-1}$, or greater than 1.5 mM$^{-1}$s$^{-1}$, or greater than 2.0 mM$^{-1}$s$^{-1}$, or greater than 2.5 mM$^{-1}$s$^{-1}$, or greater than 3 mM$^{-1}$s$^{-1}$, or greater than 4 mM$^{-1}$s$^{-1}$, or greater than 5 mM$^{-1}$s$^{-1}$, or greater than 6 mM$^{-1}$s$^{-1}$, or greater than 7 mM$^{-1}$s$^{-1}$, or greater than 8 mM$^{-1}$s$^{-1}$, or greater than 9 mM$^{-1}$s$^{-1}$, or greater than 10 mM$^{-1}$s$^{-1}$ as measured at pH 7.4, 37° C. and 1.4 Tesla.

The invention also provides a method for in vivo imaging of a subject. One administers to the subject the contrast agent of any of Formulas (I) to (XII). One waits a time sufficient to allow the contrast agent to accumulate at a tissue or cell site to be imaged; and the cells or tissues are imaged with a non-invasive imaging technique. Molecules in the subject that are subjected to the contrast agent have a modified longitudinal relaxation period that is reflected in the image. The non-invasive imaging technique can be magnetic resonance imaging, or positron emission tomography with magnetic resonance imaging. When the non-invasive imaging technique is positron emission tomography with magnetic resonance imaging, one administers the contrast agent having a positron emitting manganese isotope.

The invention provides a method of imaging a region of interest of a subject. One administers the contrast agent of any of Formulas (I) to (XII) to the subject. The subject is positioned in a magnet system configured to generate a polarizing magnetic field about at least a portion of a subject. A plurality of gradient coils configured to apply a gradient field to the polarizing magnetic field are energized. A radio frequency (RF) system configured to apply an excitation field to the subject is controlled to acquire magnetic resonance (MR) image data therefrom, and an image of the region of interest is reconstructed from the MR image data. When the contrast agent has a positron emitting manganese isotope, one can also use a plurality of detectors to detect gamma rays emitted from the subject and to communicate signals corresponding to the detected gamma rays. A series of medical images of the region of interest of the subject are reconstructed from the signals.

The invention also provides a method for sensing a biological reductant in a subject. One administers to the subject a contrast agent of any of Formulas (I) to (Vb) wherein n is 3 (i.e., Mn is in oxidation state 3+). One waits a time sufficient to allow the contrast agent to accumulate at a tissue or cell site to be imaged; and the cells or tissues are imaged with a non-invasive imaging technique. Cells or tissues including the biological reductant (e.g., glutathione) that are subjected to the contrast agent have a modified longitudinal relaxation period that is reflected in the image.

The invention also provides a method for detecting regions of interest having different pH levels in a subject. One administers to the subject a contrast agent of any of Formulas (I) to (IX). One waits a time sufficient to allow the contrast agent to accumulate at a tissue or cell site to be imaged; and the cells or tissues are imaged with a non-invasive imaging technique. Regions of interest in the subject having different pH levels that are subjected to the contrast agent have a modified longitudinal relaxation period that is reflected in the image. When the contrast agent is exposed to an environment of changing pH, the relaxivity increases when pH decreases.

Figure 41:
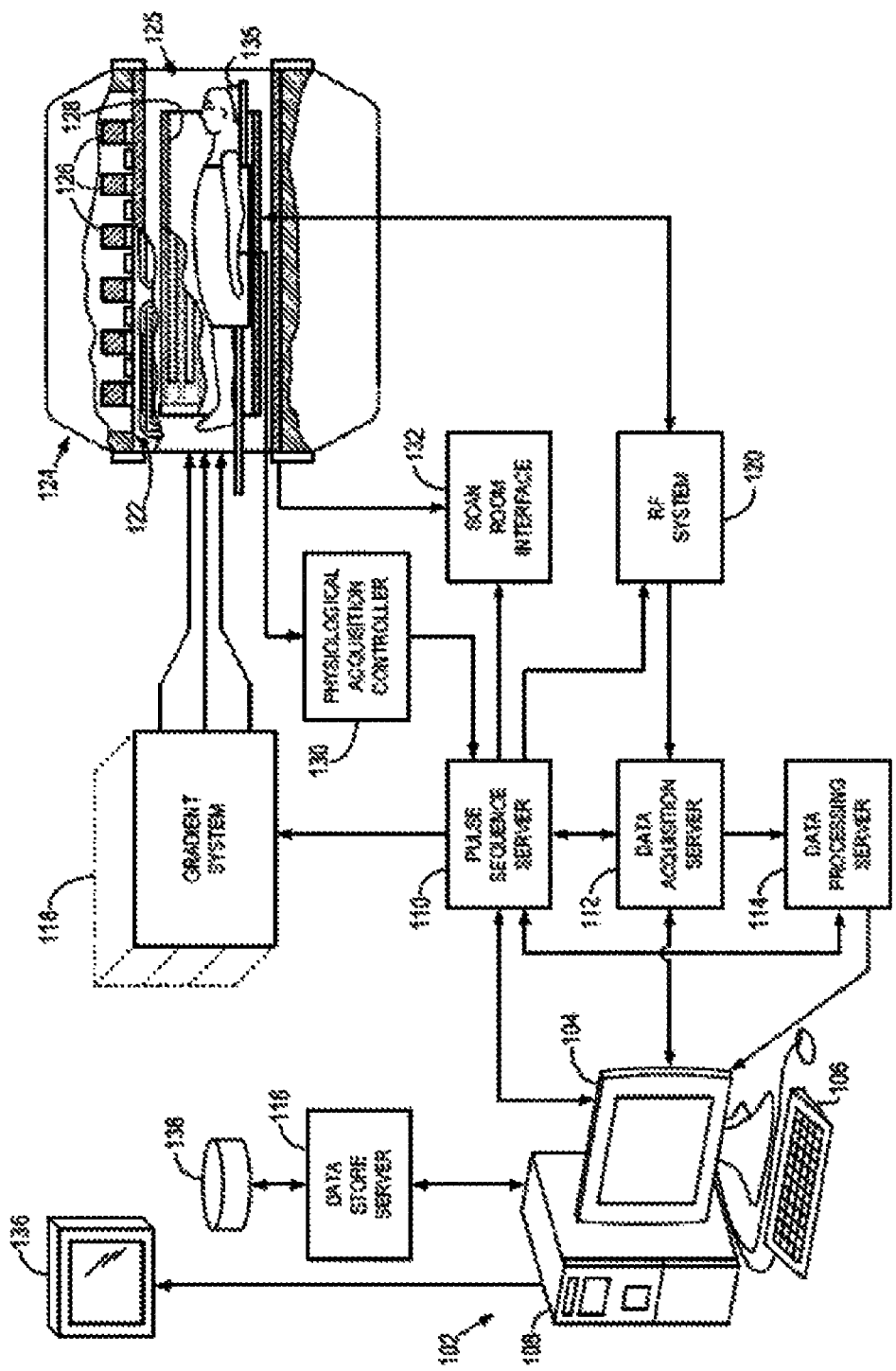
FIG. 41 is a block diagram of an example magnetic resonance imaging (MRI) system for use with a contrast agent of the present disclosure.

Referring to FIG. 41, any of the contrast agents of Formulas (I) to (XII) can be used with a magnetic resonance imaging ("MRI") system 100. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients Gx, Gy, and Gz used for position encoding MR signals. The gradient coil assembly 122 forms part of a magnet assembly 124 extending about a bore 125 formed there through and includes a polarizing magnet 126 and a whole-body RF coil 128.

RF excitation waveforms are applied to the RF coil 128, or a separate local coil (not shown), by the RF system 120 to perform the prescribed magnetic resonance pulse sequence. Responsive MR signals detected by the RF coil 128, or a separate local coil (not shown), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays.

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \qquad \text{Eqn. (1);}$$

and the phase of the received MR signal may also be determined:

$$\phi = \tan^{-1}\left(\frac{Q}{I}\right). \qquad \text{Eqn. (2)}$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110.

The data processing server 114 receives MR data from the data acquisition server 112 and processes it in accordance with instructions downloaded from the workstation 102. Images reconstructed by the data processing server 114 are conveyed back to the workstation 102 where they are stored. Real-time images are stored in a data base memory cache (not shown), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 42:
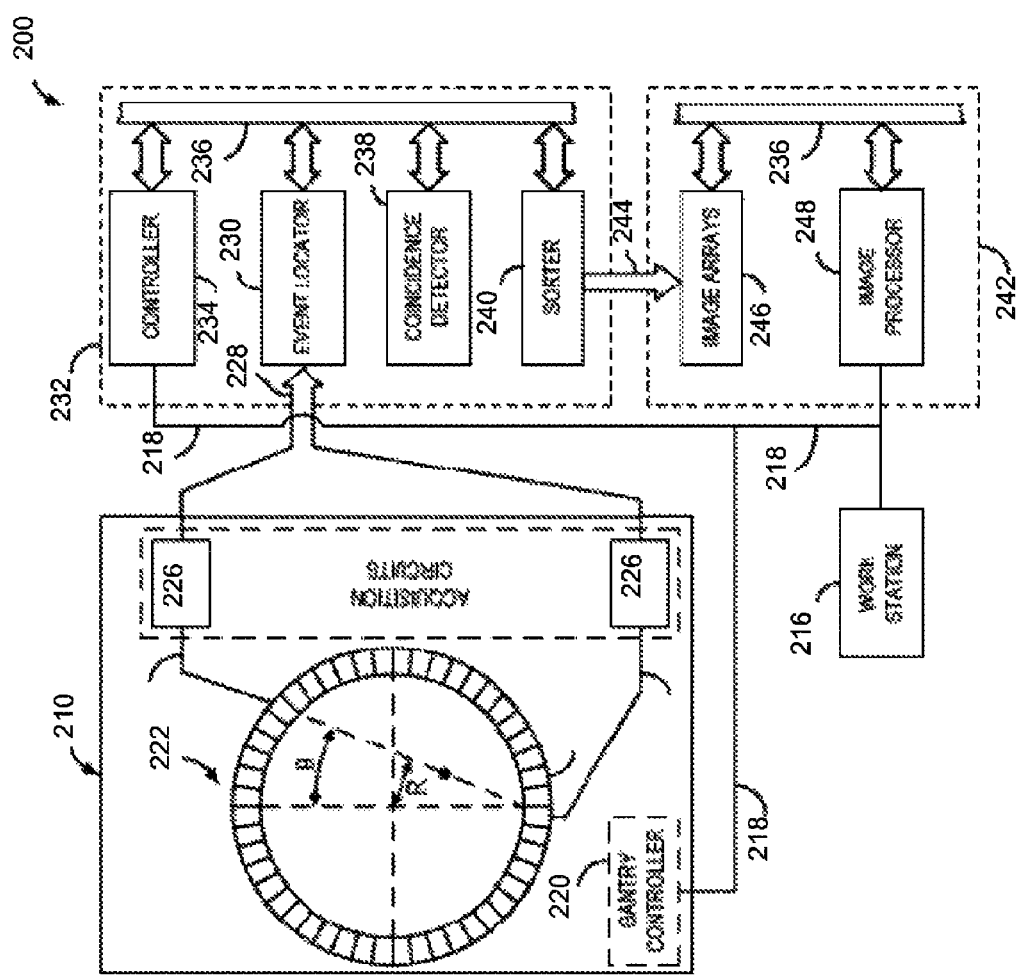
FIG. 42 is a block diagram of an example emission tomography system suitable for use with a contrast agent of the present disclosure.

FIG. 42 depicts a PET system 200 that can be used in the method of present invention along with the MRI system 100. The PET system 200 includes an imaging hardware system 210 that includes a detector ring assembly 212 about a central axis, or bore 214. An operator work station 216 including a commercially-available processor running a commercially-available operating system communicates through a communications link 218 with a gantry controller 220 to control operation of the imaging hardware system 210.

The detector ring assembly 212 is formed of a multitude of radiation detector units 222 that produce a signal responsive to detection of a photon on communications line 224 when an event occurs. A set of acquisition circuits 226 receive the signals and produce signals indicating the event coordinates (x, y) and the total energy associated with the photons that caused the event. These signals are sent through a cable 228 to an event locator circuit 230. Each acquisition circuit 226 also produces an event detection pulse that indicates the exact moment the interaction took place. Other systems utilize sophisticated digital electronics that can also obtain this information regarding the precise instant in which the event occurred from the same signals used to obtain energy and event coordinates.

The event locator circuits 230 in some implementations, form part of a data acquisition processing system 232 that periodically samples the signals produced by the acquisition circuits 226. The data acquisition processing system 232 includes a general controller 234 that controls communications on a backplane bus 236 and on the general communications network 218. The event locator circuits 230 assemble the information regarding each valid event into a set of numbers that indicate precisely when the event took place and the position in which the event was detected. This event data packet is conveyed to a coincidence detector 238 that is also part of the data acquisition processing system 232.

The coincidence detector 238 accepts the event data packets from the event locator circuit 230 and determines if any two of them are in coincidence. Coincidence is determined by a number of factors. First, the time markers in each event data packet must be within a predetermined time window, for example, 0.5 nanoseconds or even down to picoseconds. Second, the locations indicated by the two event data packets must lie on a straight line that passes through the field of view in the scanner bore 214. Events that cannot be paired are discarded from consideration by the coincidence detector 238, but coincident event pairs are located and recorded as a coincidence data packet. These coincidence data packets are provided to a sorter 240. The function of the sorter in many traditional PET imaging systems is to receive the coincidence data packets and generate memory addresses from the coincidence data packets for the efficient storage of the coincidence data. In that context, the set of all projection rays that point in the same direction (θ) and pass through the scanner's field of view (FOV) is a complete projection, or "view". The distance (R) between a particular projection ray and the center of the FOV locates that projection ray within the FOV. The sorter 240 counts all of the events that occur on a given projection ray (R, θ) during the scan by sorting out the coincidence data packets that indicate an event at the two detectors lying on this projection ray. The coincidence counts are organized, for example, as a set of two-dimensional arrays, one for each axial image plane, and each having as one of its dimensions the projection angle θ and the other dimension the distance R. This θ by R map of the measured events is call a histogram or, more commonly, a sinogram array. It is these sinograms that are processed to reconstruct images that indicate the number of events that took place at each image pixel location during the scan. The sorter 240 counts all events occurring along each projection ray (R, θ) and organizes them into an image data array.

The sorter 240 provides image datasets to an image processing I reconstruction system 242, for example, by way of a communications link 244 to be stored in an image array 246. The image arrays 246 hold the respective datasets for access by an image processor 248 that reconstructs images. The image processing/reconstruction system 242 may communicate with and/or be integrated with the work station 216 or other remote work stations.

The invention is further illustrated in the following Examples which are presented for purposes of illustration and not of limitation.

EXAMPLES

Example 1

Experimental

General

Materials and Instrumentation. All chemicals and solvents were purchased commercially and used without further purification. NMR spectra were recorded on either 500 MHz or 400 MHz Varian spectrometers. Chemical shifts are reported in δ (ppm). For $^1H$ and $^{13}C$ NMR spectra, the residual solvent peaks were used as internal reference, except for the $^{13}C$ NMR of the ligand where tertbutanol was used as the internal reference.

Liquid chromatography-electrospray mass spectrometry (LC-MS) was performed using an Agilent 1100 Series apparatus with an LC/MSD trap and Daly conversion dynode detector with UV detection at 220, 254 and 280 nm. The methods used on this system are as follows: (a) Luna C18 column (100×2 mm); eluent A: $H_2O$/0.1% formic acid, B: MeCN/0.1% formic acid; gradient: 5% B to 95% B over 9 minutes; flow rate 0.8 mL/min (used for characterization of organic compounds), and (b) Kromasil C18 column (250× 4.6 mm); eluent C: 95% MeCN/5% 10 mM ammonium acetate, D: 10 mM ammonium acetate; gradient 5% C to 8% C over 14 minutes; flow rate 0.8 ml/min (used for characterization of manganese complexes). Reversed-phase semi-preparative purification was performed on a Rainin Dynamax HPLC system with UV detection at 254 nm using a Polaris C18 column. The method used for purification is as follows: The mobile phase A was 50 mM ammonium acetate buffer, pH 6.5 and mobile phase B was a mixture of 5% 50 mM ammonium acetate buffer, pH 6.5/95% MeCN. Starting from 5% B, the fraction of B increased to 8% over 23 minutes. The column was washed with 100% B for 2 minutes and then ramped to 5% B. The system was re-equilibrated at 5% B for 3 minutes. Relaxivity measurements were performed on a Bruker mq60 Minispec at 1.4 T and 37° C. Manganese concentrations were determined using an Agilent 7500a ICP-MS system. All samples were diluted with 0.1% Triton X-100 in 5% nitric acid containing 20 ppb of Lu (as internal standard). The ratio of Mn (54.94)/Lu(174.97) was used to quantify the manganese concentration. A linear calibration curve ranging from 0.1 ppb to 200 ppb was generated daily for the quantification. UV-Vis spectra were recorded on a SpectraMax M2 spectrophotometer using quartz cuvette with a 1 cm path length. Cyclic voltammetry of $Mn^{II}HBET$, $Mn^{II}EDTA$ and $Mn^{III}HBET$ was recorded using a Nuvant EZstat pro potentiostat in TRIS buffer (pH=7.4), containing 0.5M $KNO_3$ as supporting electrolyte, at 100 mVs-1 scan rate. Glassy carbon was used as the working electrode, Ag/AgCl served as the reference electrode and Pt wire was used as the auxiliary electrode. The $K_4FeCN_6$/$K_3FeCN_6$ couple was used as the internal standard.

Relaxometric Study.

$T_1$ was measured with an inversion recovery pulse sequence taking 10 inversion times. Relaxivity was determined from the slope of a plot of $1/T_1$ vs. concentration of in TRIS buffer, pH=7.4 at 37° C. The concentration of manganese in each stock solution was determined using ICP-MS.

Figure 35:
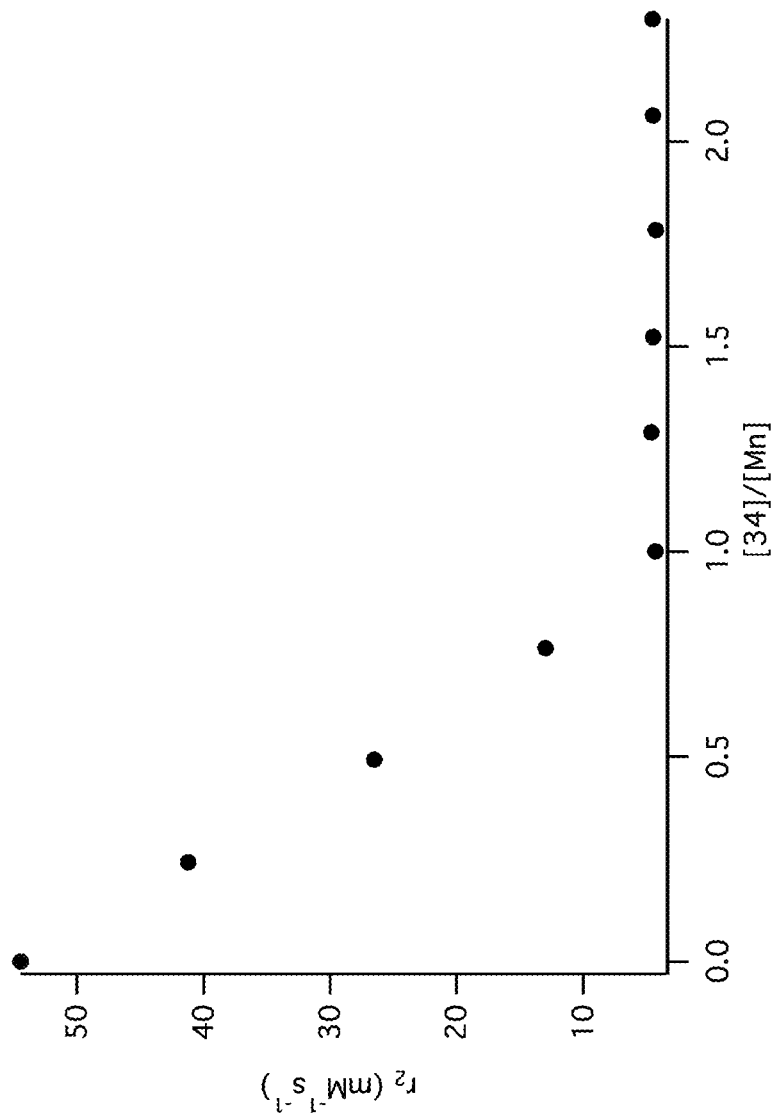
FIG. 35 shows $T_2$ plotted as a function of the ratio 33:$Mn^{2+}$ at pH 7.40.
Figure 36:
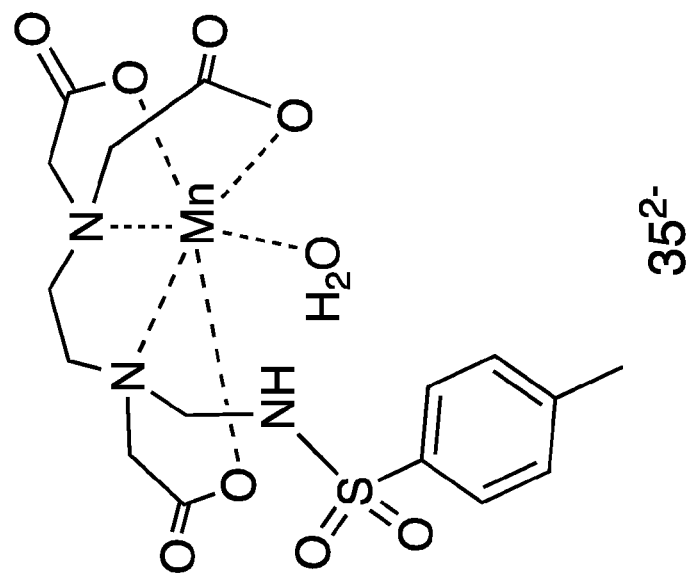
FIG. 36 shows the pH triggered interconversion between $35^{1-}$ and $35^{2-}$.
Figure 36:
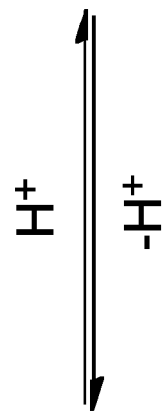
Figure 36:
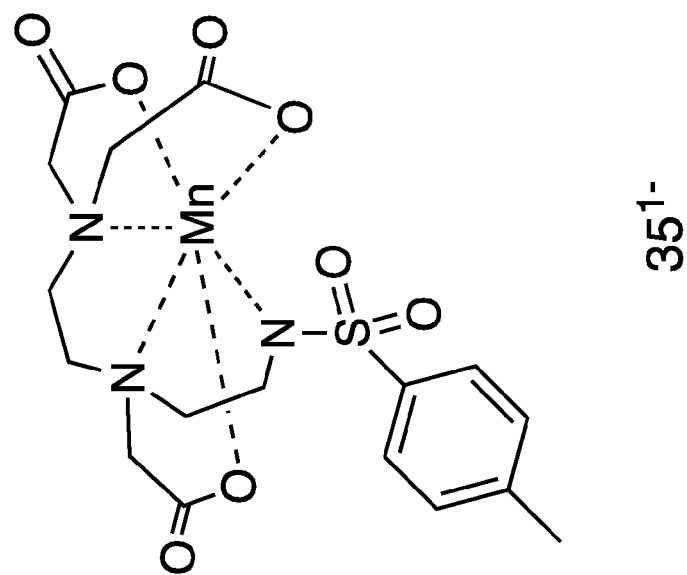
Figure 37:
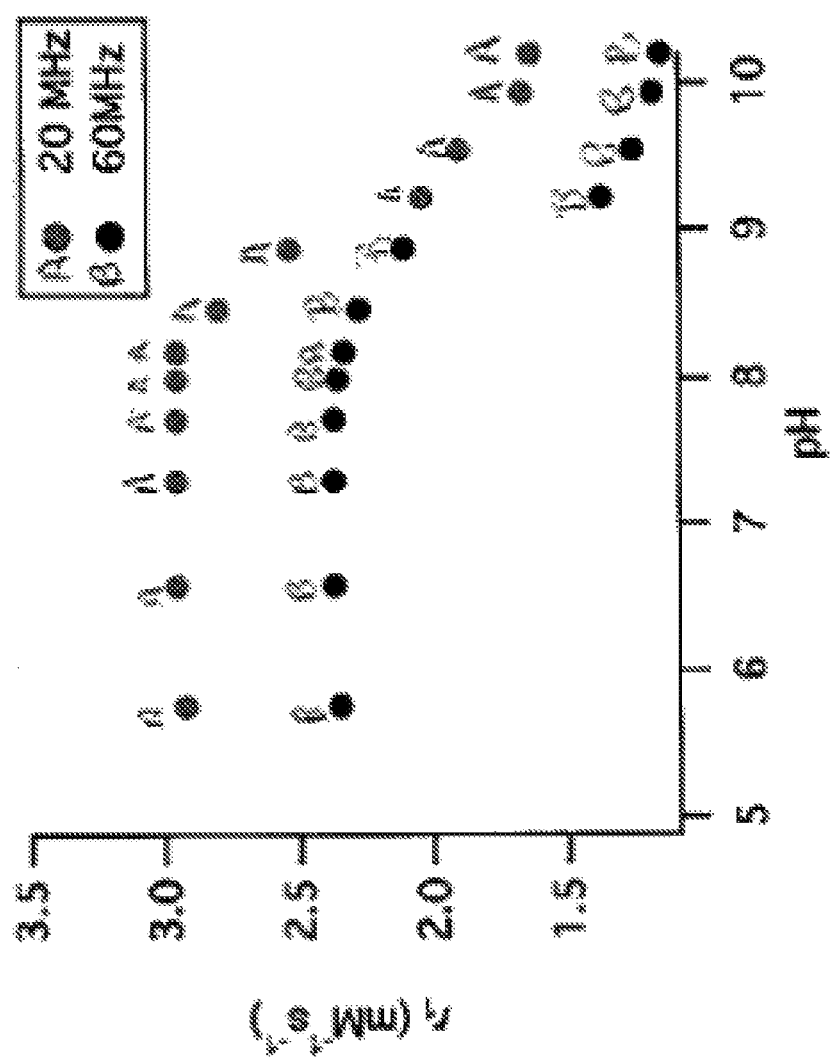
FIG. 37 shows the pH dependence of $r_1$ values of $34^{2-}/34^{1-}$ at 20 MHz (A) and 60 MHz (B) at 37° C.

Mn:Ligand Stoichiometry:

The TFA composition of the ligand species and the amount of ligand needed to fully chelate all Mn(II) in solution was determined in accordance to the following example: to 500 μL samples of 0.91 mM $MnCl_2$ in pH 7.40 buffer (25 mM TRIS) (0.45 μmol present in each), increasingly larger portions of a 1.45 mM 34 (0 to 675 μL in increments of 75 μL; 1.09 μmol present in each 75 μL portion) were added. The $T_2$ value of each sample was subsequently measured and relaxivity plotted as a ratio of ligand to metal (FIG. 35). The point of full Mn consumption was determined by the point where $r_2$ ceased to decrease with added ligand.

Figure 21:
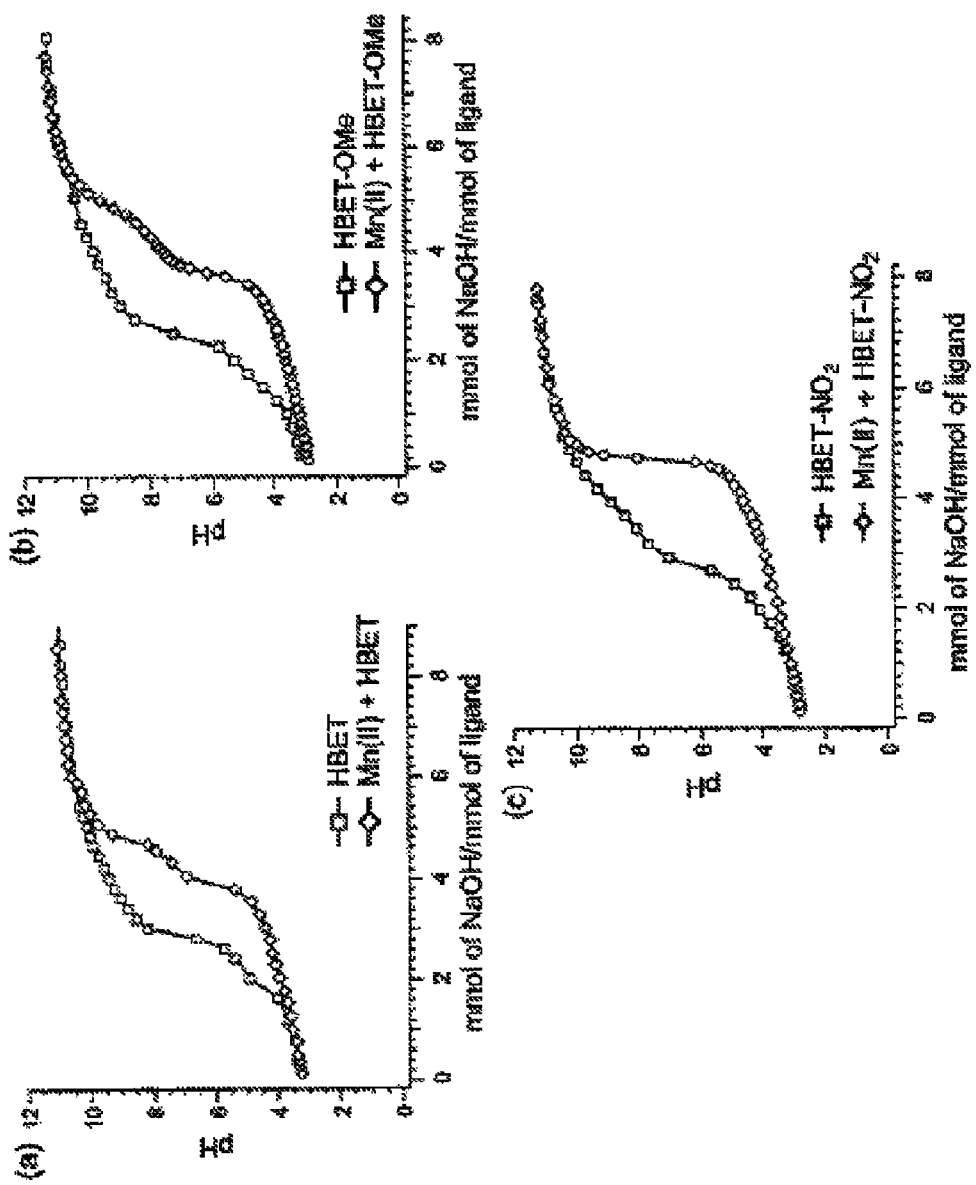
FIG. 21 shows pH-titration curves for the ligands and their corresponding manganese complexes: (a) HBET, (b) HBET-OMe and (c) HBET-$NO_2$.

To probe the speciation of the manganese complexes in solution, pH titrations of 1:1 $Mn^{2+}$:ligand were performed using a 1 N NaOH under $N_2$ atmosphere (FIG. 21).

Figure 22:
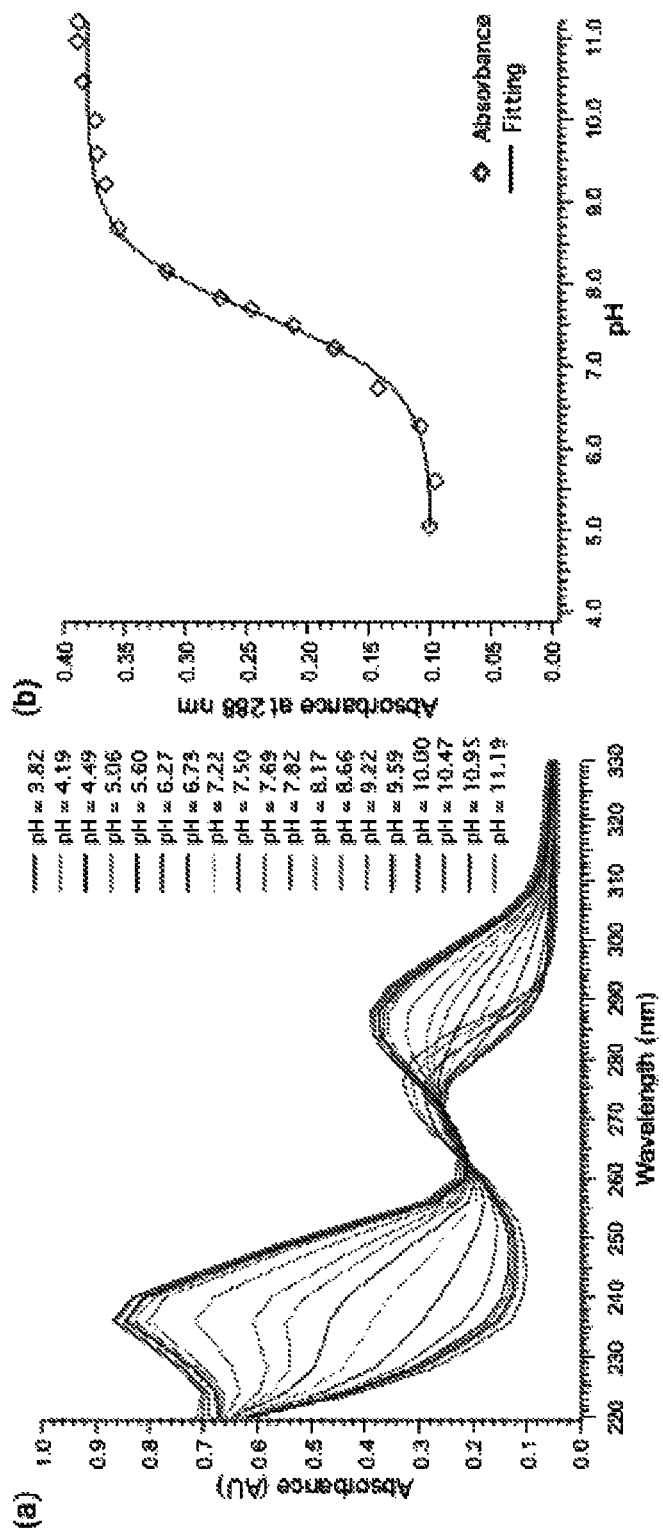
FIG. 22 shows: (a) UV spectrum of $Na_2[Mn^{II}HBET]$ (4) monitored as a function of pH. (b) Plot of absorbance at 288 nm as a function of pH. An increase in absorbance corresponds to phenol deprotonation and this can be fit to give a $pK_a$ of 7.64 for this ionization of the phenol.
Figure 23:
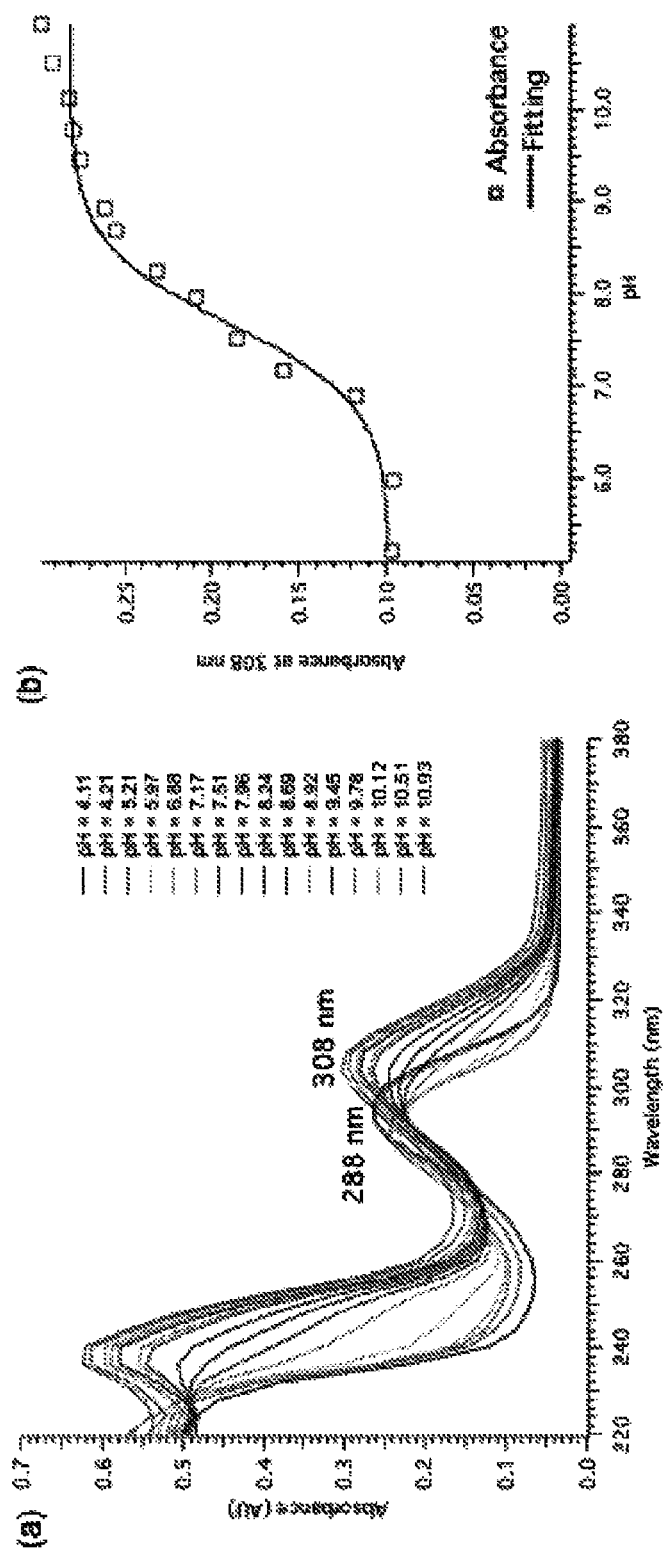
FIG. 23 shows: (a) UV spectrum of $Na_2[Mn^{II}HBET-OMe]$ (9) monitored as a function of pH. (b) Plot of absorbance at 308 nm as a function of pH. An increase in absorbance corresponds to phenol deprotonation and this can be fit to give a $pK_a$ of 7.91 for this ionization of the phenol.
Figure 24:
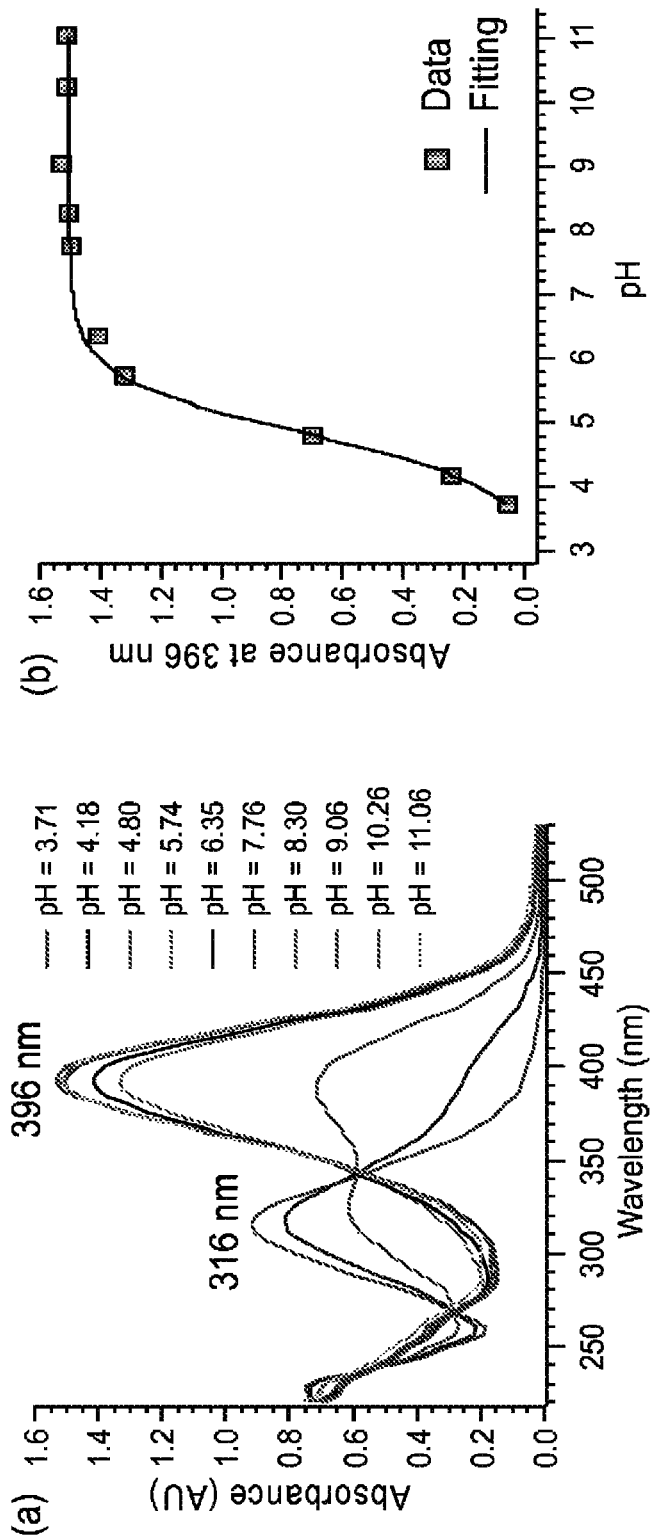
FIG. 24 shows: (a) UV spectrum of 1:1 $Mn^{II}$:HBET-$NO_2$ monitored as a function of pH. (b) Plot of absorbance at 396 nm as a function of pH. An increase in absorbance corresponds to phenol deprotonation and this can be fit to give a $pK_a$ of 4.84 for this ionization of the phenol.
Figure 25:
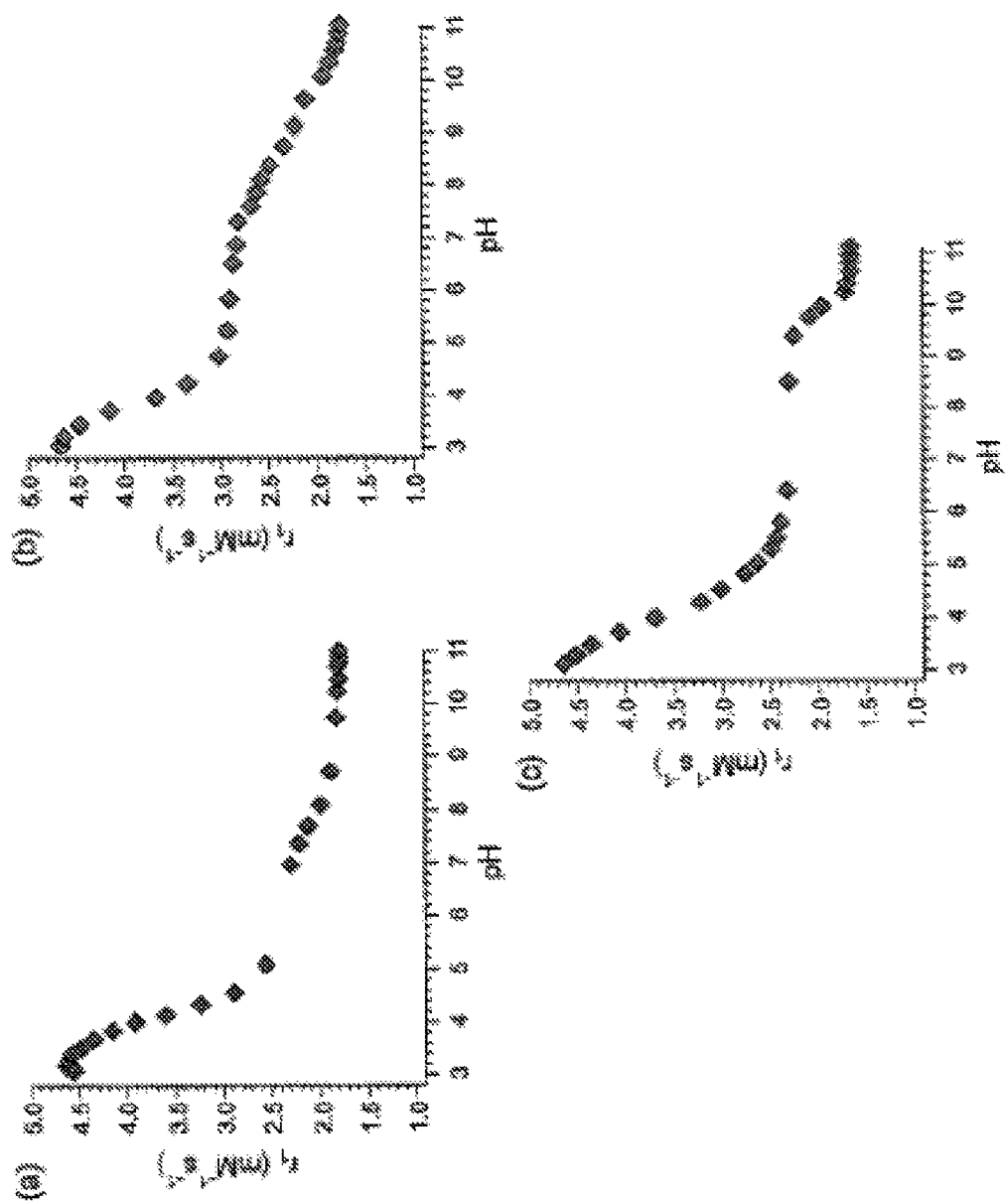
FIG. 25 shows the change of relaxivity for 1:1 $Mn^{2+}$: ligand titration plotted as a function of pH for (a) HBET, (b) HBET-OMe and (c) HBET-$NO_2$.
Figure 26:
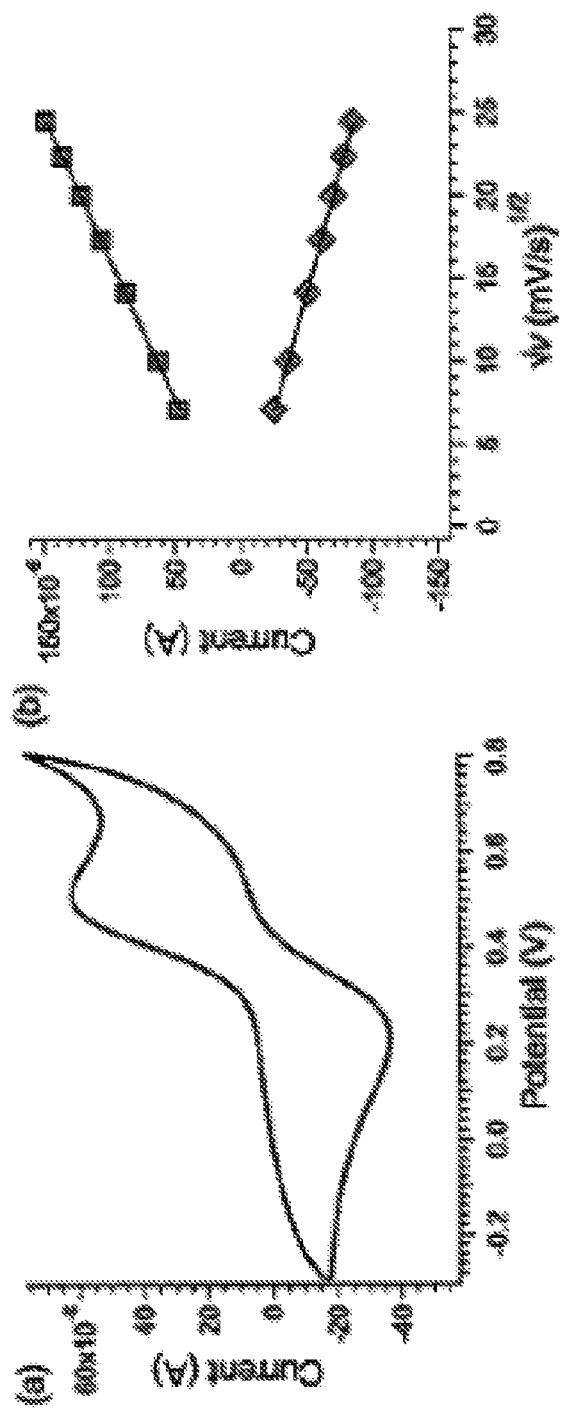
FIG. 26 shows (a) a cyclic voltammogram at 100 mV/s for $Mn^{II}$-HBET in 25 mM TRIS buffer (pH=7.4), 500 mM $KNO_3$ as the supporting electrolyte. Potentials are vs. $K_4Fe(CN)_6/K_3Fe(CN)_6$. (b) a Cottrell plot of $Mn^{2+}/Mn^{3+}$ couple—$i_a$ (decreasing line) and $i_c$ (increasing line) vs. $\sqrt{v}$, where v=scan rate.
Figure 27:
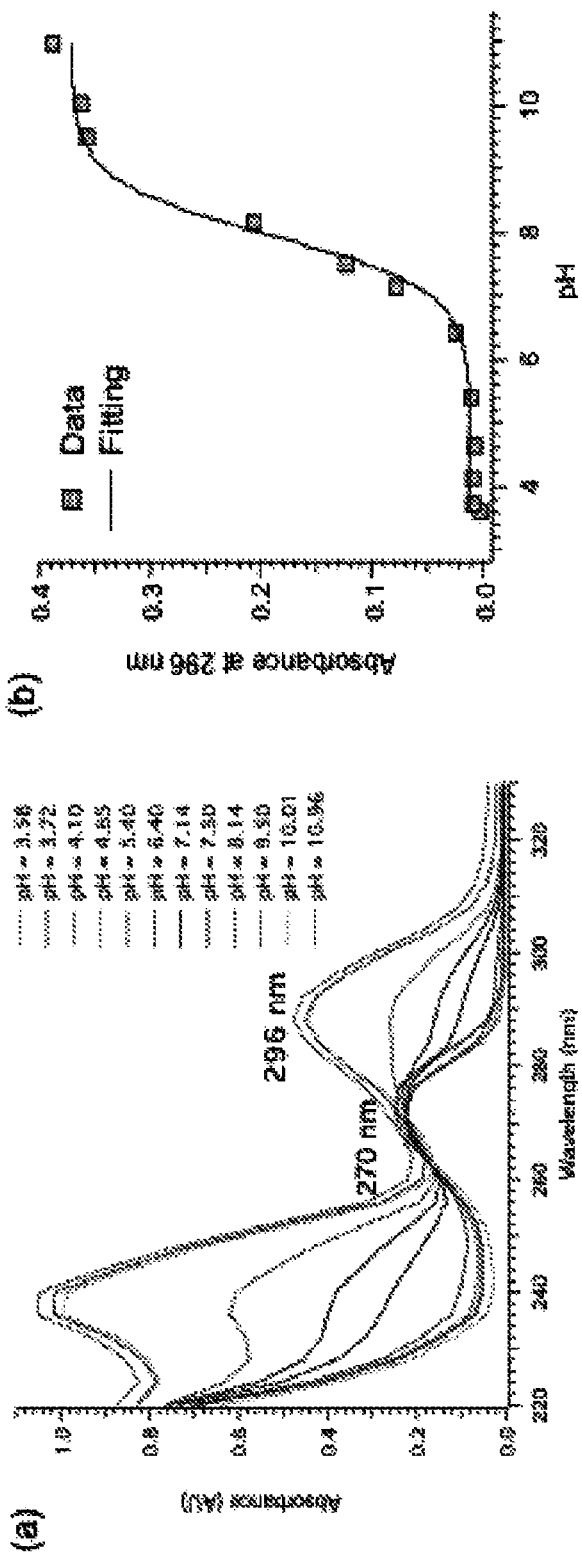
FIG. 27 shows in (a) UV spectrum of $Na_2[Mn^{II}cycHBET]$ (20) monitored as a function of pH; and in (b) Plot of absorbance at 296 nm as a function of pH. An increase in absorbance corresponds to phenol deprotonation and this can be fit to give a $pK_a$ of 7.95 for this ionization of the phenol.

To determine the species that exists in these two pH ranges the UV spectrum as a function of pH was monitored (see FIGS. 22-24). The deprotonation of the phenol moiety to form phenoxide ion results in characteristic UV bands that indicates that Mn-HBET and Mn-HBET-OMe are protonated at lower pH and the protonation occurs at the phenol. As the pH is increased the phenol deprotonates and coordinates to the manganese center.

The speciation in solution was also monitored by measuring the relaxivity of water protons at 1.4 T. FIG. 24 shows the change of relaxivity vs. pH for the three ligand systems. The change in the relaxivity is consistent with the pH dependent speciation as observed in the UV studies.

Kinetic Experiments for the Reduction Reaction.

This series of kinetic experiments were conducted at 37° C. (pH 7.4) to determine the empirical rate law for the reduction of $Mn^{III}$-HBET by glutathione. The $Mn^{III}$HBET complex possesses a strong absorbance band at 375 nm (c=1.38×103 $M^{-1}$ $cm^{-1}$) in water that is not present in the UV spectrum of the $Mn^{III}$-HBET complex. This feature was used to monitor the reduction of $Mn^{II}$-HBET over time. Initial reaction rates were measured at a three different glutathione concentrations (5 mM, 10 mM and 20 mM). Additionally, for each glutathione concentration, the reaction was performed at four different initial concentrations of $Mn^{III}$-HBET (0.3 mM, 0.4 mM, 0.5 mM and 0.6 mM). By using a large excess of glutathione in these experiments, we found the reaction behaved pseudo first-order with respect to the $Mn^{II}$-HBET complex as expressed in equation S1.

$$[Mn^{III}HBET]_t = [Mn^{III}HBET]_o \cdot e^{-k_{obs} \cdot t} \quad \text{(eq. S1)}$$

Figure 14:
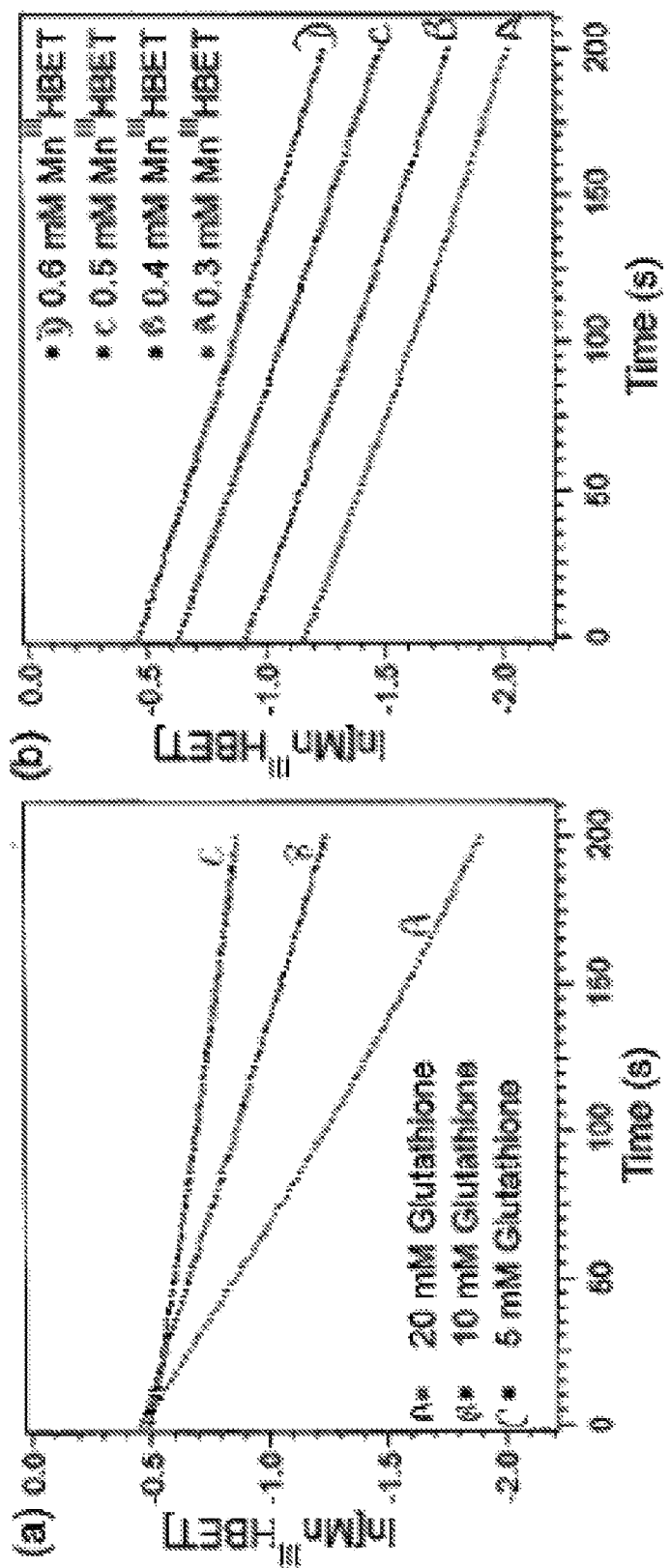
FIG. 14 shows that in the presence of a large excess of reduced glutathione, the redox reaction behaves pseudo first order with respect to $[Mn^{III}$-HBET$]$. The slope of each line is equal to $-k \cdot [GSH]$ (see equation S1 below). a.) The concentration of glutathione is varied in each reaction while the initial concentration $Mn^{III}$-HBET (0.6 mM) is not. b.) The initial $Mn^{III}$-HBET concentration is varied while the glutathione concentration (10 mM) is held constant.
Figure 15:
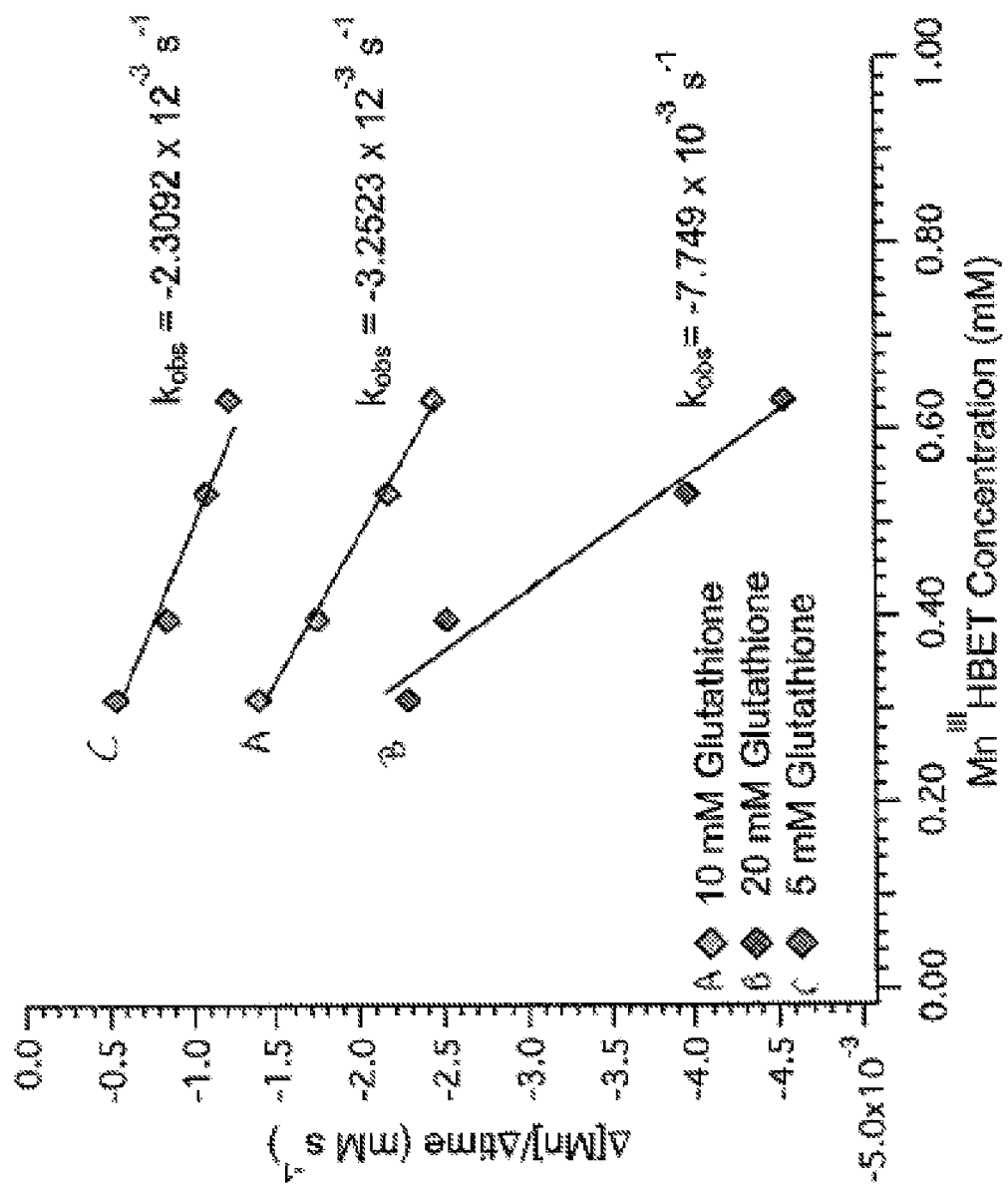
FIG. 15 shows a plot of initial rate for $Mn^{III}$HBET reduction as a function $Mn^{III}$HBET concentration at three different glutathione concentrations. The slope of each line ($k_{obs}$) is equal to $-k \cdot [GSH]$ (see equation S1 below).
Figure 16:
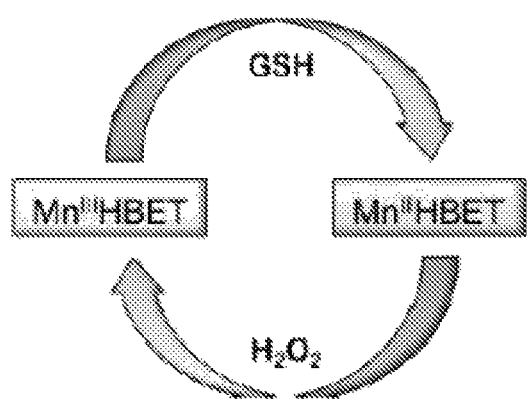
FIG. 16 shows the interconversion between the two oxidation states with reducing agent (GSH) and oxidizing agent ($H_2O_2$).
Figure 17:
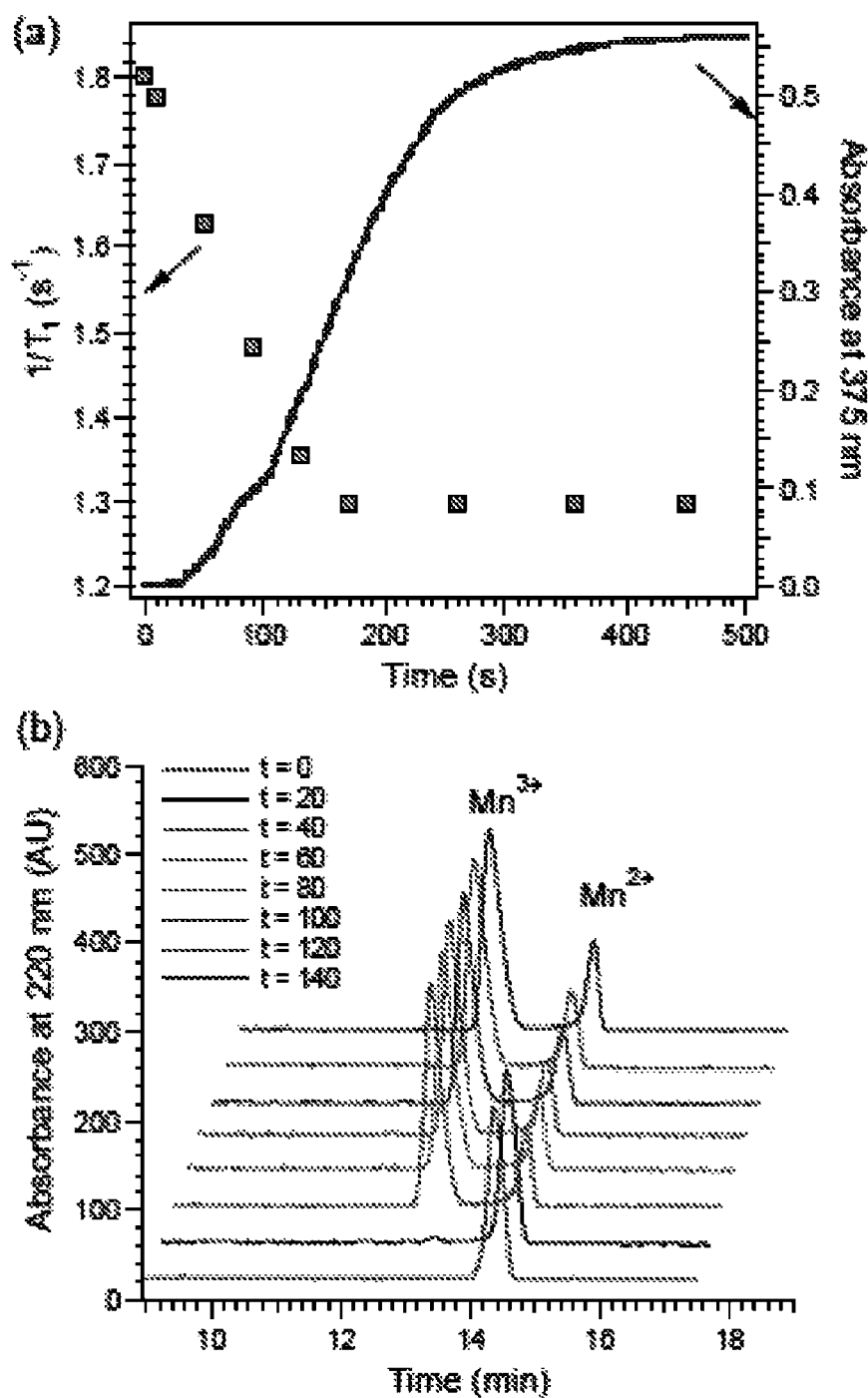
FIG. 17 shows in (a), oxidation of 0.5 mM $Mn^{II}$-HBET to $Mn^{III}$-HBET with 1 mM $H_2O_2$ in TRIS buffer (pH 7.4, 37° C.) followed by relaxivity measurements (left axis) and UV-Vis spectroscopy, where the increase in the UV absorbance at 375 nm indicates the formation of $Mn^{III}$HBET as a function of time (right axis); and in (b), oxidation of 0.5 mM $Mn^{II}$-HBET by 1 mM $H_2O_2$ at 26° C. monitored by LC-MS.
Figure 18:
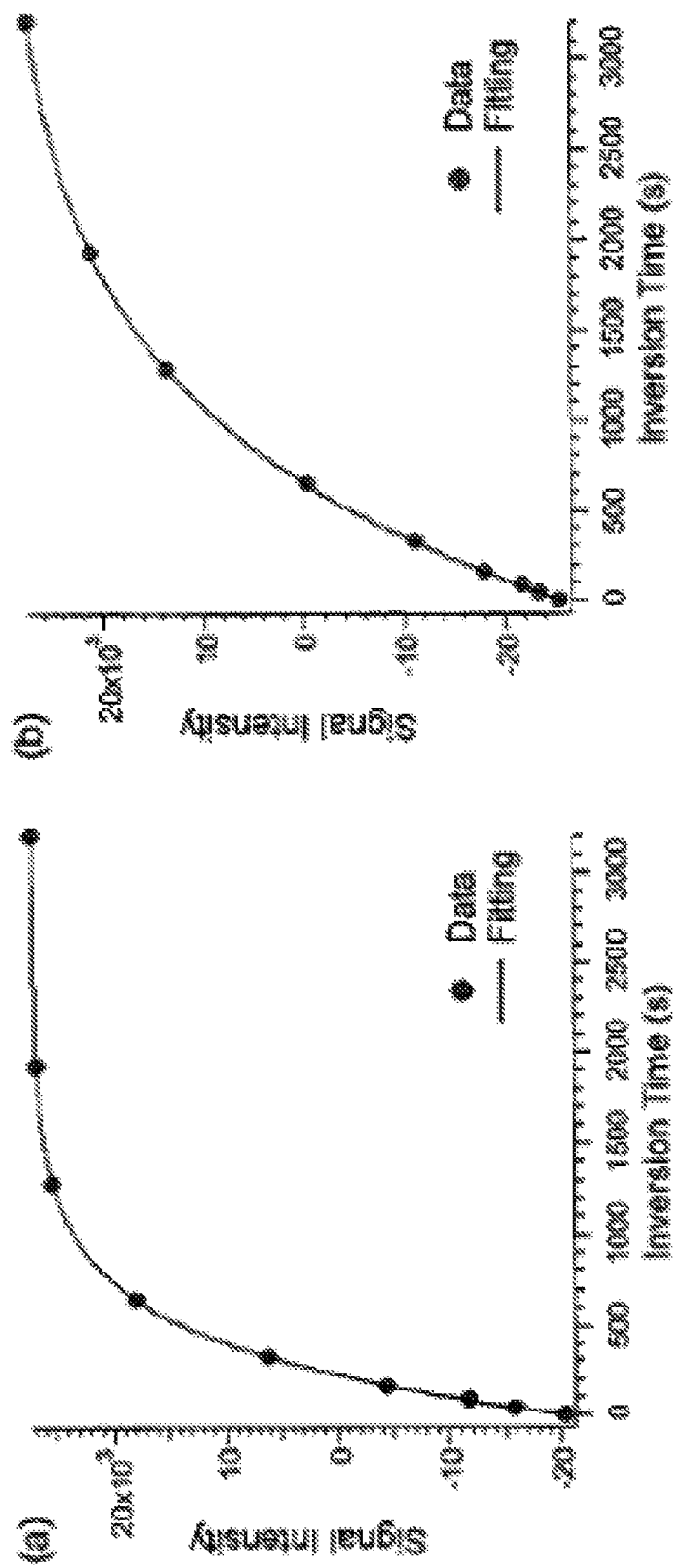
FIG. 18 shows representative plots of signal intensity vs. inversion time (TI) for (a) 0.5 mM $Mn^{II}$HBET and (b) 0.5 mM $Mn^{III}$HBET in TRIS buffer (pH=7.4). Note the faster signal recovery for $Mn^{II}$-HBET indicating a shorter $T_1$ and higher relaxivity than $Mn^{III}$-HBET.

Here, the observed rate constant ($k_{obs}$) is simply the product of the actual rate constant (k) and [GSH], t is time, and the subscripts 't' and 'o' refer to the concentration at time 't' or the initial concentration, respectively. FIG. 14 shows two sets of kinetic experiments in which we have plotted the natural log of $[Mn^{III}-HBET]t$ as a function of time. In this way, the slope of each line is equal to $-k \cdot [GSH]$ and the intercept is $In[Mn_{III}-HBET]_o$. Based on these experiments, we determined that the reaction was first-order in both [GSH] and [$Mn^{III}$-HBET] with an overall second-order rate constant of $(3.8 \pm 0.3) \times 10^{-1} M^{-1} s^{-1}$.

Oxidation of $Mn^{II}HBET$ with Hydrogen Peroxide.

The oxidation of $Mn^{II}HBET$ with $H_2O_2$ (1 mM) in TRIS buffer (pH=7.4) was followed using UV-Vis spectroscopy, relaxivity measurements, and LC-MS. Unlike the reduction of $Mn^{III}HBET$ with glutathione, the oxidation reaction appears to reach equilibrium after 70% conversion to $Mn^{II}$-$_t$HBET as calculated from LC-MS data.

MR Imaging.

MR imaging was performed using a Bruker Biospec 4.7 T system. Three samples (~500 μL) were placed in a homemade sample holder and imaged using a volume coil. Acquisition matrix=64×256 for 0.234×0.312 $mm^2$ in-plane resolution; slice thickness=5 mm. $T_1$-weighted images were obtained with a fast low angle shot (FLASH) gradient echo sequence: TR/TE/FA=20/5.44/40° with 8 averages. $T_1$ was determined using a 2D rapid acquisition refocused echo (RARE) inversion recovery sequence: TR=3200 ms, TE=9.7 ms. Inversion times (TI): 5, 45, 85, 165, 325, 645, 1285, 1925 and 3205 ms. $T_1$ was obtained from a nonlinear least square fit of the signal intensity (SI(t)) vs. TI curve where T1, SI(0) and a are adjustable parameters, equation S2.

$$SI(t)=SI(0)[1-\alpha_t e^{TI/T1}] \qquad \text{(eq. S2)}$$

Stability of $Mn^{II}HBET$ and $Mn^{III}HBET$ Complexes

The stability of the manganese complexes were measured in different buffers using concentrations similar to those found in the blood plasma (1 mM phosphate buffer, 25 mM sodium bicarbonate buffer and 0.1 mM citrate buffer). A solution, 0.5 mM, of the manganese complex was incubated in the respective buffers at 37° C. (pH=7.4) and the species were then quantified on the LC-MS using the method as described earlier. The manganese complexes (0.5 mM) were also treated with EDTA (0.5 mM) in TRIS buffer (pH=7.4) and incubated at 37° C. for 1 hour. The species were then quantified on the LC-MS using the method as described earlier.

Zn(II) Transmetallation Kinetics.

Displacement of Mn(II) by Zn(II) was measured by monitoring the evolution of free Mn(II) concentration by $T_2$-relaxometry. 1 mM Mn(II) complex was challenged with 25 mM $Zn(OTf)_2$ in 50 mM MES buffer (pH 6.00). The $r_2$ data were fit to the below equation $$r_2 = r_{2(free\,Mn)} * (1-e^{-k*t}) + r_{2o}$$

Synthesis

Materials and Instrumentation.

All chemicals and solvents were purchased commercially and used without further purification. NMR spectra were recorded on either a 500 MHz or 400 MHz Varian spectrometers. Chemical shifts are reported in δ (ppm). For $^1H$ and $^{13}C$ NMR spectra, the residual solvent peaks were used as internal reference, except for the $^{13}C$ NMR of the ligand where tertiary-butanol was used as the internal reference. Liquid chromatography-electrospray mass spectrometry (LC-MS) was performed using an Agilent 1100 Series apparatus with an LC/MSD trap and Daly conversion dynode detector with UV detection at 220, 254 and 280 nm. The methods used on this system are as follows: (a) Luna C18 column (100×2 mm); eluent A: $H_2O$/0.1% formic acid, B: MeCN/0.1% formic acid; gradient: 5% B to 95% B over 9 minutes; flow rate 0.8 mL/min (used for characterization of organic compounds), and (b) Kromasil C18 column (250× 4.6 mm); eluent C: 95% MeCN/5% 10 mM ammonium acetate, D: 10 mM ammonium acetate; gradient 5% C to 8% C over 14 minutes; flow rate 0.8 ml/min (used for characterization of manganese complexes). Reversed-phase semi-preparative purification was performed on the Rainin Dynamax HPLC system with UV detection at 254 nm using a Polaris C18 column. The method used for purification is as follows: The mobile phase A was 50 mM ammonium acetate buffer, pH 6.5 and mobile phase B was a mixture of 5% 50 mM ammonium acetate buffer, pH 6.5/95% MeCN. Starting from 5% B, the fraction of B increased to 8% over 23 minutes. The column was washed with 100% B for 2 minutes and then ramped to 5% B. The system was re-equilibrated at 5% B for 3 minutes. Relaxivity measurements were performed on a Bruker mq60 Minispec at 1.4 T and 37° C. Manganese concentrations were determined using an Agilent 7500a ICP-MS system. All samples were diluted with 0.1% Triton X-100 in 5% nitric acid containing 20 ppb of Lu (as internal standard). The ratio of Mn (54.94)/Lu (174.97) was used to quantify the manganese concentration. A linear calibration curve ranging from 0.1 ppb to 200 ppb was generated daily for the quantification. UV-Vis spectra were recorded on a SpectraMax M2 spectrophotometer using quartz cuvette with a 1 cm path length. pH was measured using a ThermoOrion pH meter connected to a VWR Symphony glass electrode.

Figure 6:
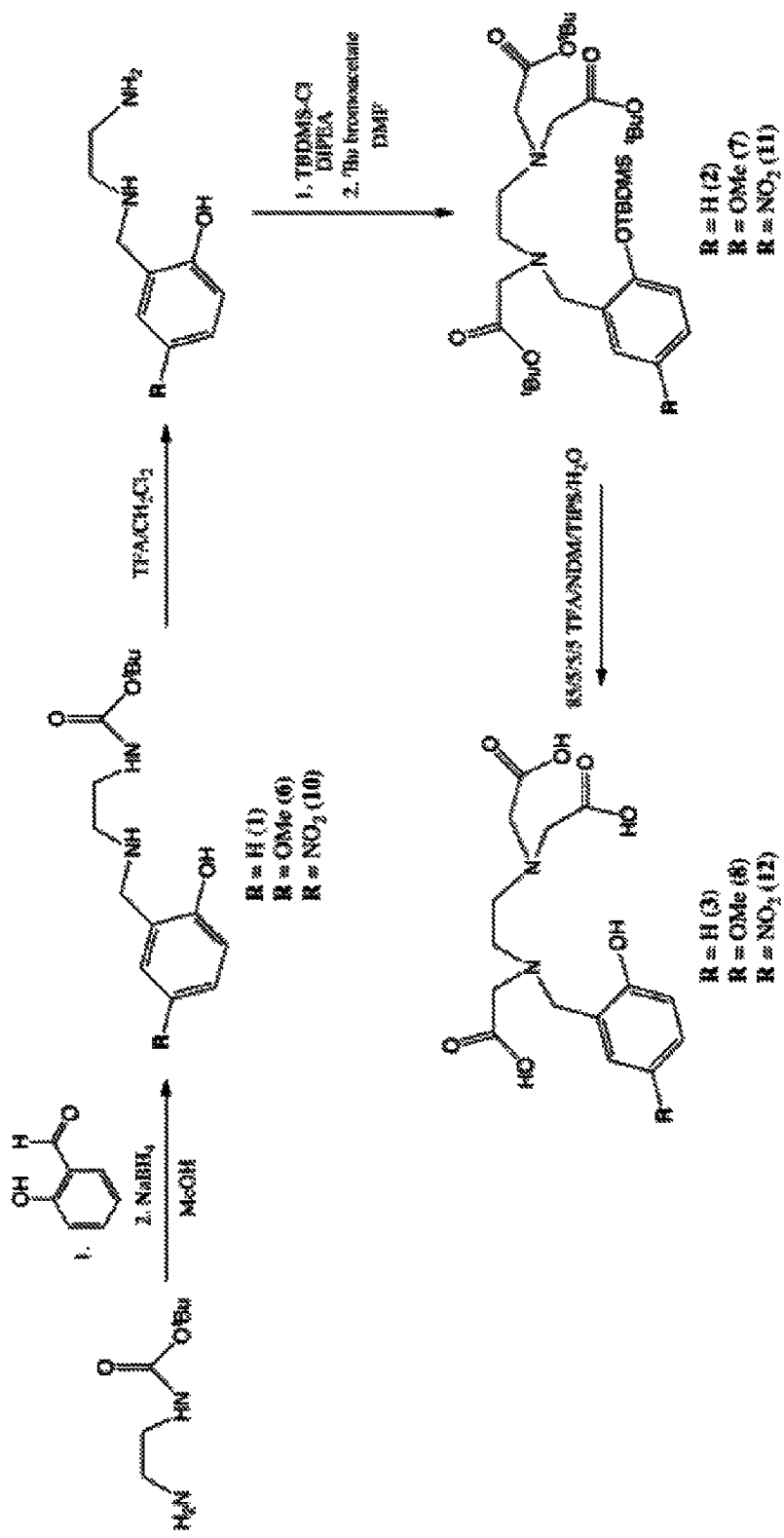
FIG. 6 shows a scheme for the complete synthesis of 2'-((2-((carboxymethyl)(2-hydroxybenzyl)amino)ethyl) azanediyl)diacetic acid (HBET) (3), acid (HBET-OMe) (8) and 2'-((2-((carboxymethyl)(2-hydroxy-5-nitrobenzyl) amino)ethyl)azanediyl)diacetic acid (HBET-$NO_2$) (12).
Figure 7:
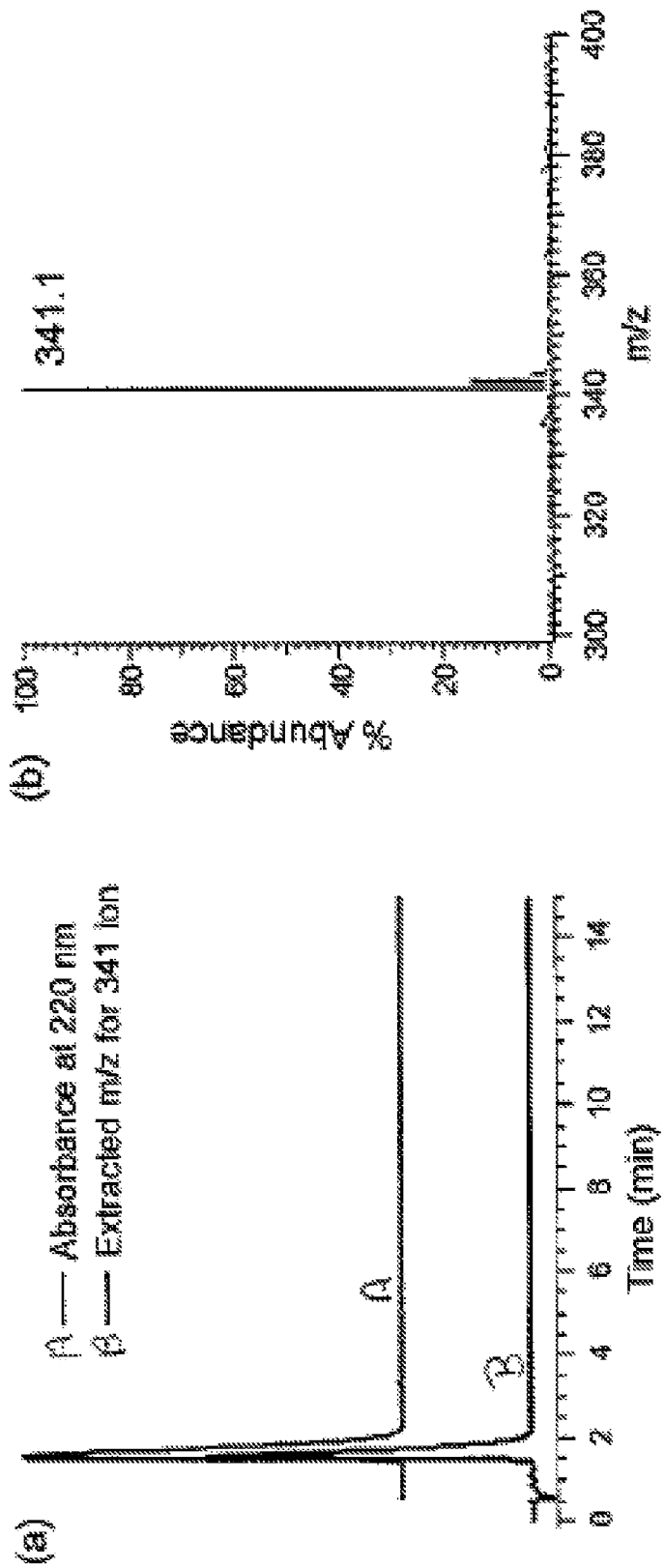
FIG. 7 shows (a) Analytical LC-MS traces of ligand HBET (3) where the trace at 220 nm (black line A) indicates the high purity of the sample and the extracted ion for m/z=341 is shown in red line B which overlaps with the above trace; and (b) ESI-MS of 3 displaying the m/z=341 corresponding to the $[M+H]^+$.
Figure 8:
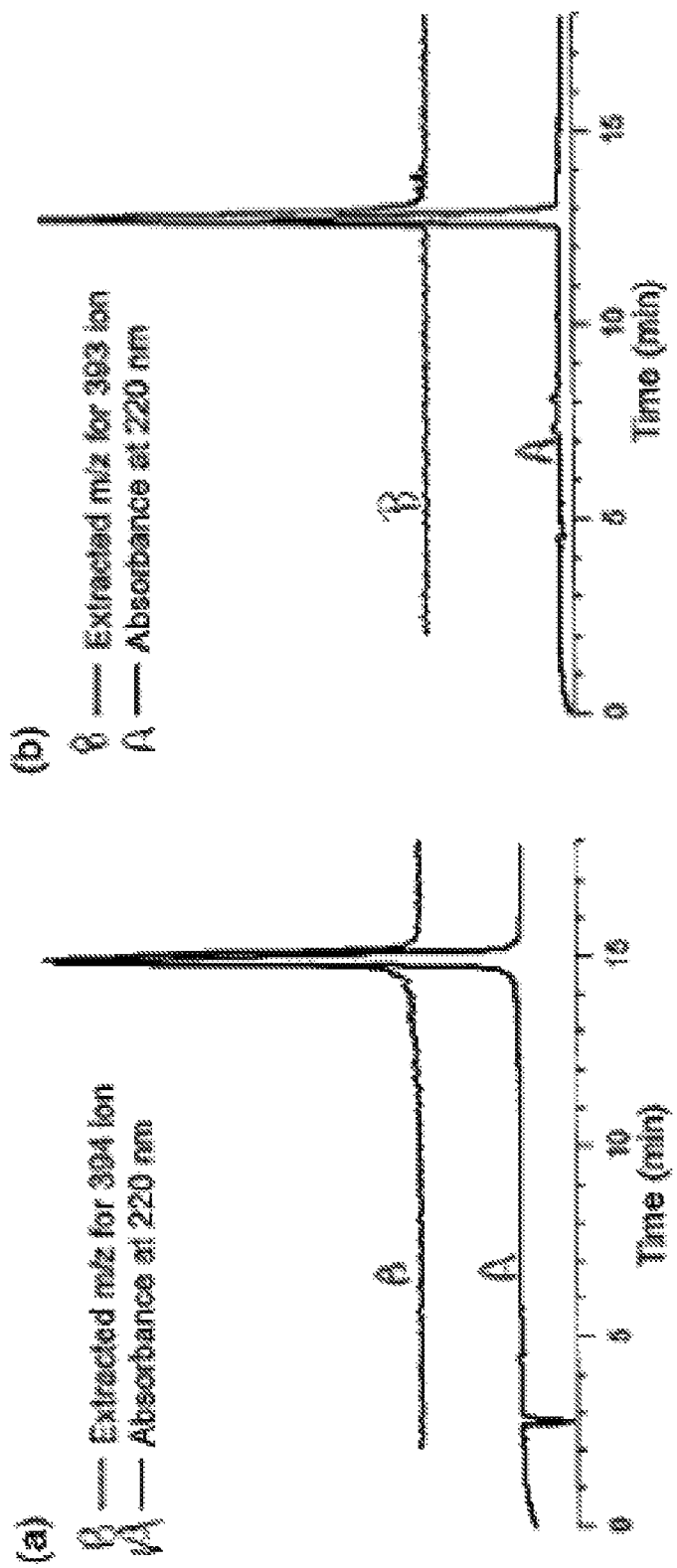
FIG. 8 shows analytical LC-MS traces of (a) $Mn^{II}$HBET (4) and (b) $Mn^{III}$HBET (5) on a C18 reversed-phase column; where the trace at 220 nm (black line A) indicates the high purity of the sample and the extracted ion for m/z=394 and 393 is shown in red line B.
Figure 9:
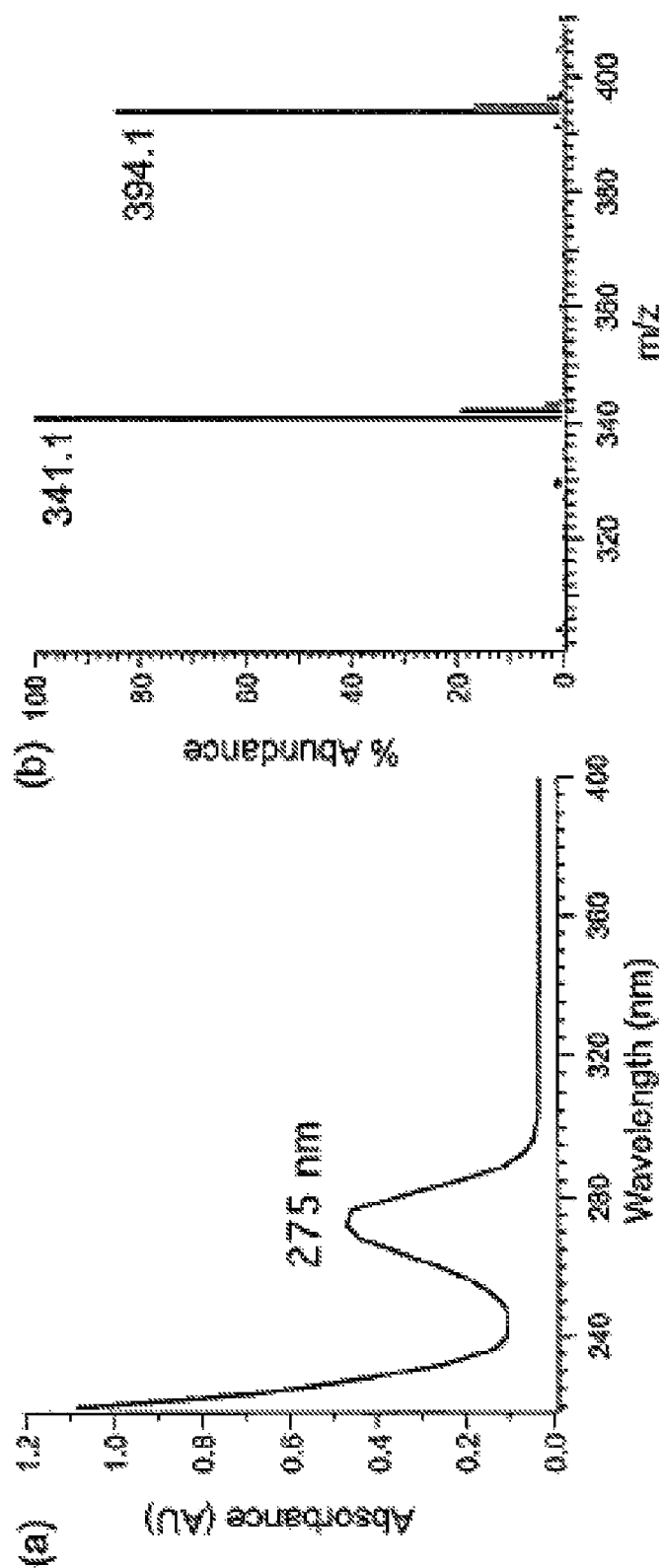
FIG. 9 shows (a) UV spectrum of $Mn^{II}$HBET (4) in water; and (b) ESI-MS of $Mn^{II}$HBET (4) displaying m/z=394 corresponding to $[M+3H]^+$.
Figure 10:
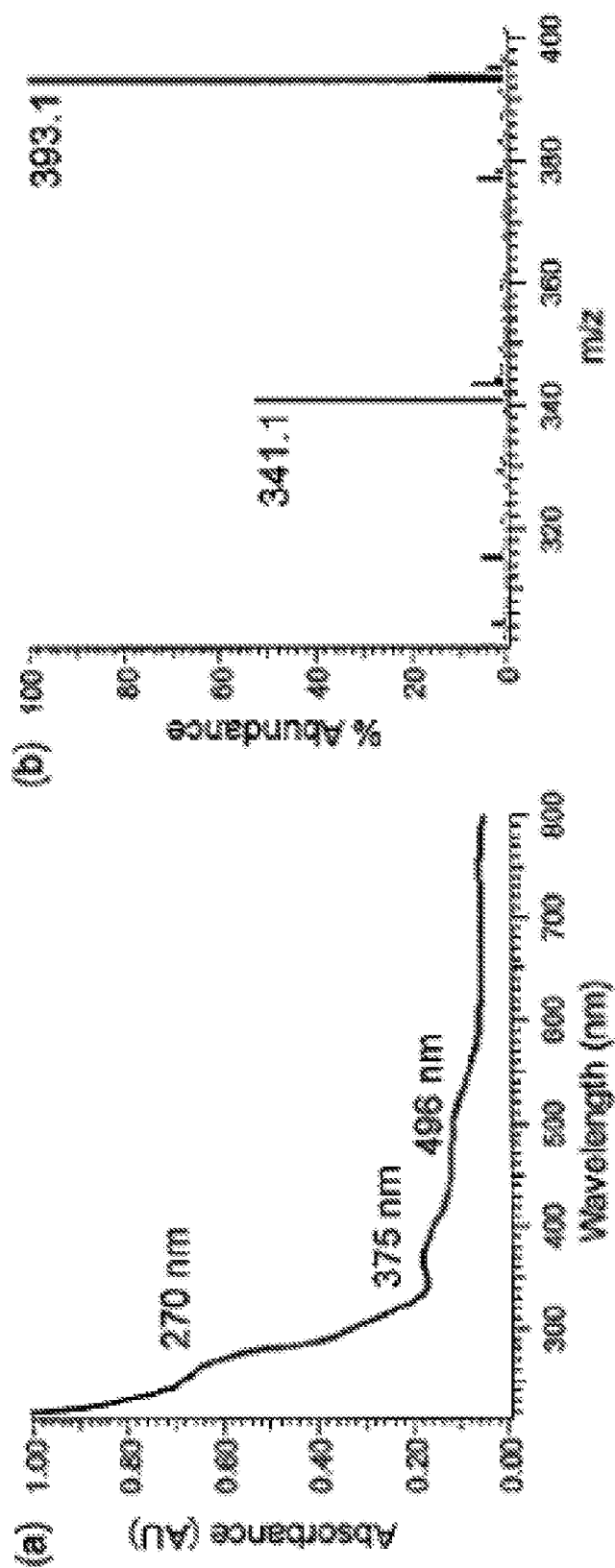
FIG. 10 shows (a) UV spectrum of $Mn^{III}$HBET (5) in water; and (b) ESI-MS of $Mn^{III}$HBET (5) displaying m/z=393 corresponding to $[M+2H]^+$.
Figure 11:
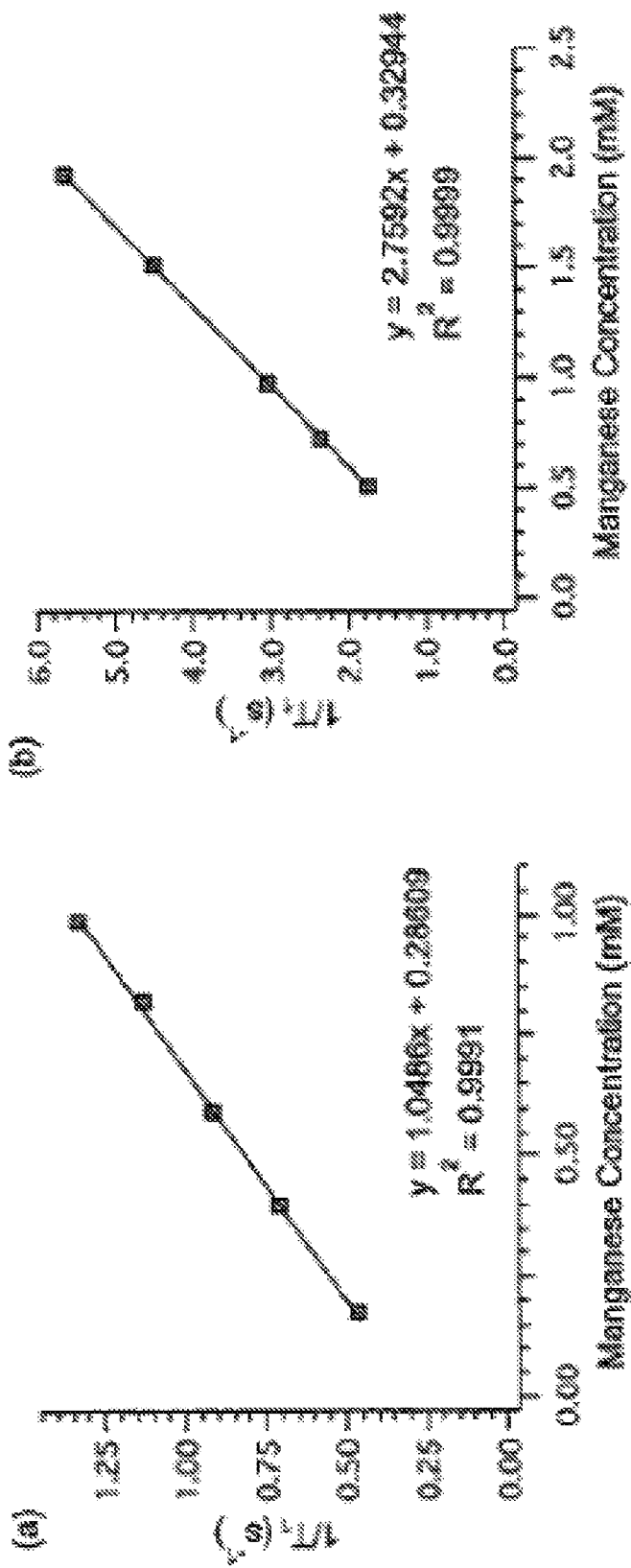
FIG. 11 shows relaxivity of (a) $Na[Mn^{III}HBET]$ (5) and (b) $Na_2[Mn^{II}HBET]$ (4) in TRIS buffer. $1/T_1$ vs. [Mn] for (4) and (5) measured in TRIS buffer at pH 7.4, 37° C. The slope of the line gives the relaxivity.
Figure 12:
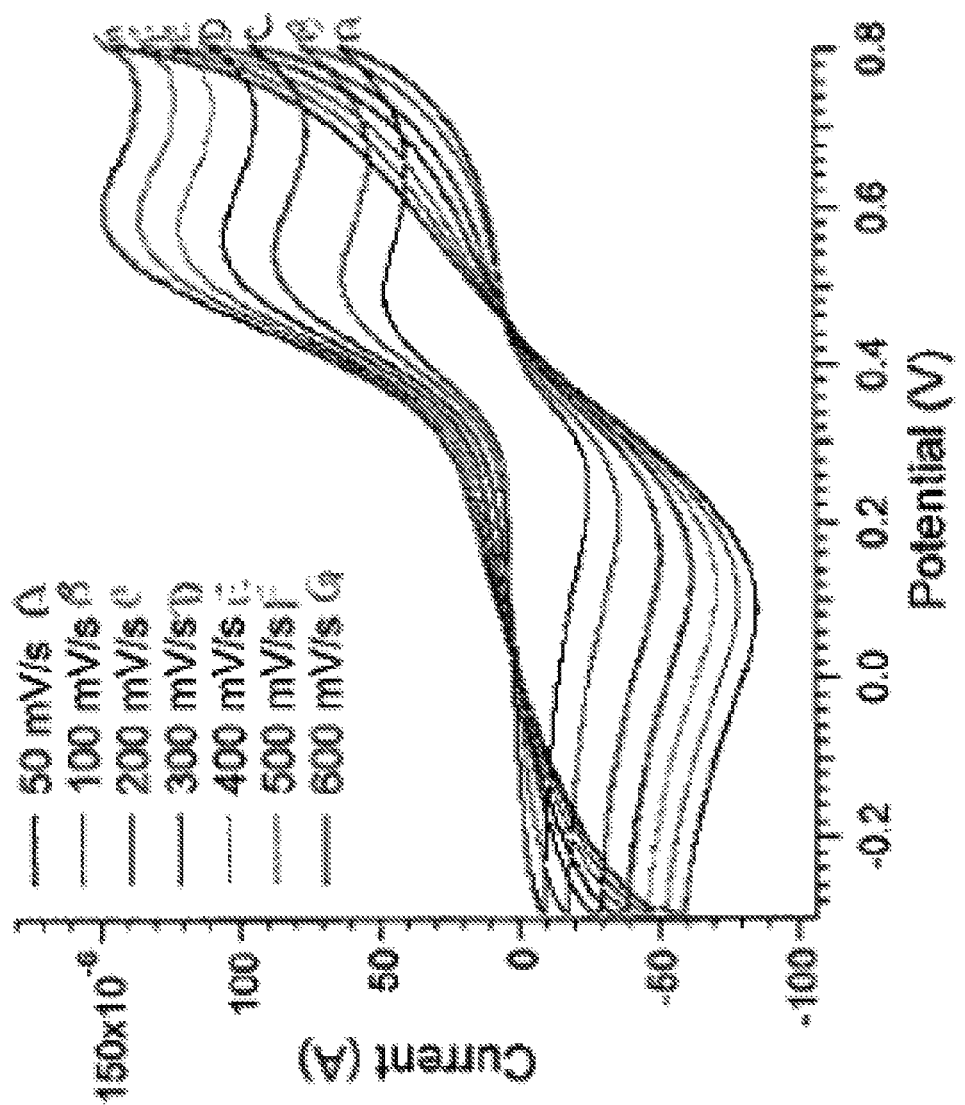
FIG. 12 shows a cyclic voltammogram of $Mn^{II}$HBET (25 mM) in TRIS buffer (pH=7.4) containing $KNO_3$ as the supporting electrolyte at different scan rates ranging from 50-600 mV/s.
Figure 13:
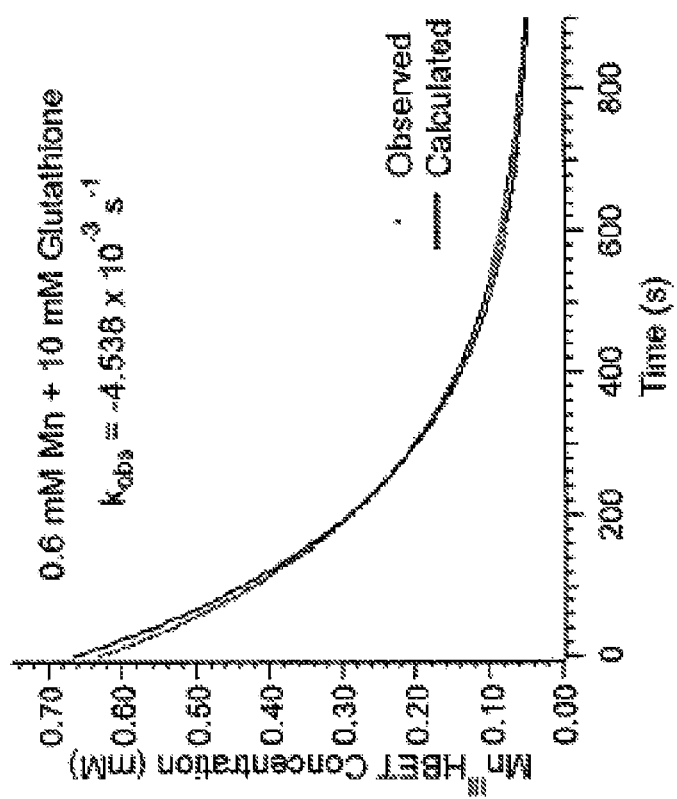
FIG. 13 shows the conversion of $Mn^{III}$-HBET to $Mn^{II}$-HBET in the presence of glutathione as measured by the decrease of the absorbance at 375 nm (dotted line). The solid line shows the fitting of the observed data to a first order rate equation with respect to $Mn^{III}$ under pseudo first order conditions (see equation S1 below).

The synthesis of 2'-((2-((carboxymethyl)(2-hydroxybenzyl)amino)ethyl)azanediyl)diacetic acid (HBET) (3) is shown in FIG. 6.

tert-Butyl (2-((2-hydroxybenzyl)amino)ethyl)carbamate (1): To a solution of salicylaldehyde (12 mmol, 1.465 g) in 90 mL methanol, was added a solution of tert-Butyl N-(2-aminoethyl)carbamate (12 mmol, 1.923 g) in methanol (30 mL) and the solution was stirred for 1 hour. To this stirring solution solid $NaBH^4$ (24 mmol, 0.908 g) was added. Rapid evolution of gas was observed and solution turned colorless from pale yellow. After stirring for 3 hours, all volatiles were removed under reduced pressure, and a white solid was obtained. The residue was dissolved in 200 mL $CH_2Cl_2$ extracted with 200 mL saturated $NaHCO_3$ solution. The aqueous layer was extracted with $CH_2Cl_2$ (2×100 mL). All the organics were combined, washed with brine (200 mL) and dried over anhydrous $MgSO_4$. The solvent was evaporated under reduced pressure to obtain 1 as a pale yellow solid (2.116 g, 97%). $^1H$ NMR (500 MHz, $CDCl_3$) δ (ppm): 7.16 (t, J=7.65 Hz, 1H), 6.99 (d, J=7.48 Hz, 1H) 6.83 (d, J=8.13 Hz, 1H), 6.77 (t, J=7.41 Hz, 1H), 4.01 (s, 2H), 3.30 (m, 2H2.79 (t, J=5.82 Hz, 2H), 1.44 (s, 9H). $^{13}C\{^1H\}$ NMR (100 MHz, $CDCl_3$) δ (ppm): 157.9, 156.2, 128.5, 128.3, 122.4, 118.9, 116.1, 79.2, 52.1, 48.2, 39.8, 28.3. Molecular weight for $C_{14}H_{22}N_2O_3$: 266.34. MS (ESI) m/z: Calculated: 267.17 $(M+H)^+$ observed: 267.1.

di-tert-butyl2,2'(2-((2-(tert-butoxy)-2-oxoethyl)(2-((tert-butyl dimethylsilyl)oxy)-benzyl)amino)ethyl)azanediyl)diacetate (2):1 (7.94 mmol, 2 116 g) was dissolved in $CH_2Cl_2$ (100 mL) followed by addition of 50 mL trifluroacetic acid. The reaction was stirred for 5 hours, and then the volatiles were removed under reduced pressure. The residue was dissolved in water (40 mL) and washed with ether (3×40 mL). The water fraction was freeze dried to produce the free amine quantitatively as a white solid, which was used in subsequent reaction without further purification.

The round bottom flask containing the amine was charged with nitrogen, dry $CH_2Cl_2$ (80 mL) was added and cooled in an ice bath. Under counter argon flow, N,N-Diisopropylethylamine (39.70 mmol, 6.91 mL) was added, followed by addition of tert-butyldimethylsilyl chloride (8.73 mmol, 1.315 g) as a $CH_2Cl_2$ solution (10 mL). The solution was allowed to warm up to room temperature and stirred for 5 hours. The reaction was cooled back to 0° C. and tert-butyl bromoacetate (24.61 mmol, 3.63 mL) was added drop wise and the reaction was stirred for 18 hours under nitrogen atmosphere. The solution was diluted with $CH_2Cl_2$ (200 mL) and washed with saturated $NaHCO_3$ (3×200 mL), brine (1×200 mL). All the organics were combined and dried over anhydrous magnesium sulphate and evaporated under reduced pressure to obtain crude yellow oil. The product was purified as colorless oil (1.234 g, 25%) by using column chromatography (eluent-hexane/ethylacetate, 9:1). $^1H$ NMR (400 MHz, $CDCl_2$) δ (ppm): 7.43 (dd, $J_1$=1.31 Hz, $J_2$=7.57, 1H), 7.04 (dt, $J_1$=1.71 Hz, $J_2$=7.80, 1 H), 6.88 (t, J=7.51 Hz, 1H), 6.72 (d, J=7.93 Hz, 1H), 3.76 (s, 2H), 3.40 (s, 4H), 3.29

(s, 2H), 2.81 (m, 4H), 1.41 (s, 9H), 1.40 (s, 18H), 0.98 (s, 9H), 0.18 (s, 6H). $^{13}C\{^{1}H\}$ NMR (100 MHz, $CDCl_2$) δ (ppm): 171.1, 170.7, 153.7, 130.1, 129.8, 127.4, 121.1, 118.4, 80.6, 80.4, 56.1, 55.9, 52, 52.4, 28.2, 25.9, 18.3, 4.1. Molecular weight for $C_{33}H_{58}SN_2O_7Si$: 622.91. MS (ESI) m/z: Calculated: 623.41 $(M+H)^+$ observed: 623.4.

2,2'-((2-((carboxymethyl)(2-hydroxybenzyl)amino)ethyl)azanediyl)diacetic acid (HBET) (3): 2 (1.98 mmol, 1.234 g) was dissolved in trifluroacetic acid (40 mL) followed by addition of triisopropylsilane (2.35 mL), 1-dodecanethiol (2.35 mL) and water (2.35 mL). The reaction was stirred for 5 hours, and then the volatiles were removed under reduced pressure. The residue was dissolved in water (40 mL and washed with ether (3×40 mL). The water fraction was freeze dried to produce (3) quantitatively as a white solid. $^{1}H$ NMR (500 MHz, $D_2O$) δ (ppm): 7.44 (m, 2H, Ar—H), 7.03 (m, 2H) 4.57 (s, 2H), 4.04 (s, 2H), 3.66 (s, 4H), 3.54 (t, J=6.09 Hz, 2H), 3.35 (t, J=5.9 Hz, 2H). $^{13}C\{^{1}H\}$ NMR (125 MHz, $D_2O$) δ (ppm): 174.1, 169.9, 156.3, 133.6, 133.0, 121.5, 116.6, 116.3, 55.6, 54.8, 52.0, 49.9. Molecular weight for $C_{15}H_{20}N_2O_7$: 340.33. MS (ESI) m/z: Calculated: 341.13 $(M+H)^+$; observed: 341.1.

$Na_2[Mn^{II}HBET]$ (4): 3 (0.26 mmol, 0.089 g) was dissolved in 5 mL water. The pH was adjusted to 8 using 1 N sodium hydroxide solution. $MnCl_2.4H_2O$ (0.26 mmol, 0.051 g) was then added to the solution and the pH was carefully adjusted to 5. The reaction was stirred for 1 hour, filtered and freeze dried to yield a white solid. The complex was injected onto a reverse phase C18 (Polaris) column and desalted using the method as described earlier. The fractions were collected and lyophilized to yield 4 as a white solid (0.095 g, 84%). Molecular Weight for $C_{15}H_{18}MnN_2O_7$: 393.25. MS (ESI) m/z: Calculated: 394.26 $(M+3H)^+$ Observed: 394.1.

$Na[Mn^{III}HBET]$ (5): 3 (0.15 mmol, 0.05 g) was dissolved in 5 mL water. The pH was adjusted to 8 using 1 N sodium hydroxide solution. $MnCl_2.4H_2O$ (0.15 mmol, 0.030 g) was then added to the solution and the pH was adjusted to 12. The solution was allowed to stir for 1 hour. The solution was then filtered through a 0.45 μm filter to remove $MnO_2$, pH adjusted to 11 and the solution was stirred for 18 hours. The reaction was followed using analytical LC-MS and the reaction was stopped when 70% conversion to the $Mn^{III}$ species was observed. The mixture was injected onto a reverse phase C18 (Polaris) column and purified using the method as described earlier. The fractions were collected and lyophilized to yield 5 as a brown solid (0.023 g, 38%). Molecular Weight for $C_{15}H_{17}MnN_2O_7$: 392.24. MS (ESI) m/z: Calculated: 393.25 $(M+2H)^+$ Observed: 393.1.

tert-Butyl (2-((2-hydroxy-5-methoxybenzyl)aminoethyl) carbamate (6): To a solution of 2-hydroxy-5-methoxybenzaldehyde (12 mmol, 1.826 g) in 90 mL methanol, was added a solution of tert-Butyl N-(2-aminoethyl)carbamate (12 mmol, 1.923 g) in methanol (30 mL) and the solution was stirred for 1 hour. To this stirring solution, solid $NaBH_4$ (24 mmol, 0.908 g) was added. Rapid evolution of gas was observed and solution turned colorless from pale yellow. After stirring for 3 hours, all volatiles were removed under reduced pressure, and a white solid was obtained. The residue was dissolved in 200 mL $CH_2Cl_2$ extracted with 200 mL saturated $NaHCO_3$ solution. The aqueous layer was extracted with $CH_2Cl_2$ (2×100 mL). All the organics were combined, washed with brine (200 mL) and dried over anhydrous $MgSO_4$. The solvent was evaporated under reduced pressure to obtain 6 as a pale yellow solid (3.485 g, 98%). $^{1}H$ NMR (500 MHz, $CDCl_3$) δ (ppm): 6.76 (m, 1H) 6.72 (m, 1H), 6.57 (d, J=2.91 Hz, 1H), 5.30 (s, 1H), 3.97 (s, 2H), 3.73 (s, 3H), 3.28 (m, 2H), 2.78 (t, J=5.72 Hz, 2H), 1.44 (s, 9H). $^{13}C\{^{1}H\}$ NMR (100 MHz, $CDCl_2$) δ (ppm): 156.2, 152.3, 151.7, 123.1, 116.5, 114.2, 113.5, 79.3, 55.6, 52.2, 48.3, 39.9, 28. Molecular weight for $C_{15}H_{24}N_2O_4$: 296.36. MS (ESI) m/z: Calculated: 297.37 $(M+H)^+$; observed: 297.4.

di-tert-butyl2,2'-((2-((2-(tert-butoxy)-2-oxoethyl)(2-((tert-butyl dimethylsilyl)oxy)-5-methoxybenzyl)amino) ethyl)azanediyl)diacetate (7): 6 (8.00 mmol, 2.371 g) was dissolved in $CH_2Cl_2$ (100 mL) followed by addition of 50 mL trifluroacetic acid. The reaction was stirred for 5 hours, and then the volatiles were removed under reduced pressure. The residue was dissolved in water (40 mL) and washed with ether (3×40 mL). The water fraction was freeze dried to produce the free amine quantitatively as a pale yellow solid, which was used in subsequent reaction without further purification.

The round bottom flask containing the amine was charged with nitrogen, dry $CH_2Cl_2$ (80 mL) was added and cooled in an ice bath. Under counter argon flow, N, N-Diisopropylethylamine (40.00 mmol, 6.97 mL) was added, followed by addition of tert-butyldimethylsilyl chloride (8.80 mmol, 1.326 g) as a $CH_2Cl_2$ solution (10 mL). The solution was allowed to warm up to room temperature and stirred for 5 hours. The reaction was cooled back to 0° C. and tert-butyl bromoacetate (24.80 mmol, 3.66 mL) was added drop wise and the reaction was stirred for 18 hours under nitrogen atmosphere. The solution was diluted with $CH_2Cl_2$ (200 mL) and washed with saturated $NaHCO_3$ (3×200 mL), brine (1×200 mL). All the organics were combined and dried over anhydrous magnesium sulphate and evaporated under reduced pressure to obtain crude yellow oil. The product was purified as colorless oil (1.462 g, 28%) by using column chromatography (eluent-hexane/ethylacetate, 9:1). $^{1}H$ NMR (400 MHz, $CDCl_3$) δ (ppm): 7.04 (d, J=3.26 Hz, 1H), 6.62 (m, 1H), 6.57 (m, 1H), 3.71 (s, 2H), 3.70 (s, 3H), 3.40 (s, 4H), 3.27 (s, 2H), 2.79 (m, 4H), 1.40 (s, 9H), 1.37 (s, 18H), 0.94 (s, 9H), 0.13 (s, 6H). $^{13}C\{^{1}H\}$ NMR (100 MHz, $CDCl_2$) δ (ppm): 171, 170.8, 154.1, 147.4, 130.8, 119.2, 114.7, 113.0, 80.8, 80.6, 56.3, 56.1, 55.6, 53.1, 52.8, 52.7, 28.3, 28.2, 26.0, 18.4. Molecular weight for $C_{34}H_{60}N_2O_8Si$: 652.93. MS (ESI) m/z: Calculated: 653.94 $(M+H)^+$; observed: 653.9.

2,2'-(2-((carboxymethyl)(2-hydroxy-5-methoxybenzyl) amino)ethyl) azanediyl)diacetic acid (HBET-OMe) (8): 7 (2.24 mmol, 1.462 g) was dissolved in trifluoroacetic acid (40 mL) followed by addition of triisopropylsilane (2.35 mL), 1-dodecanethiol (2.35 mL) and water (2.35 mL). The reaction was stirred for 5 hours, and then the volatiles were removed under reduced pressure. The residue was dissolved in water (40 mL) and washed with ether (3×40 mL). The water fraction was freeze dried to produce 8 quantitatively as a white solid. $^{1}H$ NMR (500 MHz, $D_2O$) δ (ppm): 7.02 (m, 2H) 6.95 (m, 1H) 4.52 (5, 2H), 4.09 (s, 2H), 3.80 (s, 3H), 3.58 (s, 4H), 3.48 (m, 2H), 3.26 (m, 2H). $^{13}C\{^{1}H\}$ NMR (125 MHz, $D_2O$) δ (ppm): 173.6, 169.0, 152.5, 149.6, 117.9, 117.6, 117.0, 116.4, 55.9, 54.8, 51.5, 49.0. Molecular weight for $C_{16}H_{22}N_2O_8$: 370.35. MS (ESI) m/z: Calculated: 371 36 $(M+H)^+$ observed: 371.4.

$Na_2[Mn^{II}HBET$-$OMe]$ (9): 8 (0.23 mmol, 0.085 g) was dissolved in 5 mL water. The pH was adjusted to 8 using 1 N sodium hydroxide solution. $MnCl_2.4H_2O$ (0.23 mmol, 0.046 g) was then added to the solution and the pH was carefully adjusted to 5. The reaction was stirred for 1 hour, filtered and freeze dried to yield a white solid. The complex was injected onto a reverse phase C18 (Polaris) column and desalted using the method as described earlier. The fractions were collected and lyophilized to yield 9 as a white solid (0.090 g, 81%). Molecular Weight for $C_{16}H_{22}MnN_2O_8$: 423.28. MS (ESI) m/z: Calculated: 424.28 (M−3H)⁺; Observed: 424.3.

tert-Butyl (2-((2-hydroxy-5-nitrobenzyl)amino)ethyl)carbamate (10): To a solution of 2-hydroxy-5-nitrobenzaldehyde (3.51 mmol, 0.587 g) in 60 mL methanol, was added a solution of tert-Butyl N-(2-aminoethyl)carbamate (3.51 mmol, 0.562 g) in methanol (30 mL) and the solution was stirred for 1 hour. To this stirring solution, solid $NaBH_4$ (7.02 mmol, 0.266 g) was added. Rapid evolution of gas was observed and solution turned colorless from pale yellow. After stirring for 3 hours, all volatiles were removed under reduced pressure, and a white solid was obtained. The residue was dissolved in a solvent mixture of 10 mL methanol and 200 mL $CH_2Cl_2$ and extracted with 200 mL saturated $NaHCO_3$ solution. The aqueous layer was extracted with $CH_2Cl_2$ (2×100 mL). All the organics were combined, washed with brine (200 mL) and dried over anhydrous $MgSO_4$. The solvent was evaporated under reduced pressure to obtain 10 as a yellow solid (1.01 g, 93%). ¹H NMR (500 MHz, $(CD_3)_2SO$) δ (ppm): 8.01 (d, J=3.0 Hz, 1H) 7.92 (dd, $J_1$=3.00 Hz, $J_2$=9.2 Hz, 1H), 6.92 (t, J=5.8 Hz, 1H), 6.46 (d, J=9.2 Hz, 1H), 3.93 (s, 2H), 3.14 (m, 2H), 2.75 (t, J=6.3 Hz, 2H), 1.38 (s, 9H). $^{13}C\{^1H\}$ NMR (100 MHz, $CDCl_3$) δ (ppm): 172.1, 155.7, 133.6, 126.1, 126.0, 121.9, 117.3, 77.9, 48.7, 46.7, 37.9, 28.2. Molecular weight for $C_{14}H_{21}N_3O_5$: 311.33. MS (ESI) m/z: Calculated: 312.34 (M+H)⁺; observed: 312.4.

di-tert-butyl2,2'-((2-((2-(tert-butoxy)-2-oxoethyl)(2-((tert-butyl dimethylsilyl)oxy)-5-nitrobenzyl)amino)ethyl)azanediyl)diacetate (11): 10 (3.24 mmol, 1.01 g) was dissolved in $CH_2Cl_2$ (100 mL) followed by addition of 50 mL trifluroacetic acid. The reaction was stirred for 5 hours, and then the volatiles were removed under reduced pressure. The residue was dissolved in water (40 mL) and washed with ether (3×40 mL). The water fraction was freeze dried to produce the free amine quantitatively as a pale yellow solid, which was used in subsequent reaction without further purification.

The round bottom flask containing the amine was charged with nitrogen, dry dimethylformamide (40 mL) was added and cooled in an ice bath. Under counter argon flow, N,N-Diisopropylethylamine (16.2 mmol, 2.82 mL) was added, followed by addition of tert-butyldiphenylsilyl chloride (3.56 mmol, 0.979 g) as a dimethylformamide solution (5 mL). The solution was allowed to warm up to room temperature and stirred for 5 hours. The reaction was cooled back to 0° C. and tertbutyl bromoacetate (10.04 mmol, 1.48 mL) was added drop wise and the reaction was stirred for 18 hours under nitrogen atmosphere. The solution was diluted with $CH_2Cl_2$ (200 mL) and washed with saturated $NaHCO_3$ (3×200 mL), brine (1×200 mL). All the organics were combined and dried over anhydrous magnesium sulphate and evaporated under reduced pressure to obtain crude yellow oil. The product was purified as colorless oil (0.615 g, 24%) by using column chromatography (eluent-hexane/ethylacetate, 9:1). ¹H NMR (400 MHz, $CDCl_3$) δ (ppm): 8.50 (d, J=2.9 Hz, 1H), 7.67 (m, 5H), 7.45 (m, 1H), 7.39 (m, 5H), 6.40 (d, 2H, J=2.9 Hz, 1H), 4.08 (s, 2H), 3.48 (s, 4H), 3.44 (s, 2H), 2.93 (s, 4H), 1.48 (s, 9H), 1.43 (s, 18H), 1.1194 (s, 9H). $^{13}C\{^1H\}$ NMR (100 MHz, $CDCl_3$) δ (ppm): 170.8, 159.0, 142.1, 135.3, 131.4, 130.5, 128.2, 125.6, 123.3, 118.7, 81.1, 81.0, 56.5, 56.2, 53.0, 52.8, 52.7, 28.2, 26.5, 19.7. Molecular weight for $C_{43}H_{61}N_3O_9Si$: 792.04. MS (ESI) m/z: Calculated: 793.05 (M+H)⁺, observed: 793.1.

2,2-((2-((carboxymethyl)(2-hydroxy-5-nitrobenzyl)amino)ethyl) azanediyl)diacetic acid (HBET-$NO_2$) (12): 11 (0.776 mmol, 0.615 g) was dissolved in trifluoroacetic acid (40 mL) followed by addition of triisopropylsilane (2.35 mL), 1-dodecanethiol (2.35 mL) and water (2.35 mL). The reaction was stirred for 5 hours, and then the volatiles were removed under reduced pressure. The residue was dissolved in water (40 mL) and washed with ether (3×40 mL). The water fraction was freeze dried to produce 12 quantitatively as a white solid. ¹H NMR (500 MHz, $D_2O$) δ (ppm): 8.33 (m, 1H), 8.22 (m, 1H), 7.06 (d, J=9.0 Hz, 1H), 4.57 (s, 2H), 4.07 (s, 2H), 3.60 (s, 4H), 3.49 (m, 2H), 3.27 (m, 2H). $^{13}C\{^1H\}$ NMR (125 MHz, $D_2O$) δ (ppm): 173.5, 169.1, 162.2, 140.1, 129.1, 128.0, 116.7, 116.0, 54.8, 54.0, 51.9, 49.2. Molecular weight for $C_{15}H_{19}N_3O_9$: 385.33. MS (ESI) m/z: Calculated: 386.33 (M+H)⁺; observed: 386.4.

$Na_2[Mn^{II}HBET-NO_2]$ (13): 12 (0.25 mmol, 0.096 g) was dissolved in 5 mL water. The pH was adjusted to 8 using 1 N sodium hydroxide solution. $MnCl_2.4H_2O$ (0.25 mmol, 0.049 g) was then added to the solution and the pH was carefully adjusted to 5. The reaction was stirred for 1 hour, filtered and freeze dried to yield a white solid. The complex was injected onto a reverse phase C18 (Polaris) column and desalted using the method as described earlier. The fractions were collected and lyophilized to yield 13 as a light yellow solid (0.102 g, 82%). Molecular Weight for $C_{15}H_{17}MnN_3O_9$: 438.25. MS (ESI) m/z: Calculated: 439.26 (M+3H)⁺; Observed: 439.4.

Figure 19:
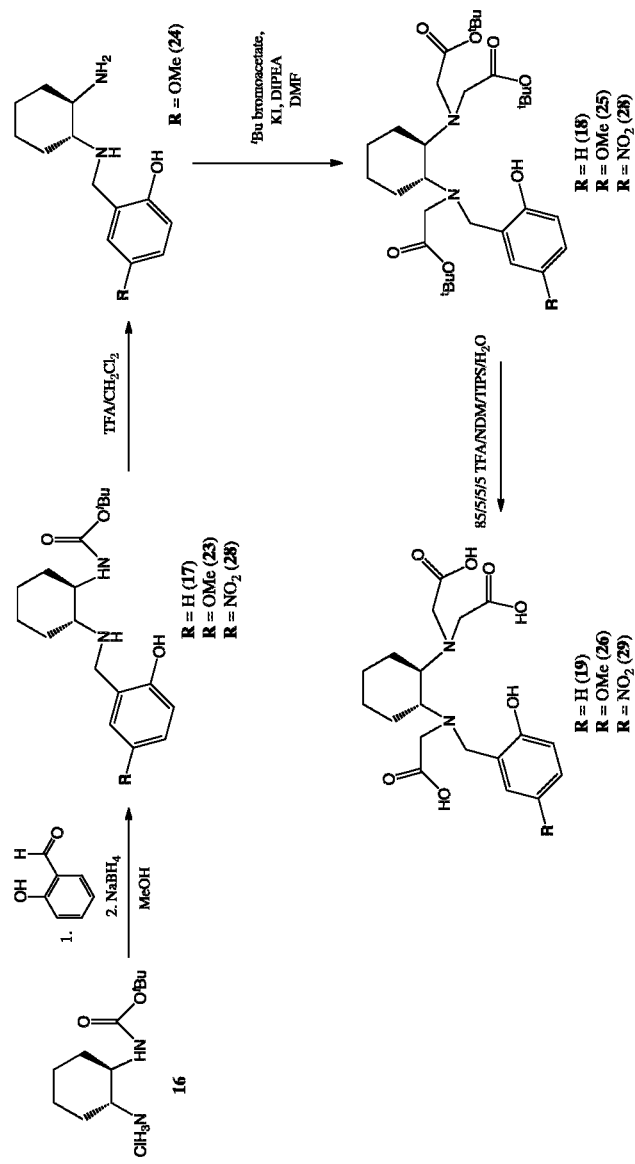
FIG. 19 shows a synthetic route for cycHBET series compounds of the invention.
Figure 20A:
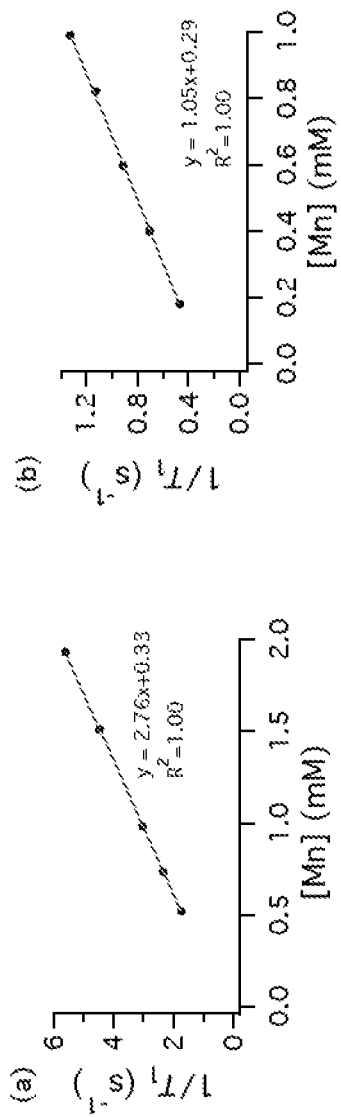
FIG. 20A shows the relaxivity of (a) $Na_2[Mn^{II}HBET]$ (4) and (b) $Na[Mn^{III}HBET]$ (5) in TRIS buffer at pH 7.4, 37° C. The slope of the line gives the relaxivity.
Figure 20B:
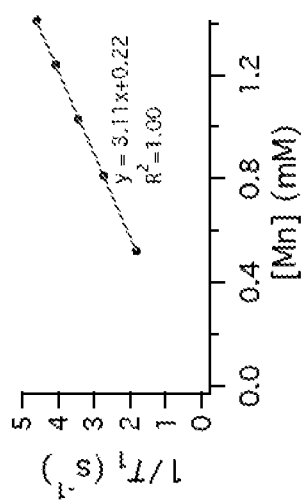
FIG. 20B shows the relaxivity of $Na_2[Mn^{II}HBET-OMe]$ (9) in TRIS buffer at pH 7.4, 37° C. The slope of the line gives the relaxivity.
Figure 20C:
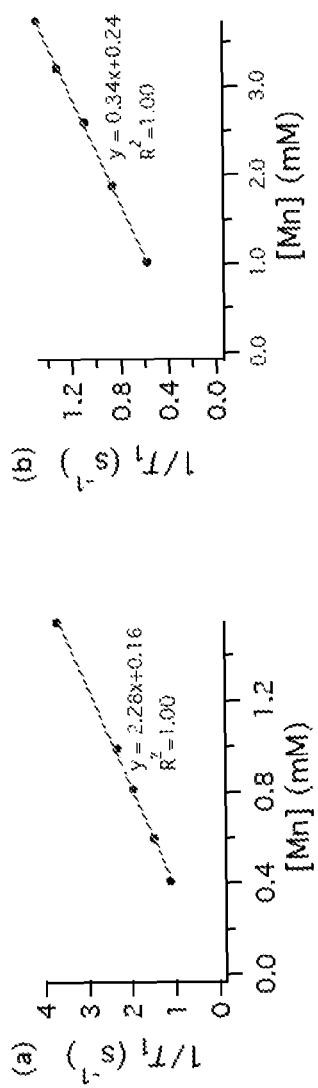
FIG. 20C shows the relaxivity of $Na_2[Mn^{II}HBET-NO_2]$ (13) and $Na[Mn^{III}HBET-NO_2]$ (14) in TRIS buffer at pH 7.4, 37° C. The slope of the line gives the relaxivity.
Figure 20D:
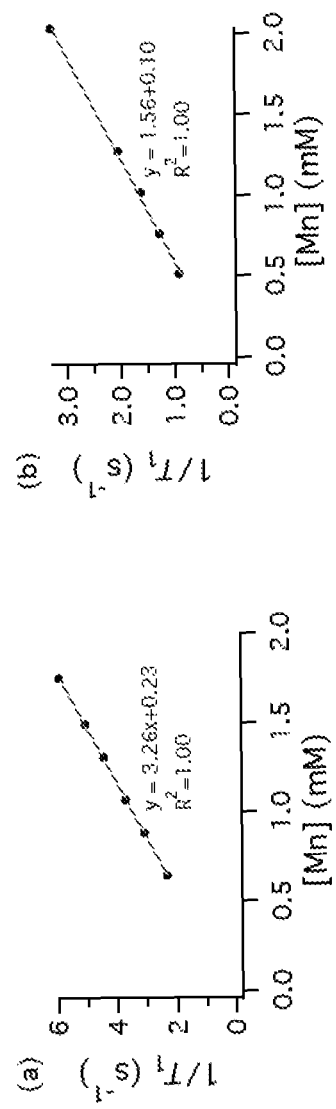
FIG. 20D shows the relaxivity of $Na_2[Mn^{II}cycHBET]$ (30) in TRIS buffer at pH 7.4, 37° C. The slope of the line gives the relaxivity.

$Na[Mn^{III}HBET-NO_2]$ (14): $MnF_3$ (0.006 g, 0.054 mmol) was added to 12 (0.021 g, 0.054 mmol) stirring in 5 mL $H_2O$ at pH 8. The resultant red-orange solution was injected onto a reverse phase C18 (Polaris) column and purified using the method as described earlier. The fractions were collected and lyophilized to yield 14 as a brown solid (0.012 g, 0.026 mmol, 48%). Molecular Weight for $C_{19}H_{21}MnN_3O_9$: 436.23. MS (ESI) m/z: Calculated: 436.02 (My; Observed: 436.

trans-1,2 diaminocyclohexanaminium chloride (15): To a solution of trans-1,2 diaminocyclohexane (48 mmol, 5.523 g) in 200 mL ether, 20.4 mL of 2M HCl in ether was added dropwise under counter nitrogen flow. The reaction was allowed to stir for 2 hours, during which time the product formed as a white precipitate. The precipitate was collected and washed with copious amounts of ether. Yield: 97% (7.05 g). ¹H NMR (500 MHz, $CD_3OD$) δ (ppm): 2.67 (m), 2.04 (m, 2H1.78 (m, 2H), 1.35 (m, 4H). Molecular weight for $C_6H_{14}N_2$: 114.19. MS (ESI) m/z: Calculated: 115.2 (M+H)⁺; observed: 115.4. $^{13}C\{^1H\}$ NMR (125 MHz, $CD_3OD$) δ (ppm): 56.1, 33.7, 25.6. Molecular weight for $C_6H_{14}N_2$: 114.19. MS (ESI) m/z: Calculated: 115.2 (M+H)⁺; observed: 115.4.

trans-2-((tert-butoxycarbonyl)amino)cyclohexanaminium chloride (16) (see FIG. 19): To a solution of 15 (10 mmol, 1.507 g) in 90 mL methanol, was added a solution of di-tert-butyl dicarbonate (9.1 mmol, 1.986 g) in methanol (30 mL) dropwise over 1 hour. After stirring for 18 hours, all volatiles were removed under reduced pressure, and the product was obtained as a yellowish-white solid. The solid was washed with copious amounts of dichloromethane, to remove any unreacted starting material. Yield: 97% (2.21 g). ¹H NMR (500 MHz, $CD_3OD$) δ (ppm): 3.07 (s, 1H), 2.40 (s, 1H), 1.91 (m, 2H), 1.70 ((m, 2H), 1.44 (s, 9H), 1.28 (m, 2H), 1.19 (m, 2H). $^{13}C\{^1H\}$ NMR (125 MHz, $CD_3OD$) δ (ppm): 156.7, 79.3, 54.3, 52.4, 31.6, 29.7, 27.4, 24, 23.6. Molecular weight for $C_{11}H_{22}N_2O_2$: 214.30. MS (ESI) m/z: Calculated: 215.3 (M+H)⁺; observed: 215.4. Molecular weight for $C_{11}H_{22}N_2O_2$: 214.30. MS (ESI) m/z: Calculated: 215.3 (M+H)⁺; observed: 215.4.

tert-butyl (trans-2-((2-hydroxybenzyl)amino)cyclohexyl) carbamate (17): To a solution of 16 (3.99 mmol, 1.001 g) in 90 mL MeOH, NEt$_3$ (4.39 mmol, 0.6 mL) was added and the reaction was stirred for 30 minutes. To the above mixture a solution of salicylaldehyde (3.99 mmol, 0.487 g) in methanol (30 mL) was added. After stirring for 1 hour, solid NaBH$_4$ (8.38 mmol, 0.317 g) was added and the reaction was stirred for 3 hours. All the volatiles were removed under reduced pressure, to yield a pale yellow solid. The residue was dissolved in 200 mL CH$_2$Cl$_2$ extracted with 200 mL saturated NaHCO$_3$ solution. The aqueous layer was extracted with CH$_2$Cl$_2$ (2×100 mL). All the organics were combined, washed with brine (200 mL) and dried over anhydrous MgSO$_4$. The solvent was evaporated under reduced pressure to obtain 17 as a pale yellow solid (1.231 g, 96%). $^1$H NMR (500 MHz, CDCl$_3$) δ (ppm): 7.15 (m, 1H), 6.96 (m, 1H), 6.81 (m, 1H), 6.75 (m, 1H), 4.43 (s, 1H), 4.05 (d, 1H), 3.93 (d, 1H), 3.41 (s, 1H), 2.31 (m, 1H) 2.17 (m, 1H), 1.99 (m, 1H), 1.70 (m, 2H), 1.46 (s, 9H), 1.31 (m, 1H), 1.17 (m, 2H). $^{13}$C{$^1$H} NMR (125 MHz, CDCl$_3$) δ (ppm): 158.3, 156.0, 128.4, 128.0, 123.1, 118.7, 116.3, 79.4, 60.9, 53.9, 49.8, 33.0, 31.2, 28.3, 24.9, 24.5. Molecular weight for C$_{18}$H$_{28}$N$_2$O$_3$: 320.43. MS (ESI) m/z: Calculated: 321.43 (M+H)$^+$; observed: 321.5.

di-tert-butyl 2,2'-((trans-2-((2-(tert-butoxy)-2-oxoethyl) (2-hydroxybenzyl)amino)cyclohexyl)azanediyl)diacetate (18) 17 (3.15 mmol, 1.01 g) was dissolved in CH$_2$Cl$_2$ (100 mL) followed by addition of 50 mL trifluroacetic acid. The reaction was stirred for 5 hours, and then the volatiles were removed under reduced pressure. The residue was dissolved in water (40 mL) and washed with ether (3×40 mL). The water fraction was freeze dried to produce the free amine quantitatively as a pale yellow solid, which was used in subsequent reaction without further purification.

To the round bottom flask containing the amine, KI (6.3 mmol, 1.04 g) was added and system was purged with nitrogen. Under counter nitrogen flow, dry dimethylformamide (2 mL) was added followed by the addition of N,N Diisopropylethylamine (15.75 mmol, 2.74 mL) and dropwise addition of tert-butyl bromoacetate (9.765 mmol, 1.90 g). The reaction was stirred for 18 hours and then partitioned between saturated NaHCO$_{3(aq)}$ and Et$_2$O. The Et$_2$O layer was separated and washed with several changes of H$_2$O to remove DMF before drying over Na$_2$SO$_4$ and concentration to 1.0 g of yellow oil. Molecular weight for C$_{31}$H$_{50}$N$_2$O$_7$: 562.74. MS (ESI) m/z: Calculated: 563.75 (M+H)$^+$; observed: 563.8. The crude product was carried on in the next step without further purification.

2,2'-((trans-2-((carboxymethyl)(2-hydroxybenzyl)amino) cyclohexyl)azanediyl)diacetic acid (19): The crude product (17) from the previous step was dissolved in trifluroacetic acid (40 mL) followed by addition of triisopropylsilane (2.35 mL). 1-dodecanethiol (2.35 mL) and water (2.35 mL). The reaction was stirred for 5 hours, and then the volatiles were removed under reduced pressure. The residue was dissolved in water (40 mL) and washed with ether (3×40 mL). The water fraction was freeze dried to produce crude 19. The product was then purified via preparative HPLC using a Polaris C18 column; eluent A: H$_2$O/0.1% TFA, B: MeCN/0.1% TFA; gradient 5% to 50% B over 25 minutes; flow rate: 15 mL/min. The fractions were collected and lyophilized to yield 19 as a white solid (0.510 g, 72%). $^1$H NMR (500 MHz, D$_2$O) δ (ppm): 7.45 (m, 1H), 7.37 (m, 1H), 6.98 (m, 2H), 4.42 (s, 2H), 4.17 (d, 1H), 3.90 (d, 1H), 3.51 (br, 2H), 3.35 (br, 1H), 3.24 (br, 1H), 3.00 (br, 1H), 2.91 (br, 1H), 2.33-1.12 (8H). $^{13}$C{$^1$H} NMR (125 MHz, D$_2$O) δ (ppm): 174.5, 170.4, 156.1, 133.3, 132.9, 121.9, 117.1, 116.6, 62.0, 59.6, 53.8, 52.3, 51.0, 48.3, 24.4. Molecular weight for C$_{19}$H$_{26}$N$_2$O$_7$: 394.42. MS (ESI) m/z: Calculated: 395.43 (M+H)$^+$; observed: 395.5.

Na$_2$[Mn$^{II}$cycHBET] (20): 19 (0.26 mmol, 0.103 g) was dissolved in 5 mL water. The pH was adjusted to 8 using 1 N sodium hydroxide solution. MnCl$_2$.4H$_2$O (0.26 mmol, 0.051 g) was then added to the solution and the pH was carefully adjusted to 5. The reaction was stirred for 1 hour, filtered and lyophilized to yield a white solid. The complex was injected onto a reverse phase C18 (Polaris) column and desalted using the method described above. Fractions were collected and lyophilized to yield 20 as a white solid (0.106 g, 80%). Molecular Weight for C$_{19}$H$_{24}$MnN$_2$O$_7$ 447.34. MS (ESI) m/z: Calculated: 448.35 (M+3H)$^+$; Observed: 448.4.

Na[Mn$^{III}$cycHBET] (21): 18 (0.15 mmol, 0.06 g) was dissolved in 5 mL water. The pH was adjusted to 8 using 1 N sodium hydroxide solution. MnCl$_2$.4H$_2$O (0.15 mmol, 0.030 g) was then added to the solution and the pH was adjusted to 12. The solution was allowed to stir for 1 hour. The solution was then filtered through a 0.45 μm filter to remove MnO$_2$, pH adjusted to 11 and the solution was stirred for 18 hour. The reaction was followed using analytical LC-MS and the reaction was stopped when 70% conversion to the Mn$^{III}$ species was observed. The mixture was purified by prep-HPLC as described above. The fractions were collected and lyophilized to yield 21 as a brown solid (0.023 g, 31%). Molecular Weight for C$_{19}$H$_{23}$MnN$_2$O$_7$: 446.33. MS (ESI) m/z: Calculated: 447.34 (M+2H)$^+$; Observed: 447.4.

tert-butyl (2-((2-hydroxy-5-methoxybenzylidene)amino) cyclohexyl)carbamate (22): trans-2-((tert-butoxycarbonyl) amino)cyclohexane (1.30 mmol, 0.279 g) and 2-hydroxy-5-methoxybenzaldehyde (1.35 mmol, 0.206 g) were stirred together in 12 mL MeOH at RT. Within minutes, copious precipitate fell from the bright yellow solution. After 90 min stirring, 30 mL H$_2$O were added to the mixture and 0.342 g (0.98 mmol, 76%) 22 were isolated by filtration. $^1$H NMR (500 MHz, CDCl$_3$) δ (ppm): 12.78 (s, 1H), 8.28 (s, 1H), 6.90 (d, 1H), 6.76 (d), 4.63 (s, 1H), 3.73 (s, 3H) 3.57 (s, 1H), 3.03 (s, 1H), 2.06 (m, 1H), 1.90 (m, 3H), 1.76 (t, 2H), 1.68 (q, 1H), 1.41 (m, 2H), 1.30 (s, 9H). $^{13}$C{$^1$H} NMR (125.7 MHz, CDCl$_3$) δ (ppm): 163.3, 155.4, 155.3, 151.9, 119.3, 118.5, 117.8, 115.0, 79.3, 72.7, 56.1, 54.2, 33.3, 31.6, 28.2, 24.8, 24.0. Molecular Weight for C$_{19}$H$_{28}$N$_2$O$_4$: 348.44. MS (ESI) m/z: Calculated: 349.21 (M+H)$^+$; Observed: 349.2.

tert-butyl trans(2-((2-hydroxy-5-methoxybenzyl)amino) cyclohexyl)carbamate (23) (see FIG. 19): NaBH$_4$ (51 mg, 1.35 mmol) was added portionwise to 22 (0.342 g, 0.98 mmol) stirring in 20 mL MeOH at RT. Within minutes, the yellow color of the solution bleached to pale beige. After 2 h, the solution was concentrated to dryness, taken up in CH$_2$Cl$_2$ and washed thoroughly with H$_2$O and brine. The organic portion was washed dried over MgSO$_4$ and concentrated to 23, isolated as a beige solid (0.179 g, 0.51 mmol, 52%). $^1$H NMR (500 MHz, CDCl$_3$) δ (ppm): 6.72 (m, 2H), 6.54 (s, 1H), 4.53 (br s, 1H), 3.94 (dd, 2H), 3.38 (br s, 1H), 2.30 (m, 1H), 2.13 (m, 1H), 1.97 (m, 1H), 1.69 (m, 2H), 1.45 (s, 9H), 1.31-1.15 (m, 4H). Molecular Weight for C$_{19}$H$_{30}$N$_2$O$_4$: 350.22. MS (ESI) m/z: Calculated: 351.23 (M+H)$^+$; Observed: 351.3.

2-(((trans-2-aminocyclohexyl)amino)methyl)-4-methoxyphenol (24): 23 (0.179 g, 0.51 mmol) was dissolved in 5 mL each CH$_2$Cl$_2$/TFA for 5 hours. The solution was than concentrated to dryness, dissolved in 50 mL CH$_2$Cl$_2$ and stirred over an excess of K$_2$CO$_{3(s)}$ for 12 hours. The K$_2$CO$_3$ was removed by filtration and the mother liquor concentrated to 24 as a pale yellow oil in quantitative yield. $^1$H NMR (500 MHz, CDCl$_3$) δ (ppm): 6.70 (m, 2H), 6.56 (s, 1H), 3.91 (dd, 2H), 3.72 (s, 3H), 2.39 (br t, 1H), 2.10 (m, 2H), 1.79 (m, 1H), 1.66 (m, 2H), 1.28-1.06 (m, 4H)$^{13}$C{$^1$H} NMR (125.7 MHz, CDCl$_3$) δ (ppm): 152.4, 152.0, 124.5, 116.7, 114.0, 113.3, 63.8, 55.9, 55.8, 50.3, 37.0, 30.9, 25.3, 24.9. Molecular Weight for C$_{14}$H$_{22}$N$_2$O$_2$: 250.34. MS (ESI) m/z: Calculated: 251.37 (M+H)$^+$; Observed: 251.1.

2,2'-((trans-2-((2-(tert-butoxy)-2-oxoethyl)(2-hydroxy-5-methoxybenzyl)amino)cyclohexyl)azanediyl)diacetate (25): To 24 (0.161 g, 0.64 mmol) stirring in 3 mL DMF with potassium iodide (0.078 g, 0.47 mmol) and diisopropylethylamine (0.432 g, 3.34 mmol) was added $^t$Bu bromoacetate (0.399 g, 2.05 mmol) at RT. The pale brown solution quickly developed a white precipitate. After 4 hours stirring, the solution was diluted with 100 mL Et$_2$O, washed with Na$_2$CO$_{3(aq)}$, copious H$_2$O and brine. The organic layer was concentrated to dryness and purified using a reverse phase C18 (Polaris) column: eluent A: H$_2$O/0.1% TFA, B: MeCN/ 0.1% TFA; gradient 60% to 95% B over 25 min; flow rate: 20 mL/min. The fractions were lyophilized, than take up in 50 mL CH$_2$Cl$_2$ and stirring over K$_2$CO$_{3(s)}$ for 6 h. The filtrate was concentrated to yield 25. (0.095 g, 0.17 mmol, 26%). $^1$H NMR (500 MHz, CDCl$_3$) δ (ppm): 9.53 (br s, 1H), 6.73 (m, 2H), 6.57 (d, 1H), 4.21 (d, 1H), 3.72 (s, 3H), 3.67 (d, 1H), 3.44 (m, 5H), 3.24 (d, 1H), 2.77 (t, 1H), 2.59 (t, 1H), 2.03 (m, 2H), 1.68 (m, 2H), 1.44 (2s, 18H and 9H), 1.23 (m, 1H), 1.03 (m, 3H). $^{13}$C{$^1$H} NMR (125.7 MHz, CDCl$_3$) δ (ppm): 171.7, 171.3, 152.2, 151.9, 123.5, 116.7, 115.6, 113.7, 81.4, 80.8, 63.7, 59.6, 55.8, 55.5, 52.8, 28.2, 28.1, 25.8, 25.6 (One C could not be found in this spectra, it is likely coincident with another peak). Molecular Weight for C$_{32}$H$_{52}$N$_2$O$_8$: 592.76. MS (ESI) m/z: Calculated: 593.4 (M+H)$^+$; Observed: 593.5.

2,2'-((2-((carboxymethyl)(2-hydroxy-5-methoxybenzyl) amino)cyclohexyl)azanediyl)diacetic acid (26): 25 (0.095 g, 0.224 mmol) was dissolved in 3 mL each CH$_2$Cl$_2$:TFA. After 6 h stirring, the reaction mixture was concentrated to yield 26 as a white solid. Molecular Weight for C$_{20}$H$_{28}$N$_2$O$_8$: 424.44 MS (ESI) m/z: Calculated: 425.19 (M+H)$^+$; Observed: 425.2.

tert-butyl (trans-2-((2-nitrobenzyl)amino)cyclohexyl)carbamate (27): To a solution of 16 (3.99 mmol, 1.001 g) in 90 mL MeOH, NEt$_3$ (4.39 mmol, 0.6 mL) was added and the reaction was stirred for 30 min. To the above mixture a solution of 2-hydroxy-5-nitrobenzaldehyde (3.99 mmol, 0.667 g) in methanol (30 mL) was added. After stirring for 1 h, solid NaBH$_4$ (8.38 mmol, 0.317 g) was added and the reaction was stirred for 3 hours. All the volatiles were removed under reduced pressure, to yield a pale yellow solid. The residue was dissolved in 200 mL CH$_2$Cl$_2$ extracted with 200 mL saturated NaHCO$_3$ solution. The aqueous layer was extracted with CH$_2$Cl$_2$ (2×100 mL). All the organics were combined, washed with brine (200 mL) and dried over anhydrous MgSO$_4$. The solvent was evaporated under reduced pressure to obtain 27 as a pale yellow solid (1.231 g, 96%). $^1$H NMR (500 MHz, CD$_3$OD) δ (ppm): 8.05 (m, 1H), 7.91 (m, 1H), 6.81 (m, 1H), 4.48 (d, 1H), 4.08 (m, 2H), 3.42 (d, 1H), 2.31 (m, 1H), 2.13 (m, 1H), 1.98 (m, 1H), 1.75 (m, 1H), 1.45 (s, 9H), 1.17 (m, 3H). Molecular weight for C$_{18}$H$_{27}$N$_3$O$_5$: 365.42. MS (ESI) m/z: Calculated: 366.42 (M+H)$^+$; observed: 366.5.

di-tert-butyl 2,2'-((trans-2-((2-(tert-butoxy)-2-oxoethyl) (2-hydroxy-5-nitrobenzyl)amino)cyclohexyl)azanediyl)diacetate (28) (see FIG. 19): 27 (3.15 mmol, 1.15 g) was dissolved in CH$_2$Cl$_2$ (100 mL) followed by addition of 50 mL trifluoroacetic acid. The reaction was stirred for 5 h, and then the volatiles were removed under reduced pressure. The residue was dissolved in water (40 mL) and washed with ether (3×40 mL). The water fraction was freeze dried to produce the free amine quantitatively as a pale yellow solid, which was used in subsequent reaction without further purification.

To the round bottom flask containing the amine, KI (6.3 mmol, 1.04 g) was added and system was purged with nitrogen. Under counter nitrogen flow dry dimethylformamide (2 mL) was added followed by the addition of N,N-Diisopropylethylamine (15.75 mmol, 2.74 mL) and dropwise addition of tert-butyl bromoacetate (9.765 mmol, 1.90 g). The reaction was stirred for 18 hours and then partitioned between saturated NaHCO$_3$(aq) and Et$_2$O. The Et$_2$O layer was separated and washed with several changes of H$_2$O to remove DMF before drying over Na$_2$SO$_4$ and concentration to 0.73 g of yellow oil. Molecular weight for C$_{31}$H$_{49}$N$_3$O$_9$: 607.74. MS (ESI) m/z: Calculated: 608.74 (M+H)$^+$; observed: 608.9. The crude product was carried on in the next step without further purification.

2,2'-((trans-2-((carboxymethyl)(2-hydroxy-5-nitrobenzyl)amino)cyclohexyl)azane-diyl)diacetic acid (29): The crude product (28) from the previous step was dissolved was dissolved in trifluroacetic acid (40 mL) followed by addition of triisopropylsilane (2.35 mL), 1-dodecanethiol (2.35 mL) and water (2.35 mL). The reaction was stirred for 5 h, and then the volatiles were removed under reduced pressure. The residue was dissolved in water (40 mL) and washed with ether (3×40 mL). The water fraction was freeze dried to produce crude 29. The product was then purified via preparative HPLC using a Polaris C18 column; eluent A: H$_2$O/0.1% TFA, B: MeCN/0.1% TFA; gradient 5% to 50% B over 25 min; flow rate: 15 mL/min. The fractions were collected and lyophilized to yield 24 as a white solid (0.497 g, 70%). $^1$H NMR (500 MHz, D$_2$O) δ (ppm): 8.37 (d, J=2.58 Hz, 1H), 8.20 (m, 1H), 7.06 (d, J=9.10 Hz, 1H), 4.40 (s, 2H), 4.10 (d, 1H), 3.84 (d, 1H), (d, 1H), 3.56 (br, 1H), 3.44 (br, 1H), 3.19 (br, 2H), 3.04 (br, 2H), 2.35 (m, 1H), 1.89 (m, 1H), 1.78 (m, 1H), 1.53 (m, 1H), 1.24 (br, 4H). $^{13}$C{$^1$H} NMR (125 MHz, D$_2$O) δ (ppm): 173.8, 171.4, 162.8, 141.1, 129.8, 128.5, 119.0, 117.1, 72.1, 71.7, 63.3, 60.0, 55.0, 43.2, 24.7, 24.5, 24.3. Molecular weight for C$_{19}$H$_{25}$N$_3$O$_9$: 439.42. MS (ESI) m/z: Calculated: 440.42 (M+H)$^+$; observed: 440.5.

Na$_2$[Mn$^{II}$cycHBET-NO$_2$)] (30): 29 (0.26 mmol, 0.114 g) was dissolved in 5 mL water. The pH was adjusted to 8 using 1 N sodium hydroxide solution. MnCl$_2$.4H$_2$O (0.26 mmol, 0.051 g) was then added to the solution and the pH was carefully adjusted to 5. The reaction was stirred for 1 h, filtered and lyophilized to yield a white solid. The complex was injected onto a reverse phase C18 (Polaris) column and desalted using the method described above. Fractions were collected and lyophilized to yield 30 as a white solid (0.102 g, 80%). Molecular Weight for C$_{19}$H$_{23}$MnN$_3$O$_9$: 493.35. MS (ESI) m/z: Calculated: 494.35 (M+3H)$^+$; Observed: 494.4.

Na[Mn$^{III}$cycHBET-NO$_2$] (31): MnF$_3$ (0.011 g, 0.08 mmol) was added to 24 (0.043 g, 0.08 mmol) stirring in 5 mL H$_2$O at pH 8. The resultant red-orange solution was purified using a reverse phase C18 (Polaris) column: eluent A: H$_2$O (10 mM ammonium acetate), B: MeCN; gradient 5% to 60% B over 25 min; flow rate: 20 mL/min. The fractions were collected and lyophilized to yield 26 as a brown solid (0.024 g, 0.05 mmol, 62%). Molecular Weight for C$_{19}$H$_{21}$MnN$_3$O$_9$: 490.32. MS (ESI) m/z: Calculated: 490.07 (M)$^-$; Observed: 490.2.

TABLE 1

Relaxivity of Manganese Complexes at pH 7.4, 37° C., 1.4 Tesla.

| Compound | 4 | 5 | 9 | 13 | 14 | 20 | 21 | 30 |
|---|---|---|---|---|---|---|---|---|
| $r_1$ (mM$^{-1}$s$^{-1}$) | 2.76 | 1.05 | 3.11 | 2.28 | 0.34 | 3.26 | 1.56 | 2.30 |

Example 2

Synthesis

Figure 34:
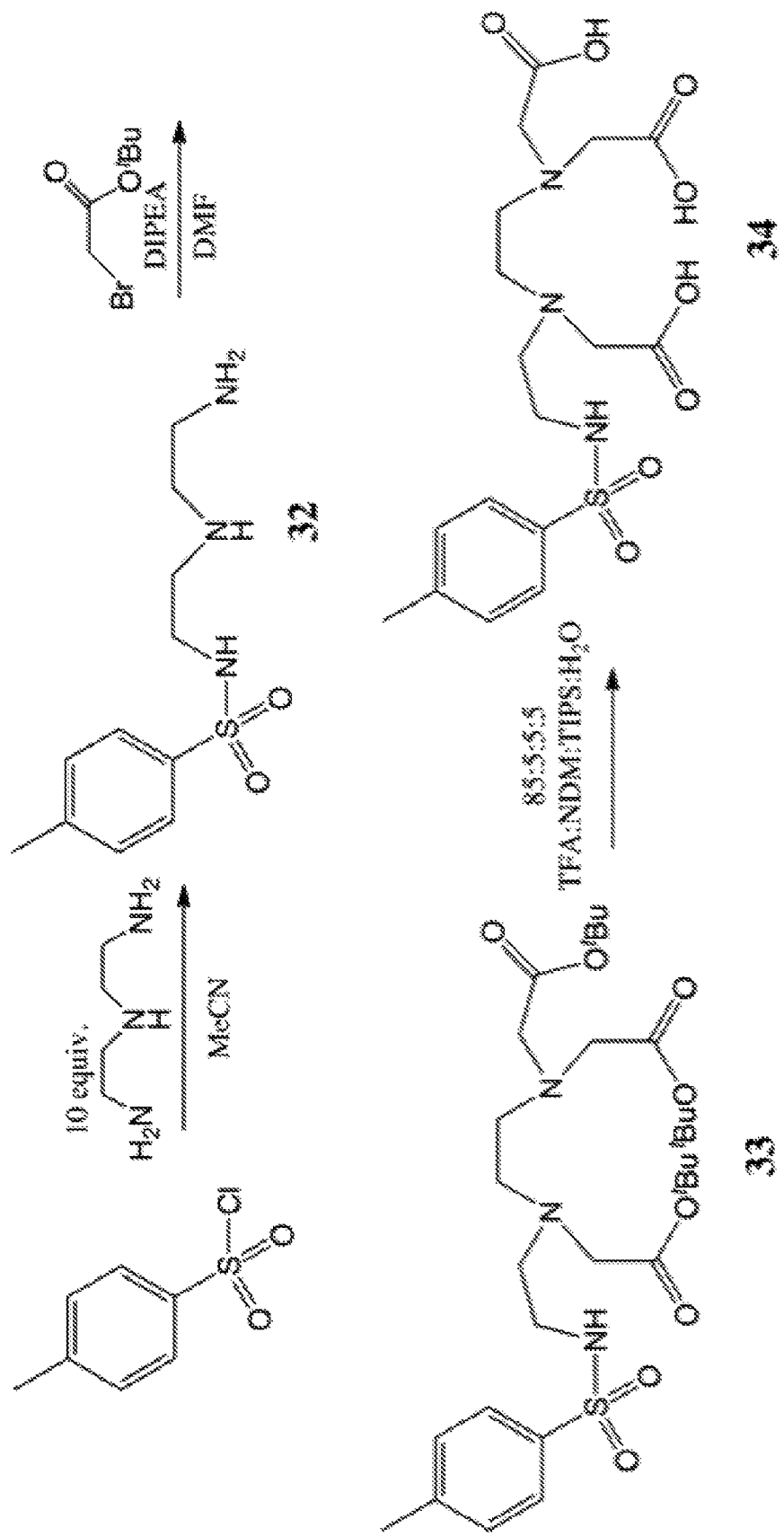
FIG. 34 shows a scheme for the synthesis of N-Tos-DTTA (33).

A synthetic scheme for Example 2 can be found in FIG. 34.

N-tosyl diethylenetriamine (32). To a batch of 8.480 g (81.71 mmol) diethylenetriamine stirring in 120 mL MeCN at 0° C. was added 1.768 g (9.27 mmol) p-toluenesulfonyl chloride. A white heterogeneous solution formed instantly and the solution was warmed to room temperature and left to stir for 16 hours. The solution was subsequently concentrated to a white oil, taken up in 30 mL $H_2O$, the pH adjusted to >10 and washed 2× with $Et_2O$. The aqueous layer was then concentrated to a white residue via lyophilization. The resultant residue was taken up in 30 mL $H_2O$ and the pH adjusted to 7 via careful addition of trifluroacetic acid (TFA). The product was then purified via preparative HPLC using a Restek Ultra Aqueous C18 column (10 mm×250 mm); eluent A: $H_2O$/0.1% TFA, B: MeCN/0.1% TFA; gradient 5% to 95% B over 23 minutes; flow rate: 5 mL/min. The fractions containing product were pooled and MeCN and TFA removed via rotary evaporation. The resultant aqueous solution was than adjusted to pH 9 by careful titration of 1 M NaOH$_{(aq)}$, this step was performed to generate the free amine of small amounts of diethylenetriamine (large excess, no UV detection) that may possibly elute with the product, trace remaining amounts are expected to evaporate during lyophilization. The aqueous solution was concentrated via lyophilization to 3.142 g (5.94 mmol, 64%) of yellow oil comprised of 32+2 equiv. sodium trifluoroacetate. The product was subsequently reacted with no further purification. $^1$H NMR (500 MHZ, $D_2O$, δ from solvent protio): 7.78 (d, 2H), 7.59 (d, 2H), 3.08-2.02 (m, 4H), 2.87 (t, 2H), 2.73 (t, 2H), 2.45 (s, 3H). $^{13}C\{^1H\}$ (125.7 MHz, $D_2O$, δ from tBuOH): 145.77, 135.60, 130.77, 127.40, 47.84, 45.92, 42.27, 39.10, 21.32. ESI-MS: m/z 258.1 (M+H)$^+$; calcd. 258.4.

N-tosyl-N',N'',N''-diethylenetriaminetri$^t$butylacetate (33): To a batch of 2.876 g (5.43 mmol) of 21+2 equiv. sodium trifluoroacetate, 6.615 g (51.18 mmol) diisopropylethylamine and 1.739 g (10.48 mmol) potassium iodide stirring in 20 mL DMF at room temperature was added 5.038 g (23.83 mmol)$^t$butyl bromoacetate in 5 mL DMF dropwise over 20 minutes. The reaction mixture was left to stir for 16 hours before partitioning between satd. NaHCO$_{3(aq)}$ and $Et_2O$. The $Et_2O$ layer was separated and washed with several changes of $H_2O$ to remove DMF before drying over $Na_2SO_4$ and concentration to 4.535 g of brown oil. Chromatography on silica gel 4:1 hexane: ethyl acetate to 2:1 hexane: ethyl acetate yielded 2.346 g (3.91 mmol, 72%) of 33 as a light yellow oil. $^1$H NMR (500 MHZ, CD$_3$Cl, δ from TMS): 7.80 (d, 2H), 7.27 (d, 2H), 6.63 (br, t, NH), 3.42 (s, 4H), 3.16 (s, H), 2.91 (q, 2H), 2.75-2.70 (m, 6H), 2.41 (s, 3H), 1.46 (s, 18H), 1.43 (s, 9H). $^{13}C\{^1H\}$ NMR (125.7 MHZ, CD$_3$Cl, δ from TMS): 171.17, 170.69, 142.79, 137.63, 129.53, 127.44, 81.35, 81.16, 55.73, 52.61, 52.12, 51 77, 41 0.41, 28.32, 28.28, 21.60, 20.80. ESI-MS: m/z 600.8 [M+H]$^+$; calcd.: 600.3.

N-tosyl-N',N'',N''-diethylenetriaminetriacetate.2TFA (N-tos-DTTA. 2TFA) (34). A batch of 0.957 g (1.60 mmol) 33 was stirred in 40 mL of 85:5:5:5 TFA: n-dodecanethiol: triisopropyl silane: $H_2O$ for 16 hours. The reaction mixture was subsequently concentrated to dryness taken up in $H_2O$ and washed with $Et_2O$. The aqueous layer was purified portion-wise via preparative HPLC using a Kromasil 100-10-C4 reverse phase column (21.2 mm×250 mm); eluent A: $H_2O$/0.1% TFA, B: MeCN/0.1% TFA; gradient 5% to 70% B over 17 minutes; flow rate: 20 mL/min. The fractions containing product were pooled and concentrated to 0.894 g (1.29 mmol, 81%) of 23 as a white solid. $^1$H NMR (500 MHZ, $D_2O$, δ from solvent protio): 7.80 (d, 2H), 7.50 (d, 2H), 3.98 (s, 2H), 3.82 (s, 4H), 3.51 (t, 2H), 3.43 (t, 2H), 3.36 (t, 2H), 3.31 (t, 2H), 2.46 (s, 3H). $^{13}C\{^1H\}$ (125.7 MHz, $D_2O$, δ from $^t$BuOH): 173.98, 170.31, 146.48, 135.05, 131.10, 127.76, 56.27, 55.54, 54.80, 53.31, 50.78, 38.62, 21.37. ESI-MS: m/z 432.2 [M+H]$^+$; calcd.: 432.5.

Na[Mn(N-tos-DTTA)] (35). A batch of 81.5 mg (0.12 mmol) 34 was dissolved in 2 mL $H_2O$ and the pH adjusted to 6.40 by careful addition of 1M NaOH. To this was added 23.5 mg (0.12 mmol) of MnCl$_2$ as a solid and the pH carefully adjusted to 6.60. The resultant solution was lyophilized to a while powder before purification via preparative HPLC using a Restek Ultra Aqueous C18 column (10 mm×250 mm); eluent A: 50 mM ammonium acetate in water, B: MeCN; gradient 5% to 95% B over 20 minutes; flow rate: 5 mL/min. The portions containing product were lyophilized repeatedly to remove any remaining ammonium acetate, eventually yielding 35 as 63 mg (0.12 mmol, 100%) of white solids. ESI-MS: m/z 484.0 [M-Na—$H_2O$]$^-$; calcd: 483.4.

Figure 28:
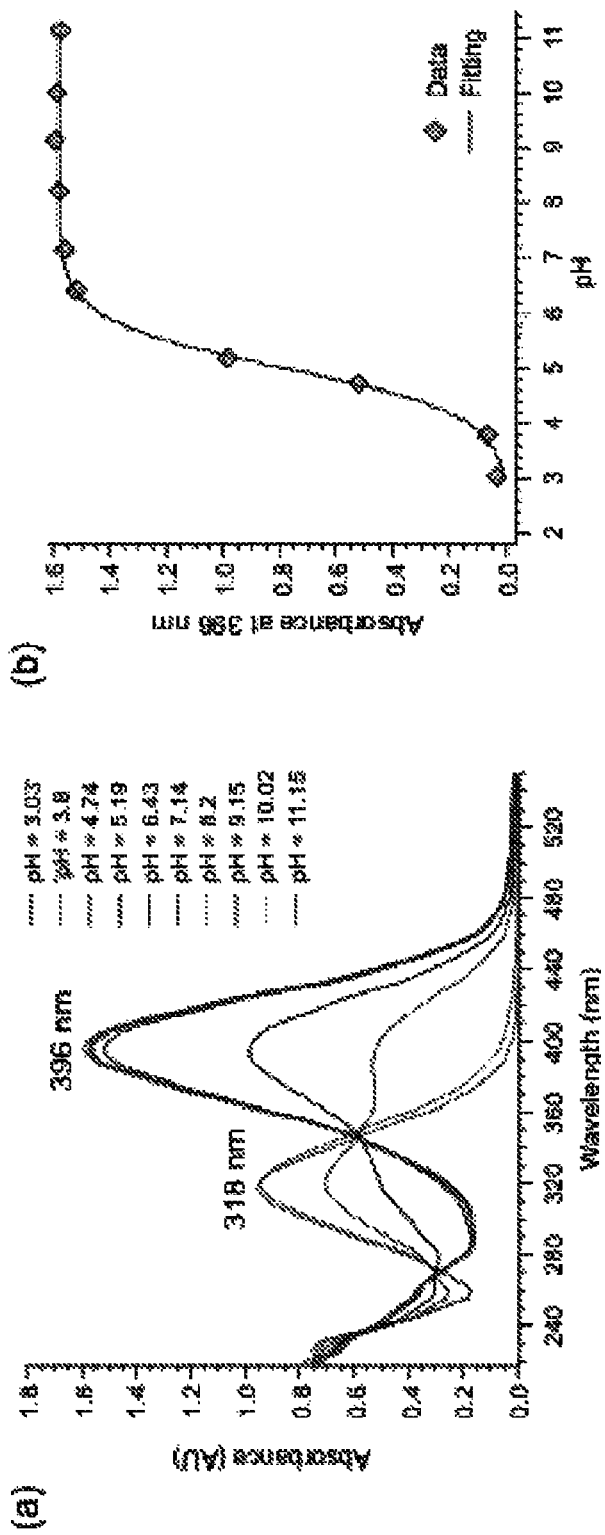
FIG. 28 shows in (a) UV spectrum of $Na[Mn(cycHBET-NO_2)]$ (26) monitored as a function of pH; and in (b) Plot of absorbance at 396 nm as a function of pH. An increase in absorbance corresponds to phenol deprotonation and this can be fit to give a $pK_a$ of 5.01 for this ionization of the phenol.
Figure 29:
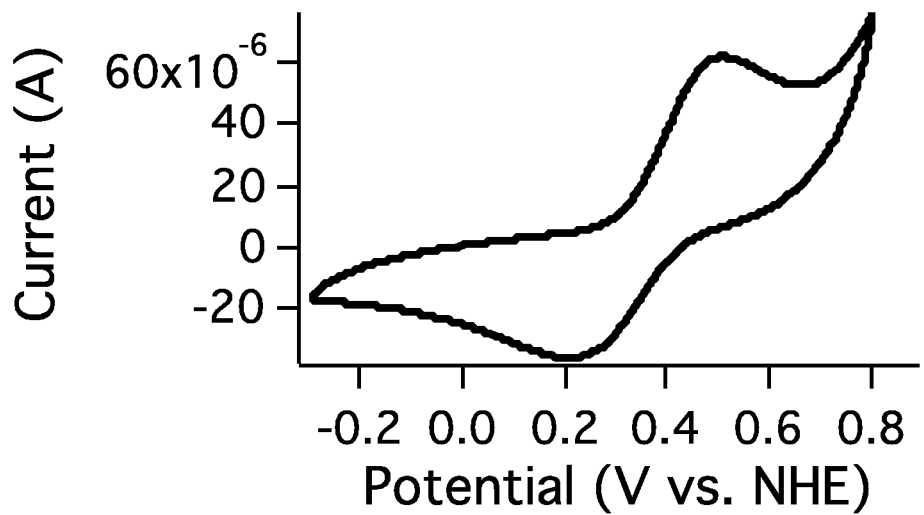
FIG. 29 shows a cyclic voltammogram of $Na_2[Mn^{II}H-BET]$ (4) at pH 7.4; the Half-cell potential is 379 mV vs. normal hydrogen electrode (NHE).
Figure 30:
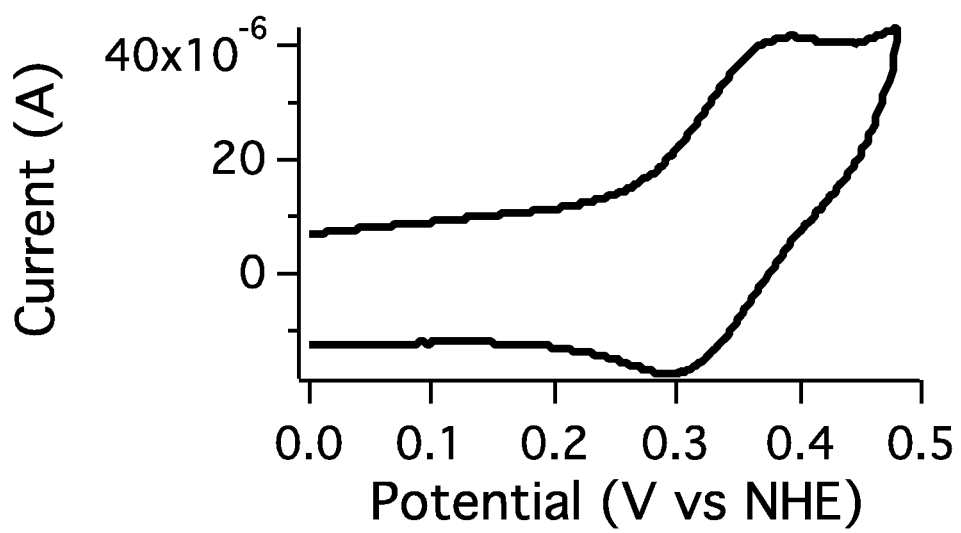
FIG. 30 shows a cyclic voltammogram of $Na_2[Mn^{II}H-BET-OMe]$ (9) at pH 7.4; the Half-cell potential is 344 mV vs. NHE.
Figure 31:
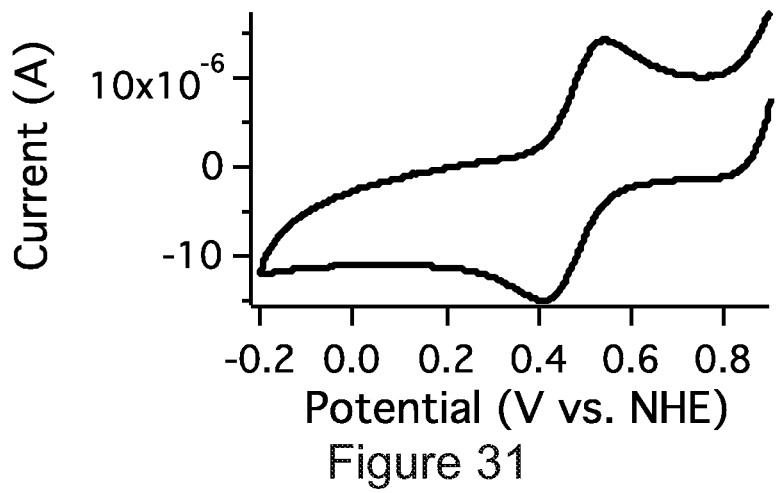
FIG. 31 shows a cyclic voltammogram of $Na[Mn(HBET-NO_2)]$ (14) at pH 7.4; the Half-cell potential is 476 mV vs. NHE.
Figure 32:
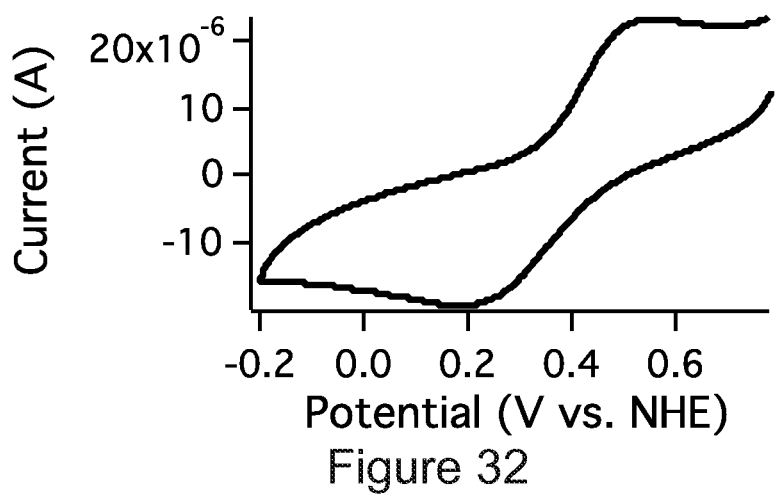
FIG. 32 shows a cyclic voltammogram of $Na[Mn(Cyc-BET)]$ (21) at pH 7.4; the Half-cell potential is 365 mV vs. NHE.
Figure 33:
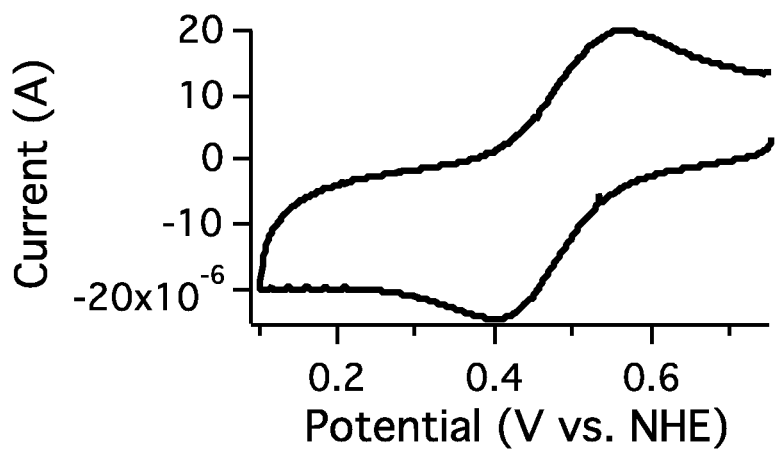
FIG. 33 shows a cyclic voltammogram of $Na[Mn(cycH-BET-NO_2)]$ (31) at pH 7.4; the Half-cell potential is 488 mV vs. NHE.

A 1:1 binding ratio of 34 to Mn$^{2+}$ was determined as follows: To 500 μL samples of 0.91 mM MnCl$_2$ in pH 7.30 buffer (25 mM TRIS) (0.45 μmol present in each), increasingly larger portions of a 1.45 mM 34 (0 to 675 μL in increments of 75 μL; 1.09 μmol present in each 75 μL portion) were added. The $T_2$ value of each sample was subsequently measured and relaxivity plotted as a ratio of ligand to metal (see FIG. 28). The point of full Mn consumption was determined by the point where $r_2$ ceased to decrease with added ligand. Concentration of each sample was determined by ICP-MS.

Example 3

Synthesis

Figure 38:
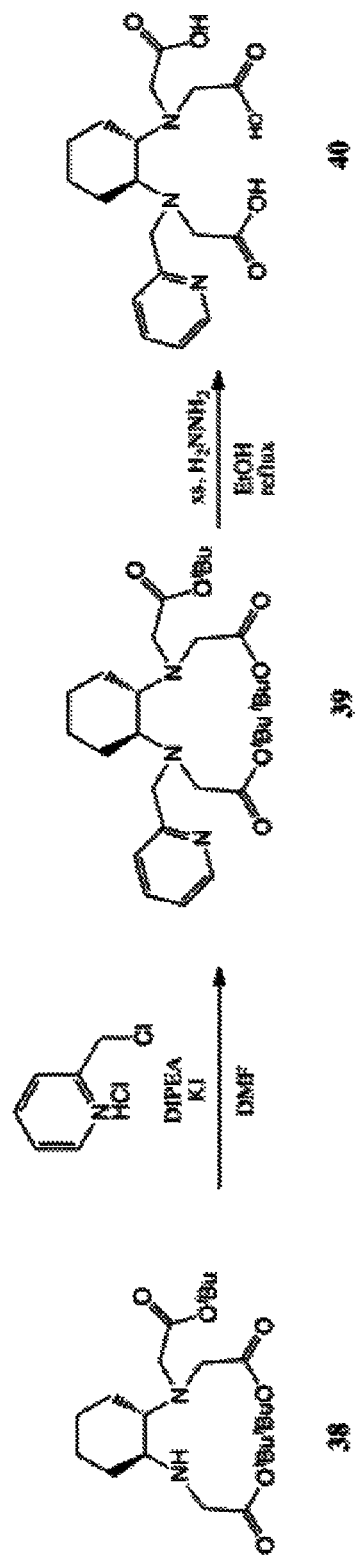
FIG. 38 shows the synthesis of the Mn(II) chelator (40) of the invention.
Figure 39:
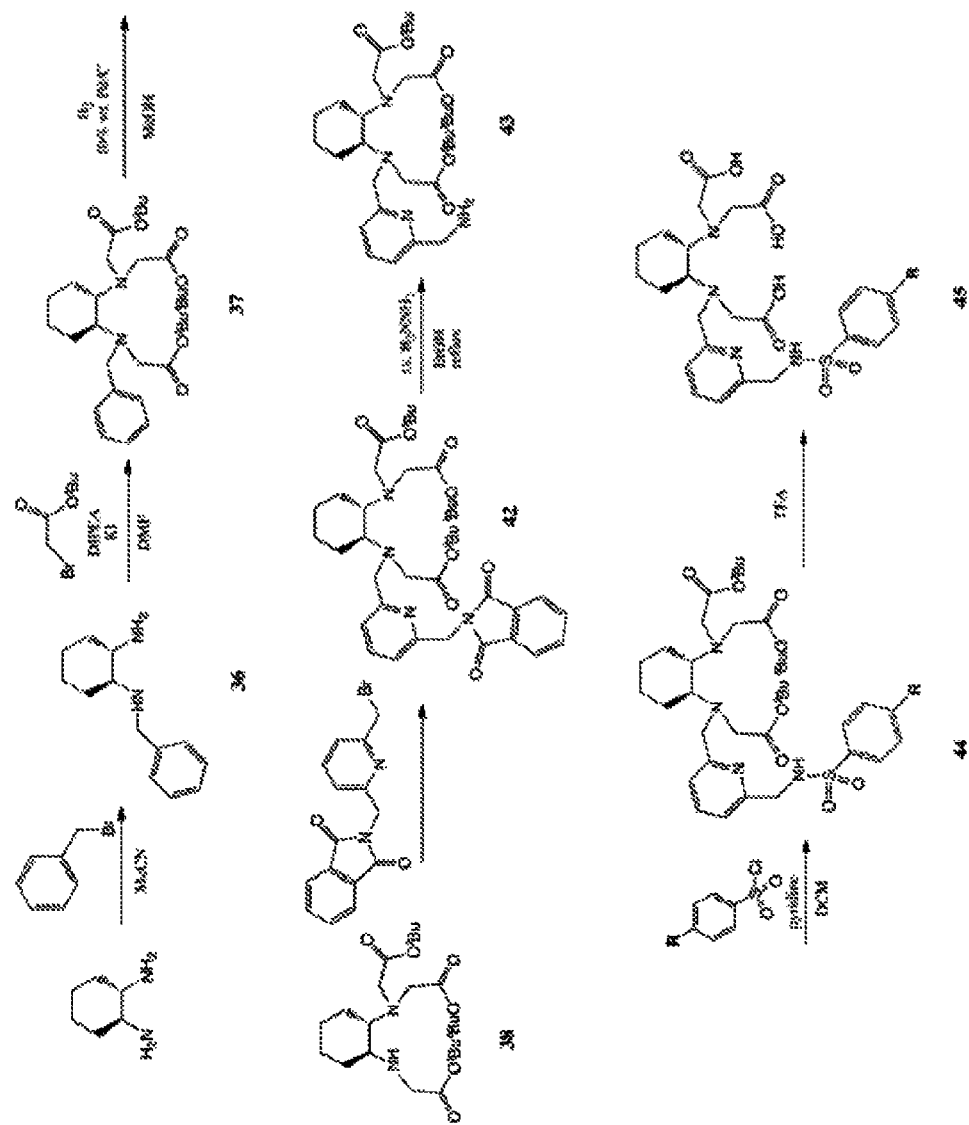
FIG. 39 shows the synthesis of the Mn(II) chelator (45) of the invention.

Synthetic schemes for Example 3 can be found in FIGS. 38 and 39.

N-benzyl-1,2-diaminocyclohexane (36). To a batch of 7.113 g (62.29 mmol) 1,2-diaminocyclohexane in 50 mL MeCN was added dropwise 1.093 g (6.39 mmol) benzyl bromide in 10 mL MeCN at room temperature over the course of 1 hour. After 16 hours, the resultant white, heterogeneous solution was concentrated to dryness and partitioned between $CH_2Cl_2$ and satd. $Na_2CO_{3\ (aq)}$. The layers were separated and the organic phase washed again with satd. $Na_2CO_{3(aq)}$ then brine, dried over $Na_2SO_4$ and concentrated to 1.280 g (6.26 mmol, 98%) of 36 as a light yellow oil. $^1$H NMR (500 MHZ, CDCl$_3$, δ from TMS): 7.36-7.22 (m, 5H), 3.94 (d, 1H), 3.69 (d, 1H), 2.38 (m, 1H), 2.09 (m, 2H), 1.90 (m, 1H), 1.73 (m, 2H), 1.32-1.09 (m, 4H). ESI-MS: m/z=205 [M+H]$^+$; calcd.: 205.3.

N'-benzyl-N',N'',N'''-tritbutylacetate-I,2-cyclohexylenediamine (37): To 1.133 g (5.55 mmol) 36, 4.194 g (32.35 mmol) diisopropylethylamine and 0.966 g (5.82 mmol) potassium iodide in 5 mL DMF was added 5.340 g (27.38 mmol)$^t$butyl bromoacetate at room temperature. The resultant tan, heterogeneous solution was stirred for 6 hours before dilution with $Et_2O$ followed by washing with satd. $K_2CO_{3(aq)}$ several changes of water and brine, drying over $Na_2SO_4$ and concentration to 5.468 g brown oil. Flash chromatography (silica gel, 19:1 to 4:1 hexane:EtOAc) yielded pure 36 as 1.949 g (3.57 mmol, 64%) of light yellow oil. $^1H$ NMR (500 MHZ, $CDCl_3$, δ from TMS): 7.45 (d, 1H), 7.30 (t, 1H), 7.23 (d, 1H), 4.0 (d, 1H), 3.69 (d, 1H), 3.47-3.38 (m, 5H), 3.28 (d, 1H), 2.71 (t, 1H), 2.55 (t, 1H), 2.04 (t, 2H), 1.68 (m, 2H), 1.44 (s, 18H), 1.42 (s, 9H), 1.31-1.25 (m, 4H). $^{13}C\{^1H\}$ NMR (125.7 MHZ, $CD_3Cl$, δ from TMS): 171.95, 171.66, 139.91, 129.35, 128.05, 126.82, 80.30, 63.39, 59.95, 54.79, 53.18, 52.62, 29.41, 28.14, 28.12, 25.83, 25.68. ESI: m/z=547.0 $[M+H]^+$; calcd.: 547.4.

N,N,N'-trans-1,2-diaminocyclohexane-tri-tert-butylacetate (38) 37 (0.757 g, 1.38 mmol) was stirred over Pd/C (96 mg, 13% by wt.) in MeOH under 1 atm $H_{2(g)}$. After 16 h, the Pd/C was removed by filtration and the mother liquor concentrated to 38 (601 mg, 1.32 mmol, 95%) as a beige oil. This product was carried to next steps without further purification. $^1H$ NMR (500 MHZ, $CDCl_3$, δ from TMS): 3.49-3.23 (m, 7H), 2.35 (m, 2H), 2.00 (m, 1H), 1.93 (m, 1H), 1.72 (m, 1H), 1.65 (m, 1H), 1.44 (s, 27H), 1.18-1.00 (m, 4H). $^{13}C\{^1H\}$ NMR (125.7 MHZ, $CD_3Cl$, δ from TMS): 171.7 (two coincidental C), 80.6, 80.5, 67.3, 57.6, 52.8, 48.7, 31.4, 28.3, 28.2, 27.1, 25.9, 24.5. ESI: m/z=457.3 $[M+H]^+$; calcd.: 457.3.

N'-(2-picolyl)-N',N'',N'''-tritbutylacetate-1,2-cyclohexylenediamine (39): Picolyl chloride hydrochloride (0.079 g, 0.48 mmol) was added to 38 (0.250 g, 0.55 mmol), potassium iodide (0.076 g, 0.48 mmol) and diisopropylethylamine (0.320 g, 2.48 mmol) stirring in 3 mL DMF. After 16 hours stirring, the pale yellow and cloudy solution was diluted with 50 mL $Et_2O$, washed with satd. $K_2CO_{3(aq)}$, copious water and brine, dried over Na2SO4 and concentrated to 0.303 g of tan oil. The crude product was purified by flash chromatography (silica gel, 9:1 hexane:EtOAc w/1% TEA) to yield 39 (0.150 g, 0.27 mmol, 50%) as a colorless oil. $^1H$ NMR (500 MHZ, $CDCl_3$, δ from TMS): 8.46 (d, 1H), 7.86 (d, 1H), 7.64 (t, 1H), 7.11 (m, 1H), 4.11 (d, 1H), 3.79 (d, 1H), 3.48-3.32 (m, 5H), 3.29 (d, 1H), 2.71 (m, 1H), 2.61-2.52 (m, 2H), 2.06 (m, 2H), 1.69 (m, 2H), 1.40 (s, 27H), 1.32-1.24 (m, 3H). $^{13}C\{^1H\}$ NMR (125.7 MHZ, $CD_3Cl$, δ from TMS): 171.8, 166.2, 162.5, 146.8, 137.3, 127.0, 123.5, 80.4 (two coincidental signals), 66.6, 63.3, 62.8, 59.0, 37.4, 291, 28.3, 28.1, 26.0, 24.9, 22.7. ESI: m/z=548.4 $[M+H]^+$; calcd.: 548.4.

N'-picolyl-N',N'',N'''-trans-I,2-cyclohexylenediaminetriacetate (40): 39 (150 mg, 0.27 mmol) was stirred in 5 mL each $CH_2Cl_2$/TFA. After 12 h, the solution was concentrated to 40.3TFA (0.15 mmol, 56%) as 104 mg white solids. $^1H$ NMR (500 MHZ, $D_2O$, δ from protio solvent): 8.80 (br s, 1H), 8.59 (s, 1H), 8.07 (br s, 1H), 8.02 (br s, 1H), 4.49-2.94 (m, 10H), 2.32-2.19 (m, 2H), 1.91 (m, 2H), 1.53-1.28 (m, 4H). ESI: m/z=380.2 $[M+H]^+$; calcd. 379.2.

[Mn(CyP3A)] (41): 40 binds $Mn^{III}$ in a 1:1 ratio. This complex was prepared and characterized in situ. $Mn^{III}$ was carefully titrated to 40 and Mn:40 stoichiometry was monitored by LC-MS or $T_2$-relaxometry as describe above. Solutions of 41 are indefinitely stable at room temperature. m/z=433.1 $[M+2H]^+$; calcd. 433.1.

N'-((6-(methylene)pyridin-2-yl)methyl)isoindoline-1,3-dione)-N',N'',N'''-tri$^t$butylacetate-1,2-cyclohexylenediamine (42). A batch of 468 mg (0.86 mmol) 37 and 62 mg of 10% Pd on carbon (13% by wt.) was stirred under 1 atm $H_{2(g)}$ for 16 hours after which full conversion to N'',N''',N''''-tertbutylacetate-1,2-cyclohexylenediamine (42) was confirmed by LC-MS analysis (ESI: m/z=457.0 $[M+H]^+$; calcd: 457.3). The palladium catalyst was removed via filtration and the mother liquor concentrated en vacuo. The resulting residue was immediately taken up in 3 mL DMF and to this was added 186 mg (15.20 mmol) diisopropylethylamine followed by 275 mg (0.83 mmol) 2-((6-(bromomethyl)pyridin-2-yl)methyl)isoindoline-1,3-dione (see *J. Org. Chem.* 1997, 62, 5156). After 6 hours, the reaction mixture was diluted with $Et_2O$ followed by washing with satd. $NaHCO_3(aq)$, several changes of water and brine and drying over $Na_2SO_4$. After removal of $Na_2SO_4$ by filtration, the solution was concentrated to dryness and triturated with hexane leaving behind 241 mg of pale yellow oil. Flash chromatography (silica gel, 100% $CH_2Cl_2$ to 100% MeOH) yielded pure 42 as 77 mg (0.11 mmol, 13%) white residue. $^1H$ NMR (500 MHZ, $CDCl_3$, δ from TMS): 7.88 (m, 2H), 7.72 (m, 3H), 7.58 (t, 1H), 7.03 (d, br, 1H), 4.98 (s, 2H) 3.97 (d, 1H), 3.70 (d, 1H), 3.41 (m, 5H), 3.24 (d, 1H), 2.65 (t, br, 1H), 2.53 (t, br, 1H), 1.99 (m, 2H), 1.636 (m, 2H), 1.40 (s, 27H), 1.37 (m, 4H). $^{13}C\{^1H\}$ NMR (125.7 MHZ, $CD_3Cl$, δ from TMS): 171.87, 171.79, 168.21, 161.15, 153.97, 137.15, 134.12, 132.36, 123.53 122.71, 118.99, 80.48, 80.34, 77.36, 63.50, 61.57, 56.18, 53.77, 53.26, 43.11, 28.22 (two coincidental), 25.97, 25.73. ESI: m/z=707.0 [M+H]+; calcd.: 707.4.

N'-6-(aminomethyl)pyridin-2-yl)methyl-N',N'',N'''-tritbutylacetate-1,2-cyclohexylenediamine (43). A batch of 77 mg (0.11 mmol) 42 and 68 mg of hydrazine monohydrate (1.70 mmol) were refluxed together in 8 mL EtOH. After 90 minutes, the reaction mixture was concentrated to dryness, taken up in $CH_2Cl_2$ and washed with $NaHCO_{3(aq)}$ and brine, dried over $Na_2SO_4$ and concentrated to 65 mg (0.11 mmol, 100%) of 43 as a pale colorless oil. $^1H$ NMR (500 MHZ, $CDCl_3$, δ from TMS): 7.67 (d, 2H), 7.60 (t, 1H), 7.08 (d, 1H, 4.09 (d, 1H) 3.92 (s, 2H), 3.81 (d, 1H), 3.54-3.43 (m, 5H), 3.30 (d, 1H), 2.71 (t, br, 1H), 2.60 (t, br, 1H), 2.17 (d, 2H), 1.89 (m, 2H), 1.43 (s, 18H), 1.43 (s, 9H), 1.26 (m, 4H). $^{13}C\{^1H\}$ NMR (125.7 MHZ, $CD_3Cl$, δ from TMS): 172.0 (two coincidental signals), 171.8, 160.7, 137.0, 122.0, 119.3, 80.51, 80.50, 63.6, 61.6, 56.5, 53.7, 53.3, 47.9, 28.3 (two coincidental signals), 26.0, 25.89. ESI: m/z=577.0 $[M+H]^+$; calcd.: 577.4.

N-6-((4-nitrophenylsulfonamido)methyl)pyridin-2-yl) methyl-N',N'',N'''-tri$^t$butylacetate-1,2-cyclohexylenediamine (44). To 65 mg (0.11 mmol) of 43 and 33 mg (0.32 mmol) triethylamine stirring in 5 mL $CH_2Cl_2$ was added 28 mg (0.13 mmol) of 4-nitrobenzenesulfonyl chloride at 0° C. over 30 minutes. After 16 hours, the reaction mixture was washed with $NaHCO_{3(aq)}$ and brine, dried over $Na_2SO_4$ and concentrated to dryness. Analysis by LC-MS revealed the corresponding aminobissulfone as the major product. Pure 44 was isolated as 4 mg (0.05 mmol, 5%) oily residue after preparative HPLC using a Phenomenex C18 column (10 mm×250 mm); eluent A: $H_2O$/0.1% TFA, B: MeCN/0.1% TFA; gradient 5% to 70% B over 27 minutes; flow rate: 5 mL/min. ESI: m/z=762.0 $[M+H]^+$; calcd.: 762.4.

N-6-((4-nitrophenylsulfonamido)methyl)pyridin-2-yl) methyl-N',N'',N'''-triacetate-1,2-cydohexylellediamine (45). Stirring 2 mg (2.63 μmol) of 44 in TFA showed full conversion to 45 with no by-products detectable by LC-MS analysis. ESI: m/z=594.0 $[M+H]^+$; calcd.: 594.2.

TABLE 2

Relaxivities ($r_1$ in mM$^{-1}$s$^{-1}$) of compounds of Formula (IX) at 37° C. in pH 7.4 Tris buffer

| Compound | 1.41T |
|---|---|
| (IX) | 2.50 |

TABLE 3

Rates (s$^{-1}$) and $t_{1/2}$, (s$^{-1}$) of displacement of Mn (II) (1 mM) by 25 mM. Zn (II) from compounds of Formula (IX) and [Mn(CDTA)]$^{2-}$ at 37° C. in pH 6.0 MES buffer.

| Compound | k | $t_{1/2}$ |
|---|---|---|
| (IX) | 0.0007 ± 1.7e$^{-5}$ | 990 |
| [Mn(CDTA)]$^{2-}$ | 0.0011 ± 2.9e$^{-5}$ | 630 |

Example 4

Synthesis

Figure 40:
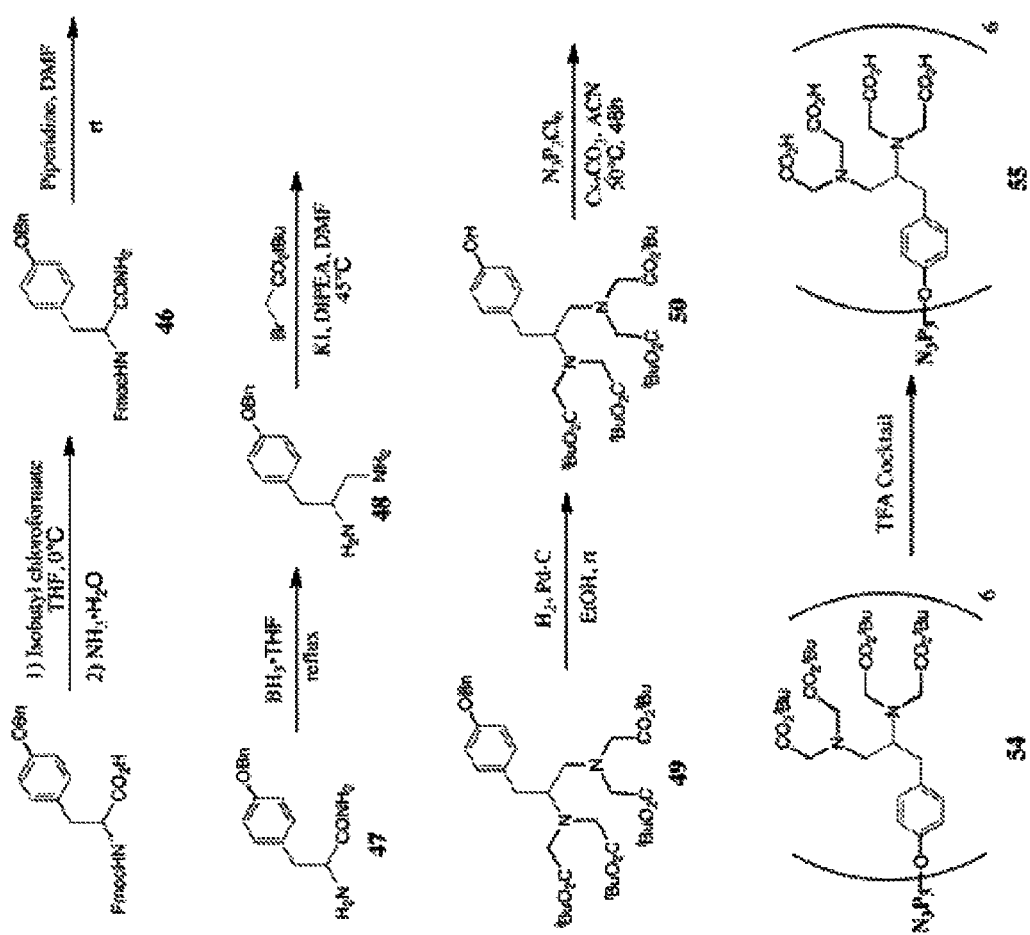
FIG. 40 shows the synthesis of the hexamer ligand (55) of the invention.

A synthetic scheme for Example 4 can be found in FIG. 40.

Fmoc-Ty(OBn)-CONH$_2$: (46): At 0° C., isobutyl chloroform (1.52 g, 11.2 mmol) was added to the mixture of Fmoc-Ty(OBzl)-COOH (4.93 g, 10.0 mmol), N-methylmorpholine (NMM, 2.10 g, 20 mmol) in THF (100 mL) and stirred at 0° C. for 0.5 hours. Aqueous ammonia (30%, 1.2 mL) was added and the reaction mixture was stirred for 1 hour at 0° C. (the reaction solution is cloudy). The precipitate (product and NMM.HCl salts) was filtered off and to the filtrate was added an additional 1.2 mL of aqueous ammonia with stirring for another 0.5 hours at room temperature. The collected solids were suspended in EtOAc (200 mL) and refluxed for 10 min. The insoluble solids were filtered and the filtrate was concentrated under vacuum until the solution turned cloudy. Then, n-hexane (50 mL) was added to precipitate 40 as 2.48 g white solids. n-hexane (80 mL) was then added to the filtrate to precipitate another 2.04 g of the product (4.52 g total, 92%). $^1$H NMR (500 MHZ, CD$_3$Cl, δ from TMS): 7.76 (d, J=7.5 Hz, 2H), 7.54 (t, J=8.1 Hz, 2H), 7.41-7.36 (m, 5H), 7.35-7.29 (m, 3H), 7.12 (s, br, 2H), 6.91 (d, J=7.7 Hz, 2H), 5.56 (s, br, 1H), 5.29 (s, br, 2H), 5.02 (s, 2H), 4.45-4.39 (m, 2H), 4.19 (t, J=6.4 Hz, 1H), 3.07-2.99 (m, 2H). $^{13}$C{$^1$H} NMR (125.7 MHZ, CD$_3$Cl, δ from TMS): 172.96, 157.93, 143.69, 143.64, 141.32, 136.86, 130.36, 128.58, 128.00, 127.75, 127.48, 127.09, 124.98, 120.00, 115.12, 77.26, 77.00, 76.75, 70.02, 66.91, 53.61, 47.19, 37.54. ESI: m/z 493.4 [M+H]$^+$; calcd.: 493.2.

NH$_2$-Ty(OBn)-CONH$_2$ (47): 46 (3.60 g, 7.3 mmol) was dissolved in a solution of 20% piperidine in DMF (40 mL) and stirred at room temperature for 2 hours. The solvent was removed under vacuum and the residue was re-dissolved in EtOAc and precipitated by addition of n-hexane to obtain a white solid: 1.9 g (99%). $^1$H NMR (500 MHZ, CD$_3$Cl, δ from TMS): 7.43-7.31 (m, 5H), 7.15 (d, J=8.5 Hz, 2H), 7.08 (s, 1H), 6.94 (d, J=8.5 Hz, 2H), 5.37 (s, 1H), 5.05 (s, 1H), 3.58 (dd, J=9.3, 4.1 Hz, 1H), 3.19 (dd, J=13.9, 4.0 Hz, 1H), 2.69 (dd, J=13.9, 9.3 Hz, 1H). $^{13}$C{$^1$H} NMR (125.7 MHZ, CD$_3$Cl, δ from TMS): 177.33, 157.82, 136.98, 130.32, 129.95, 128.60, 127.99, 127.46, 115.12, 70.05, 56.56, 40.07. ESI: m/z 271.3 [M+H]$^+$; calcd.: 271.1.

NH$_2$-Ty(OBn)-amine (48): 47 (1.86 g, 6.88 mmol) was suspended in dry THF (10 mL) and BH$_3$.THF (1.0M, 26 mL) was added in. The reaction solution was refluxed for 12 hours under nitrogen atmosphere. The solution was cooled in an ice bath and methanol was slowly added to quench the reaction. After the solvent was removed by evaporation, the yellow residue was redissolved in HCl (1.0 M, 40 mL) and Et$_2$O (50 mL) and stirred at room temperature for 1 hour. After removal of the organic layer, the aqueous solution was placed in an ice bath and the pH was raised to 12 by addition of NaOH. This basic solution was extracted with CH$_2$Cl$_2$ (3×50 mL) and the CH$_2$Cl$_2$ then evaporated to obtain a light-yellow solid (1.39 g, 79%). $^1$H NMR (500 MHZ, CD$_3$Cl, δ from TMS): 7.44-7.31 (m, 5H), 7.11 (d, J=8.5 Hz, 2H), 6.92 (d, J=8.5 Hz, 2H), 5.05 (s, 2H), 2.96-2.88 (m, 1H), 2.80-2.72 (m, 2H), 2.53-2.43 (m, 2H). $^{13}$C{$^1$H} NMR (125.7 MHZ, CD$_3$Cl, δ from TMS): 157.36, 137.10, 131.51, 130.14, 128.56, 127.92, 127.45, 114.87, 70.05, 55.25, 48.21, 41.41. ESI: m/z 257.3 [M+H]$^+$; calcd.: 257.4.

N,N,N',N'-3-(4-(benzyloxy)phenyl)propane-1,2-diamine-tetra-tert-butyl acetate (49): To a mixture of 48 (1.39 g, 5.46 mmol), KI (906 mg, 5.46 mmol), and DIPEA (5.64 g, 43.7 mmol) in dry DMF (30 mL) was added tert-butylbromoacetate (8.52 g, 43.7 mmol) and then stirred for 42 hours at 50° C., with reaction monitoring by LC-MS. After cooling, the DMF was removed under vacuum and to the residue was added H$_2$O (40 mL) and EtOAc (80 mL). The organic layer was separated, washed with water and brine, and evaporated. The residue was purified by column chromatography (SiO$_2$, 1% Et$_3$N in hexane/EtOAc=2/1) to afford the product as a pale yellow oil (3.65 g, 93%). $^1$H NMR (500 MHZ, CD$_3$Cl, δ from TMS): 7.41-7.22 (m, 5H), 7.06 (d, J=7.6 Hz, 2H), 6.80 (m, 2H), 4.95 (s, 2H), 4.66 (s, 1H), 4.52 (m, 1H), 3.43 (s, 4H), 3.36 (s, 4H), 3.23 (m, 1H), 3.02 (m, 1H), 2.78 (m, 1H), 2.51 (m, 1H), 1.44-1.27 (m, 36H). $^{13}$C{1H} NMR (125.7 MHZ, CD$_3$Cl, δ from TMS): 171.72, 170.80, 154.25, 131.20, 130.1, 115.35, 81.20, 81.05, 63.40, 56.30, 55.20, 53.65, 35.65, 28.20. ESI: m/z 713.5 [M+H]$^+$; calcd.: 713.4.

N,N,N',N'-4-(2,3-diaminopropyl)phenol-tetra-tert-butyl acetate (50): Pd/C (10%, 250 mg) was added to a solution of 49 (600 mg, 0.84 mmol) in MeOH (20 mL). The reaction mixture was degassed with a H$_2$ balloon for three times and stirred at room temperature for 2 hours with reaction monitoring by LC-MS. The mixture was filtered and the filtrate was concentrated to give a light-yellow oil which was further purified by column chromatography: DCM/EtOAc (1% Et$_3$N, 0-20%, v/v). Colorless oil: 460 mg (74%).%). $^1$H NMR (500 MHZ, CD$_3$Cl, δ from TMS): 7.07 (d, J=8.3 Hz, 2H), 6.71 (d, J=8.3 Hz, 2H), 4.02 (s, 1H), 3.49 (d, J=3.1 Hz, 4H), 3.43 (d, J=3.3 Hz, 4H), 3.12-3.03 (m, zH), 2.89 (dd, J=13.4, 7.2 Hz, 2H), 2.82 (dd, J=13.8, 5.6 Hz, 2H), 2.62-2.51 (m, 2H), 1.45 (s, 18H), 1.41 (s, 18H). $^{13}$C{$^1$H} NMR (125.7 MHZ, CD$_3$Cl, δ from TMS): 171.39, 170.95, 153.78, 132.35, 130.31, 115.07, 82.56, 80.69, 63.38, 56.27, 55.20, 53.59, 35.97, 28.14. ESI: m/z 623.4 [M+H]$^+$; calcd.: 623.4.

N,N,N',N'-4-(2,3-diaminopropyl)phenol-tetraacetate (51): 50 (200 mg, 0.32 mmol) was dissolved in a mixture of TFA, water, and triisopropyl silane (TIPS) in a 92.5:2.5:5 ratio and the reaction stirred for 2 hours with monitoring by LC-MS. The solvent was removed under reduced pressure and the residue was purified by preparative HPLC to afford a white solid (100 mg, 78%). $^1$H NMR (500 MHZ, D$_2$O, δ): 7.02 (d, J=7.2 Hz, 2H), 6.73 (d, J=7.6 Hz, 2H), 3.78-3.42 (m, 9H), 3.10 (m, 2H), 2.91 (m, 1H), 2.49 (m, 1H). $^{13}$C{$^1$H} NMR (125.7 MHZ, D$_2$O, δ): 173.25, 170.85, 154.43, 130.40, 128.09, 115.72, 60.83, 55.29, 54.46, 52.54, 31.64. ESI: m/z 399.3 [M+H]$^+$; calcd.: 399.2.

Na[Mn(TyOH-EDTA)] (52): This complex was prepared in situ. First, a solution of 51 (8.3 mg) in 2.0 mL of HEPES buffer (100 mM, pH=7.4) was prepared along with a 4.19 mM solution of $MnCl_2$ in HEPES. These solutions were mixed at different ratios and the T2 of solvent water was measured at 1.4 T. From a plot of $1/T_2$ vs. [Mn], the exact ligand concentration was determined. In this plot $1/T_2$ increases linearly with [Mn] until [Mn]=[ligand] and then the slope increases by a factor of 10. For this example, the [ligand] was 2.16 mM. Then, an aliquot of this standardized ligand solution was mixed with 0.95 eq of $MnCl_2$ in HEPES buffer and the concentration measured by ICP-MS.

tert-butyl protected $N_3P_3$-(TyOH-EDTA)$_6$ (53): 51 (547 mg, 0.83 mmol) and cesium carbonate (318 mg, 0.97 mmol) were added at 0° C. to a solution of hexachlorocyclotriphosphazene (45.6 mg, 0.131 mmol) in fresh dry acetonitrile (20 mL) under $N_2$. The reaction mixture was stirred at 45° C. for 2 days and $^1H$ NMR (presence of ortho H peak at δ=6.90 for product vs. δ=6.73 for starting material) and $^{31}P$ NMR (appearance of δ=7.81 peak) were used to monitor the reaction. After the mixture was cooled to room temperature, salts were removed by centrifugation, and the clear solution was concentrated under reduced pressure and subjected to flash chromatography (1% $Et_3N$, DCM/EtOAc) to afford Hexamer-tert-butyl ester as a pale yellow oil (420 mg, 82%). $^1H$ NMR (500 MHZ, $CD_3Cl$, δ from TMS): 7.07 (d, J=8.3 Hz, 12H), 6.90 (d, J=8.6 Hz, 12H), 3.47 (d, J=8.3 Hz, 24H), 3.43 (d, J=4.9 Hz, 24H), 3.11-3.07 (m, 6H), 2.93-2.83 (m, 12H), 2.63-2.53 (m, 12H), 1.43 (s, 108H), 1.39 (s, 108H). $^{13}C\{^1H\}$ NMR (125.7 MHZ, $CD_3Cl$, δ from TMS): 171.31, 170.94, 130.15, 120.69, 80.66, 80.56, 63.42, 56.35, 55.40, 53.65, 28.26, 28.24. $^{31}P$ NMR (202 MHZ, $CD_3Cl$, δ): 7.81. ESI: m/z 1934.0 $[M+2H]^{2+}$; calcd.: 1933.6.

$N_3P_3$-(TyOH-EDTA)$_6$ (54): 53 (410 mg, 0.11 mmol) was dissolved in a mixture of TFA, water, thioanisole, phenol, and ethanedithiol in a 82.5:5:5 ratio and the reaction solution was stirred for 12 hours at room temperature with reaction monitoring by LC-MS. The solution was cooled in an ice bath and cold diethyl ether (50 mL) was added to precipitate the product. The precipitated product was isolated by centrifugation and washed with three times with ether to obtain a white solid (195 mg, 77%). $^1H$ NMR (500 MHZ, $D_2O$, δ): 7.15 (d, J=8.2 Hz, 12H), 6.84 (d, J=8.2 Hz, 12H), 3.69 (d, J=16.7 Hz, 12H), 3.55 (m, 24H), 3.45 (d, J=16.7 Hz, 12H), 3.29 (m, 6H), 3.11 (m, 12H), 2.78-2.60 (m, 6H). $^{13}C\{^1H\}$ NMR (125.7 MHZ, $D_2O$, δ): 174.12, 171.36, 163.06, 162.78, 148.66, 133.63, 130.78, 121.30, 117.43, 115.11, 61.16, 57.08, 54.88, 54.61, 31.71. $^{31}P$ NMR (202 MHZ, $D_2O$, δ): 8.57.

$Mn_6[N_3P_3$-(TyOH-EDTA)$_6]$ (55): This complex was prepared in situ. First, a solution of 54 (11.3 mg) in 2.0 mL of HEPES buffer (100 mM, pH=7.4) was prepared along with a 4.19 mM solution of $MnCl_2$ in HEPES. These solutions were mixed at different ratios and the $T_2$ of solvent water was measured at 1.4 T to determine the concentration of the Hexamer ligand as described for compound 48. Since the hexamer ligand contains 6 EDTA moieties, one hexamer ligand will bind 6 equivalents of Mn. Based on this result, 60 mg of hexamer ligand was then mixed with 24.3 mg of $MnCl_2.4H_2O$ in 2.0 mL deionized water and the pH carefully adjusted to 7.4 with addition of 0.2 M NaOH. This represents a slight (2%) excess of $MnCl_2$ to ensure total chelation. The excess $Mn^{2+}$ was separated from the anionic hexamer complex by passing the solution through a cation exchange column (Alltech, IC-Na) to remove the excess $Mn^{2+}$. The final product was obtained by lyophilization as white solid (60 mg, 85%).

The relaxivities of the compounds for Formulas (XI) and (XII) were determined at different field strengths at 37° C.
in pH 7.4 HEPES buffer. The relaxivity was obtained from the slope of a plot of $1/T_1$ vs. [Mn] for different Mn concentrations. Since Formula (XI) contains 6 Mn per molecule, the ionic (per Mn) and molecular (per molecule) relaxivities are given below.

TABLE 4

Relaxivities ($r_1$ in $mM^{-1}s^{-1}$) of compounds of Formulas (XI) and (XII) measured different field strengths at 37° C. in pH 7.4 HEPES buffer.

| Compound | 0.47T | 1.4T | 4.7T | 9.4T | 11.7T |
|---|---|---|---|---|---|
| (XII) | 3.60 | 2.80 | ND | 3.65 | 3.05 |
| (XI) per Mn | 9.07 | 9.28 | 6.54 | 4.94 | 3.57 |
| (XI) per molecule | 54.4 | 55.7 | 39.2 | 29.6 | 21.4 |

ND = not determined

Thus, the invention provides contrast agents for magnetic resonance imaging, and methods for preparing the contrast agents.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A contrast agent for magnetic resonance imaging, the contrast agent comprising a compound of Formula (IX):

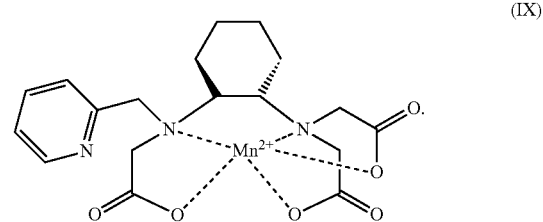

(IX)

2. The contrast agent of claim 1, wherein the Mn is a positron emitting manganese isotope.

3. A pharmaceutical composition, comprising the contrast agent of claim 1 and a pharmaceutically acceptable carrier.

4. The pharmaceutical composition of claim 3, further comprising an additional pharmaceutically active ingredient.

5. A method of diagnostic imaging, comprising administering to a subject a contrast agent comprising a compound of Formula (IX):

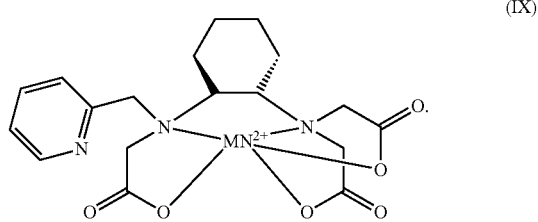

(IX)

6. The method of claim 5, wherein the diagnostic technique is selected from among the group consisting of magnetic resonance imaging (MM), positron emission tomography (PET), and concurrent Mill and PET.

7. The method of claim 5, wherein the Mn is a positron emitting manganese isotope.

8. The method of claim 5, wherein the contrast agent is administered directly to a tissue being diagnostically imaged, to a body fluid that contacts a tissue being diagnostically imaged, or to a body location from which the contrast agent can diffuse or be transported to a tissue being diagnostically imaged.

9. The method of claim 5, wherein the contrast agent is administered intravenously, intramuscularly, subcutaneously, intracerebrally, or intrathecally.

* * * * *

UNITED STATES PATENT AND TRADEMARK OFFICE
CERTIFICATE OF CORRECTION

PATENT NO. : 9,944,668 B2
APPLICATION NO. : 14/759114
DATED : April 17, 2018
INVENTOR(S) : Peter Caravan et al.

Page 1 of 2

It is certified that error appears in the above-identified patent and that said Letters Patent is hereby corrected as shown below:

On the Title Page

Lines 4-9 of Item (71) (Applicants), delete "Peter Caravan, Cambridge, MA (US); Eric M. Gale, Charlestown, MA (US); Galen S. Loving, Charlestown, MA (US); Shereya Mukherjee, Charlestown, MA (US); Jiang Zhu, Charlestown, MA (US)" and insert -- The General Hospital Corporation, Boston, MA (US) --;

Line 4 of Item (72) (Inventors), delete "Shereya Mukherjee" and insert -- Shreya Mukherjee --;

Line 9 of Item (57) Abstract, delete "Mn(ll)" and insert -- Mn(II) --;

Line 11 of Item (57) Abstract, delete "Mn(ll)" and insert -- Mn(II) --;

Line 12 of Item (57) Abstract, delete "Mn(ll)" and insert -- Mn(II) --;

Line 15 of Item (57) Abstract, delete "Mn(ll)" and insert -- Mn(II) --;

In the Claims

Column 38, Lines 56-66, Claim 5, delete " 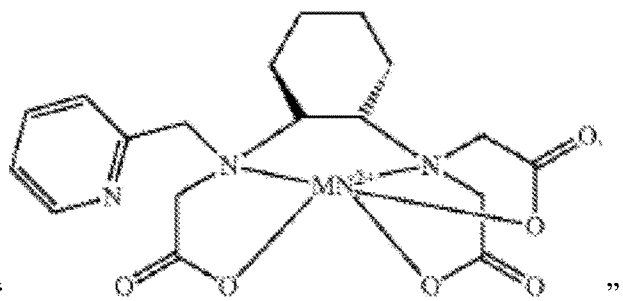 "

Signed and Sealed this
Fourteenth Day of July, 2020

Andrei Iancu
*Director of the United States Patent and Trademark Office*

CERTIFICATE OF CORRECTION (continued)
U.S. Pat. No. 9,944,668 B2 and insert -- 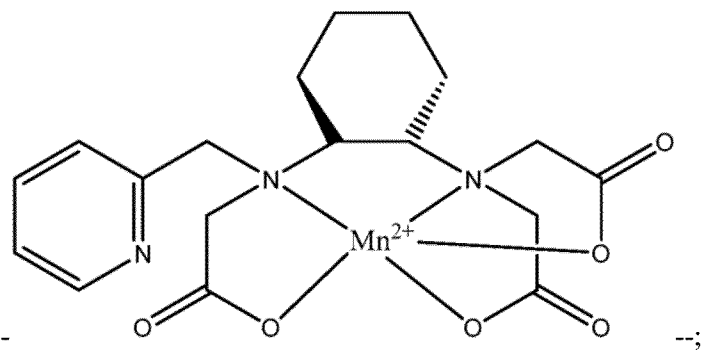 --;

Column 39, Line 3, Claim 6, delete "(MM)" and insert -- (MRI) --;

Column 39, Line 4, Claim 6, delete "Mill" and insert -- MRI --.